(12) United States Patent
Dreyer et al.

(10) Patent No.: US 8,765,763 B2
(45) Date of Patent: Jul. 1, 2014

(54) SUBSTITUTED PIPERAZINES AS CGRP ANTAGONISTS

(75) Inventors: Alexander Dreyer, Gutenzell-Huerbel (DE); Henri Doods, Warthausen (DE); Kai Gerlach, Mittelbiberach (DE); Dirk Gottschling, Mittelbiberach (DE); Annekatrin Heimann, Biberach (DE); Stephan Georg Mueller, Warthausen (DE); Klaus Rudolf, Warthausen (DE); Gerhard Schaenzle, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 122 days.

(21) Appl. No.: 13/322,264

(22) PCT Filed: Jun. 2, 2010

(86) PCT No.: PCT/EP2010/057693
§ 371 (c)(1),
(2), (4) Date: Apr. 3, 2012

(87) PCT Pub. No.: WO2010/139717
PCT Pub. Date: Dec. 9, 2010

(65) Prior Publication Data
US 2012/0196872 A1    Aug. 2, 2012

(30) Foreign Application Priority Data

Jun. 5, 2009 (EP) .................................... 09162068
Oct. 29, 2009 (EP) .................................... 09174459

(51) Int. Cl.
*A61K 31/496* (2006.01)
*A61K 31/499* (2006.01)

(52) U.S. Cl.
USPC ...................... 514/253.04; 544/231; 544/362

(58) Field of Classification Search
CPC ..................................................... C07D 471/04
USPC .................................................. 544/231, 362
See application file for complete search history.

(56) References Cited

FOREIGN PATENT DOCUMENTS

WO    2008020902 A1    11/2011

OTHER PUBLICATIONS

International Search Report, Form PCT/ISA/210, for corresponding PCT/EP2010/057693; date of mailing: Oct. 5, 2010.
Doods et al., CGRP antagonists unravelling the role of CGRP in migraine, Trends in Pharmacological Sciences, Oct. 27, 2007, pp. 580-587, vol. 28, No. 11.

*Primary Examiner* — Brian McDowell
(74) *Attorney, Agent, or Firm* — Michael P. Morris; Alan R. Stempel

(57) ABSTRACT

The present invention relates to new CGRP-antagonists of general formula I

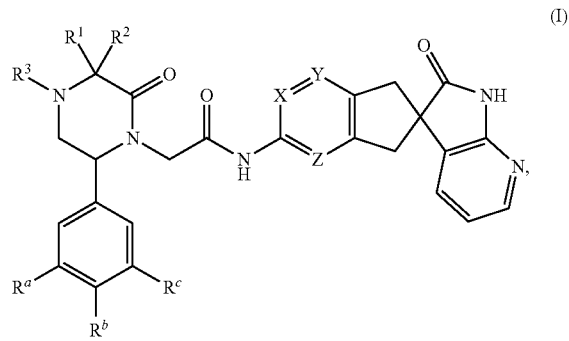

wherein $R^1$, $R^2$, $R^3$, $R^a$, $R^b$, $R^c$, X, Y and Z are defined as mentioned hereinafter, the individual diastereomers, the individual enantiomers and the salts thereof, particularly the physiologically acceptable salts thereof with inorganic or organic acids or bases, medicaments containing these compounds, the use thereof and processes for the preparation thereof.

13 Claims, No Drawings

SUBSTITUTED PIPERAZINES AS CGRP ANTAGONISTS

The present invention relates to new CGRP-antagonists of general formula I

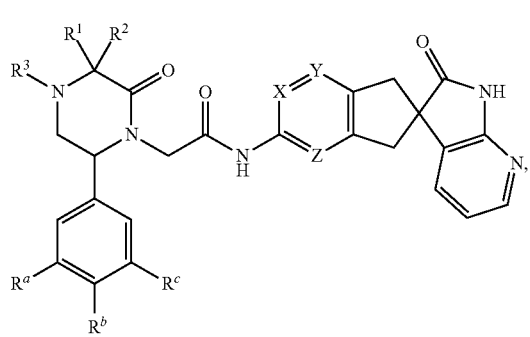

(I)

wherein $R^1$, $R^2$, $R^3$, $R^a$, $R^b$, $R^c$, X, Y and Z are defined as mentioned hereinafter, the individual diastereomers, the individual enantiomers and the salts thereof, particularly the physiologically acceptable salts thereof with inorganic or organic acids or bases, medicaments containing these compounds, the use thereof and processes for the preparation thereof.

Structurally similar compounds with CGRP-antagonistic properties have already been described in the prior art: WO 2008/020902. The compounds according to the present application differ from the prior art essentially in the choice of the groups $R^1$ and $R^2$. Thanks to this structural difference they have potentially improved microsomal stabilities. This leads to longer half-life values, i.e. longer retention times of the substances in the bloodstream.

DETAILED DESCRIPTION OF THE INVENTION

In the above general formula I in a first embodiment

X denotes C—H, C—Cl or N,

Y, Z independently of one another each denote CH or N, wherein at most only one substituent X, Y or Z denotes a nitrogen atom, (a) $R^1$ denotes H, $R^2$ denotes $R^{2.1}$—$C_{0-1}$-alkylene, $R^{2.1}$ denotes a group selected from

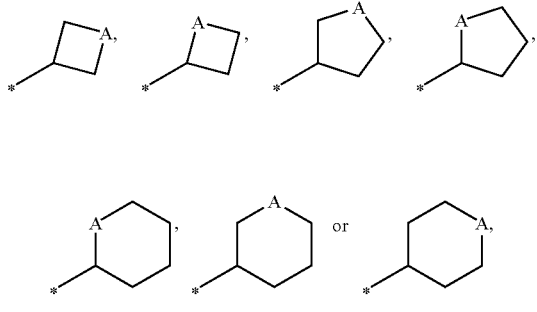

and

A denotes —O—, —S—, —S(O)— or —S(O$_2$)—; or (b) $R^1$ denotes H, $R^2$ denotes $R^{2.1}$—CH$_2$— and $R^{2.1}$ denotes a group

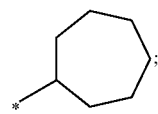

or (c) $R^1$ and $R^2$ together with the carbon atom to which they are attached denote a $C_{4-6}$-cycloalkyl group which is spirocyclically linked in each case to an oxetane or tetrahydropyran ring; or (d) $R^1$ and $R^2$ together with the carbon atom to which they are attached denote a group

and $R^3$ denotes H, —C(O)—O—$C_{1-4}$-alkyl or a $C_{1-6}$-alkyl group which may be substituted by 1, 2, 3, 4 or 5 fluorine atoms, $R^a$ denotes H, F, —OCH$_3$ or —OCF$_3$, $R^b$ denotes H, F, —OCH$_3$ or —OCF$_3$, and $R^c$ denotes H, F, —OCH$_3$ or —OCF$_3$, the individual diastereomers, the individual enantiomers and the salts thereof, particularly the physiologically acceptable salts thereof with inorganic or organic acids or bases.

A second embodiment of the present invention comprises the compounds of the above general formula I, wherein X, Y, Z in each case denote C—H or N, while there is at most only one N in the ring, (a) $R^1$ denotes H and $R^2$ denotes a group selected from

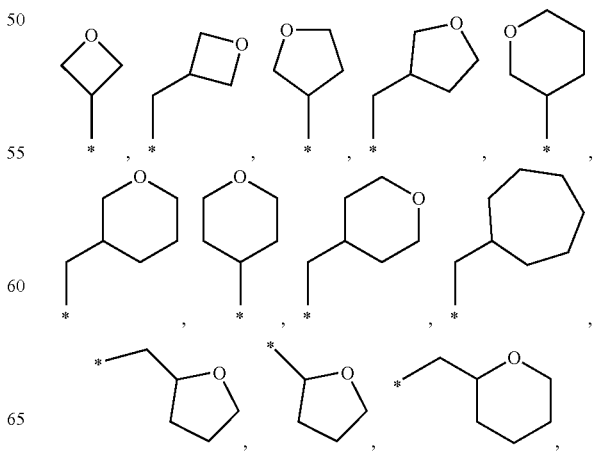

-continued

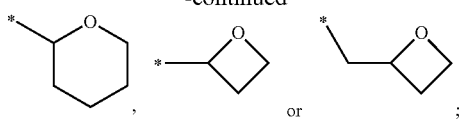

or (b) $R^1$ and $R^2$ together with the carbon atom to which they are attached denote a group selected from

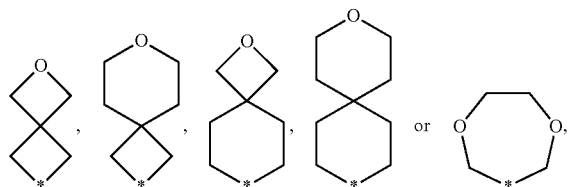

and
$R^3$ denotes H, —C(O)—O—$C_{1-4}$-alkyl or a $C_{1-6}$-alkyl group which may be substituted by 1, 2, 3, 4 or 5 fluorine atoms,
$R^a$ denotes H, F, —$OCH_3$ or —$OCF_3$,
$R^b$ denotes H, F, —$OCH_3$ or —$OCF_3$, and
$R^c$ denotes H, F, —$OCH_3$ or —$OCF_3$,
the individual diastereomers, the individual enantiomers and the salts thereof, particularly the physiologically acceptable salts thereof with inorganic or organic acids or bases.

A third embodiment of the present invention comprises the compounds of the above general formula I, wherein
X, Y, Z in each case denotes C—H or N, while there is at most only one N in the ring,
$R^1$ denotes H,
$R^2$ denotes a group selected from

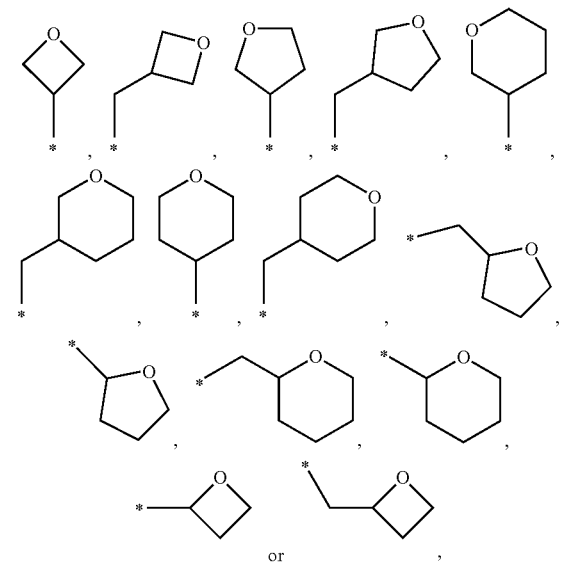

$R^3$ denotes H, —C(O)—O—$C_{1-4}$-alkyl or a $C_{1-6}$-alkyl group which may be substituted by 1, 2, 3, 4 or 5 fluorine atoms,
$R^a$ denotes H, F, —$OCH_3$ or —$OCF_3$,
$R^b$ denotes H, F, —$OCH_3$ or —$OCF_3$, and
$R^c$ denotes H, F, —$OCH_3$ or —$OCF_3$,
the individual diastereomers, the individual enantiomers and the salts thereof, particularly the physiologically acceptable salts thereof with inorganic or organic acids or bases.

A fourth embodiment of the present invention comprises the compounds of the above general formula I, wherein
X, Y, Z in each case denotes C—H or N, while there is at most only one N in the ring,
$R^1$ denotes H,
$R^2$ denotes a group

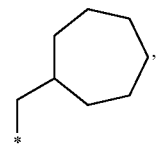 [SMILES: *CC1CCCCCC1]

$R^3$ denotes H, —C(O)—O—$C_{1-4}$-alkyl or a $C_{1-6}$-alkyl group which may be substituted by 1, 2, 3, 4 or 5 fluorine atoms,
$R^a$ denotes H, F, —$OCH_3$ or —$OCF_3$,
$R^b$ denotes H, F, —$OCH_3$ or —$OCF_3$, and
$R^c$ denotes H, F, —$OCH_3$ or —$OCF_3$,
the individual diastereomers, the individual enantiomers and the salts thereof, particularly the physiologically acceptable salts thereof with inorganic or organic acids or bases.

A fifth embodiment of the present invention comprises the compounds of the above general formula I, wherein
X, Y, Z in each case denotes C—H or N, while there is at most only one N in the ring,
$R^1$ and $R^2$ together with the carbon atom to which they are attached, denote a group selected from

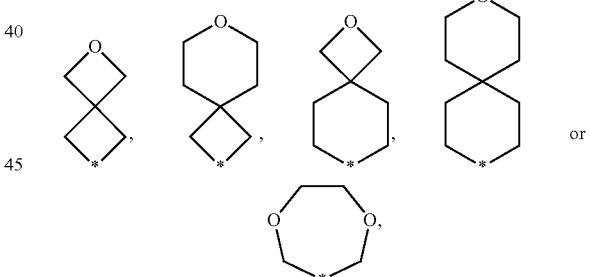

$R^3$ denotes H, —C(O)—O—$C_{1-4}$-alkyl or a $C_{1-6}$-alkyl group which may be substituted by 1, 2, 3, 4 or 5 fluorine atoms,
$R^a$ denotes H, F, —$OCH_3$ or —$OCF_3$,
$R^b$ denotes H, F, —$OCH_3$ or —$OCF_3$, and
$R^c$ denotes H, F, —$OCH_3$ or —$OCF_3$,
the individual diastereomers, the individual enantiomers and the salts thereof, particularly the physiologically acceptable salts thereof with inorganic or organic acids or bases.

A sixth embodiment of the present invention comprises the compounds of the above general formula I, wherein
X, Y, Z in each case denotes C—H or N, while there is at most only one N in the ring, R¹ and R² together with the carbon atom to which they are attached denote a group

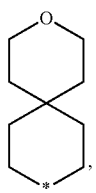

R³ denotes H, —C(O)—O—C₁₋₄-alkyl or a C₁₋₆-alkyl group which may be substituted by 1, 2, 3, 4 or 5 fluorine atoms,
R$^a$ denotes H, F, —OCH₃ or —OCF₃,
R$^b$ denotes H, F, —OCH₃ or —OCF₃, and
R$^c$ denotes H, F, —OCH₃ or —OCF₃,
the individual diastereomers, the individual enantiomers and the salts thereof, particularly the physiologically acceptable salts thereof with inorganic or organic acids or bases.

A seventh embodiment of the present invention comprises the compounds of the above general formula I, wherein
X, Y, Z in each case denote C—H or N, while there is at most only one N in the ring,
R¹ and R² together with the carbon atom to which they are attached denote a group

R³ denotes H, —C(O)—O—C₁₋₄-alkyl or a C₁₋₆-alkyl group which may be substituted by 1, 2, 3, 4 or 5 fluorine atoms,
R$^a$ denotes H, F, —OCH₃ or —OCF₃,
R$^b$ denotes H, F, —OCH₃ or —OCF₃, and
R$^c$ denotes H, F, —OCH₃ or —OCF₃,
the individual diastereomers, the individual enantiomers and the salts thereof, particularly the physiologically acceptable salts thereof with inorganic or organic acids or bases.

An eighth embodiment of the present invention comprises the compounds of general formula Ia (Ia)

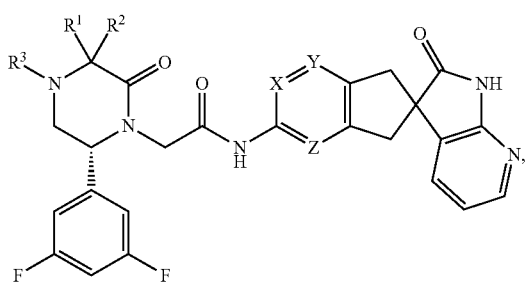

wherein R¹, R², X, Y and Z are as hereinbefore defined in the embodiment 1, 2, 3, 4, 5, 6 or 7 and
R³ denotes H or CH₃,
the individual diastereomers, the individual enantiomers as well as the salts thereof, particularly the physiologically acceptable salts thereof with inorganic or organic acids or bases.

A ninth embodiment of the present invention comprises the compounds of general formula Ib (Ib)

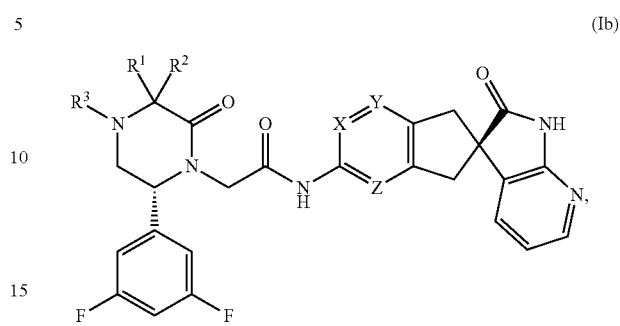

wherein R¹, R², X, Y and Z are as hereinbefore defined in the embodiment 1, 2, 3, 4, 5, 6 or 7 and
R³ denotes H or CH₃,
the individual diastereomers, the individual enantiomers as well as the salts thereof, particularly the physiologically acceptable salts thereof with inorganic or organic acids or bases.

A tenth embodiment of the present invention comprises the compounds of general formula Ic (Ic)

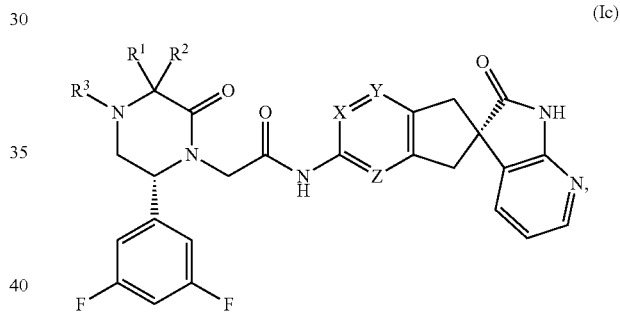

wherein R¹, R², X, Y and Z are as hereinbefore defined in the embodiment 1, 2, 3, 4, 5, 6 or 7 and
R³ denotes H or CH₃,
the individual diastereomers, the individual enantiomers as well as the salts thereof, particularly the physiologically acceptable salts thereof with inorganic or organic acids or bases.

An eleventh embodiment of the present invention comprises the compounds of the above general formula I wherein R¹, R², R³, R$^a$, R$^b$ and R$^c$ are as hereinbefore defined in the embodiment 1, 2, 3, 4, 5, 6, or 7,
X denotes CH or N,
Y denotes CH and
Z denotes CH,
the individual diastereomers, the individual enantiomers as well as the salts thereof, particularly the physiologically acceptable salts thereof with inorganic or organic acids or bases.

A twelfth embodiment of the present invention comprises the compounds of the above general formula Ia, wherein R¹ and R² are as hereinbefore defined in the embodiment 1, 2, 3, 4, 5, 6, or 7,
R³ denotes H or CH₃,
X denotes CH or N, Y denotes CH and
Z denotes CH,
the individual diastereomers, the individual enantiomers as well as the salts thereof, particularly the physiologically acceptable salts thereof with inorganic or organic acids or bases.

A thirteenth embodiment of the present invention comprises the compounds of the above general formula Ib, wherein $R^1$ and $R^2$ are as hereinbefore defined in the embodiment 1, 2, 3, 4, 5, 6, or 7,
$R^3$ denotes H or $CH_3$,
X denotes CH or N,
Y denotes CH and
Z denotes CH,
the individual diastereomers, the individual enantiomers as well as the salts thereof, particularly the physiologically acceptable salts thereof with inorganic or organic acids or bases.

A fourteenth embodiment of the present invention comprises the compounds of the above general formula Ic, wherein $R^1$ and $R^2$ are as hereinbefore defined in the embodiment 1, 2, 3, 4, 5, 6, or 7,
$R^3$ denotes H or $CH_3$,
X denotes CH or N,
Y denotes CH and
Z denotes CH,
the individual diastereomers, the individual enantiomers as well as the salts thereof, particularly the physiologically acceptable salts thereof with inorganic or organic acids or bases.

The following compounds are mentioned as examples of most particularly preferred compounds of the above general formula I:

| No. | Structure |
|---|---|
| (1) | 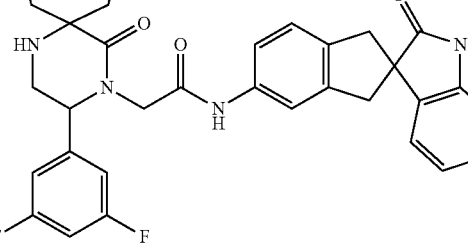 |
| (1a) | 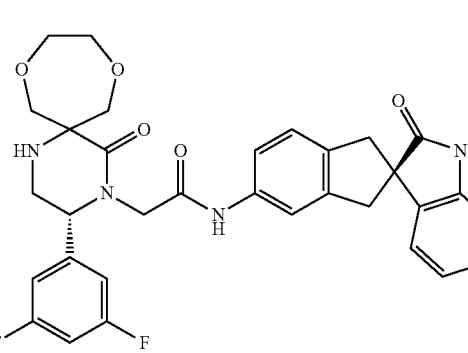 |
| (1b) | 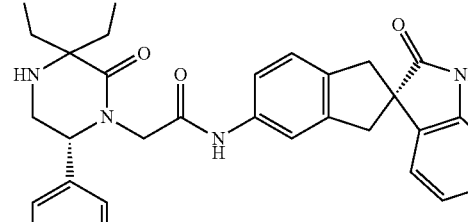 |

| No. | Structure |
|---|---|
| (2) | 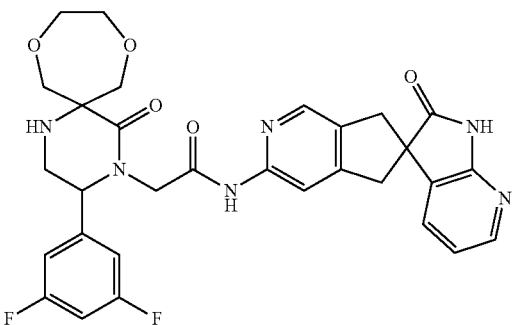 [SMILES: O=C(CN1C(=O)C2(COCCOC2)NCC1c1cc(F)cc(F)c1)Nc1cc2c(cn1)CC1(C2)C(=O)Nc2ncccc21] |
| (3) | 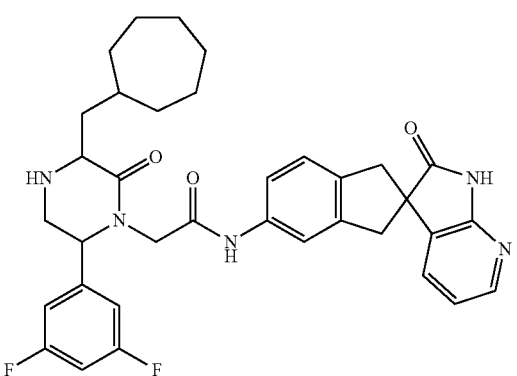 [SMILES: O=C(CN1C(=O)C(CC2CCCCCC2)NCC1c1cc(F)cc(F)c1)Nc1ccc2c(c1)CC1(C2)C(=O)Nc2ncccc21] |
| (4) | 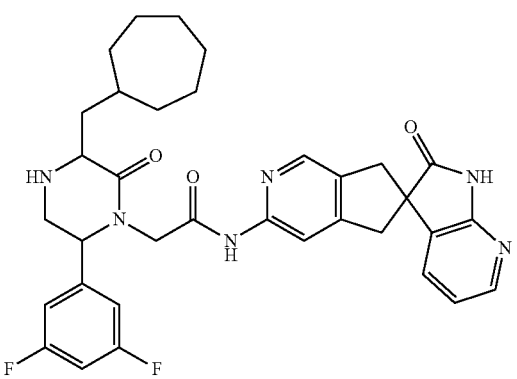 [SMILES: O=C(CN1C(=O)C(CC2CCCCCC2)NCC1c1cc(F)cc(F)c1)Nc1cc2c(cn1)CC1(C2)C(=O)Nc2ncccc21] |
| (5) | 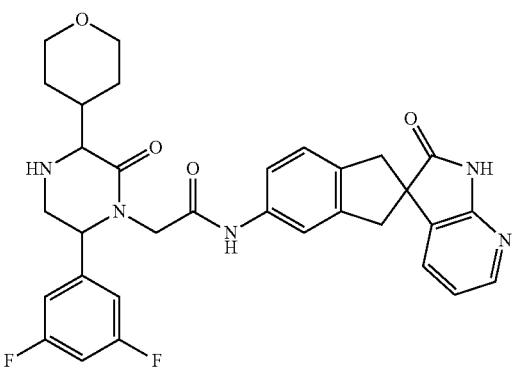 [SMILES: O=C(CN1C(=O)C(C2CCOCC2)NCC1c1cc(F)cc(F)c1)Nc1ccc2c(c1)CC1(C2)C(=O)Nc2ncccc21] |

| No. | Structure |
|---|---|
| (6) | 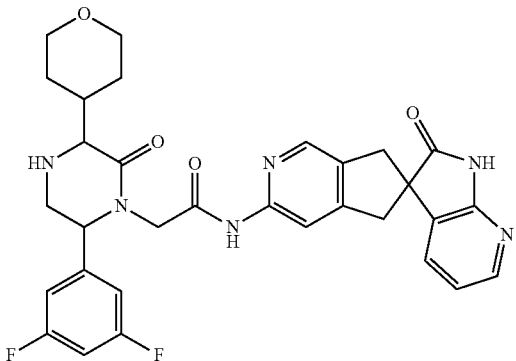 [SMILES: O=C(CN1C(=O)C(C2CCOCC2)NCC1c1cc(F)cc(F)c1)Nc1cc2c(cn1)CC1(C2)C(=O)Nc2ncccc21] |
| (7) | 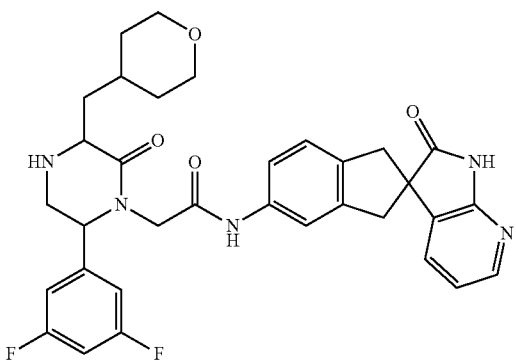 [SMILES: O=C(CN1C(=O)C(CC2CCOCC2)NCC1c1cc(F)cc(F)c1)Nc1ccc2c(c1)CC1(C2)C(=O)Nc2ncccc21] |
| (8) | 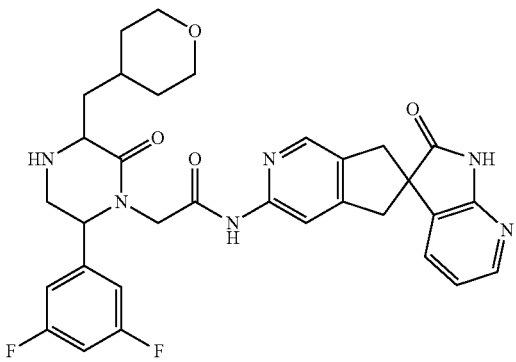 [SMILES: O=C(CN1C(=O)C(CC2CCOCC2)NCC1c1cc(F)cc(F)c1)Nc1cc2c(cn1)CC1(C2)C(=O)Nc2ncccc21] |
| (9) | 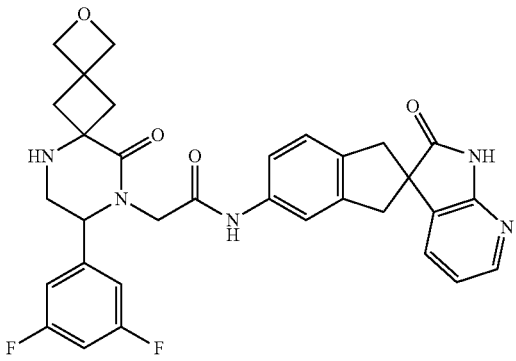 [SMILES: O=C(CN1C(=O)C2(CC3(COC3)C2)NCC1c1cc(F)cc(F)c1)Nc1ccc2c(c1)CC1(C2)C(=O)Nc2ncccc21] |

-continued

| No. | Structure |
|---|---|
| (10) | 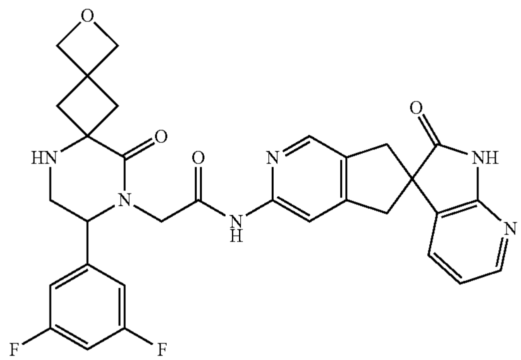 [SMILES: O=C(CN1C(=O)C2(CC3(COC3)C2)NCC1c1cc(F)cc(F)c1)Nc1cc2c(cn1)CC1(C2)C(=O)Nc2ncccc21] |
| (11) | 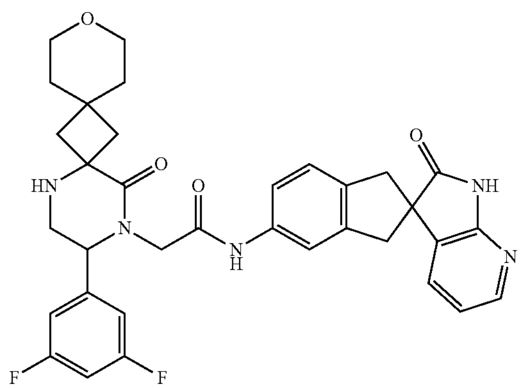 [SMILES: O=C(CN1C(=O)C2(CC3(CCOCC3)C2)NCC1c1cc(F)cc(F)c1)Nc1ccc2c(c1)CC1(C2)C(=O)Nc2ncccc21] |
| (12) | 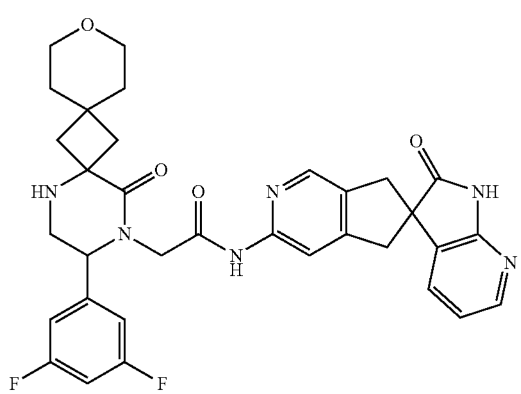 [SMILES: O=C(CN1C(=O)C2(CC3(CCOCC3)C2)NCC1c1cc(F)cc(F)c1)Nc1cc2c(cn1)CC1(C2)C(=O)Nc2ncccc21] |
| (13) | 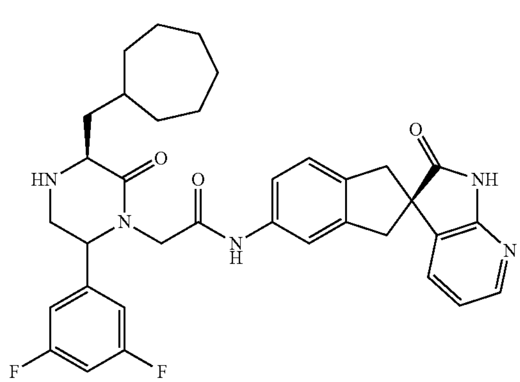 [SMILES: O=C(CN1C(=O)[C@H](CC2CCCCCC2)NCC1c1cc(F)cc(F)c1)Nc1ccc2c(c1)C[C@@]1(C2)C(=O)Nc2ncccc21] |

| No. | Structure |
|---|---|
| (14) | 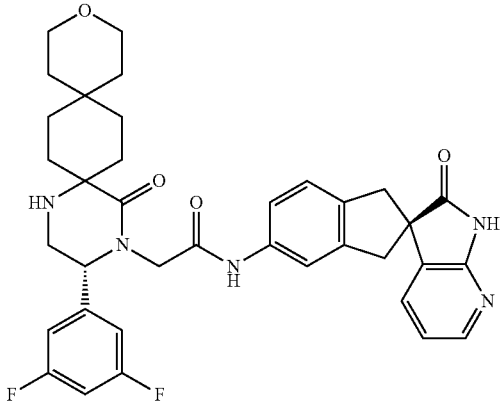 [SMILES: O=C(CN1C(=O)C2(CCC3(CCOCC3)CC2)NC[C@H]1c1cc(F)cc(F)c1)Nc1ccc2c(c1)C[C@@]1(C2)C(=O)Nc2ncccc21] |
| (15) | 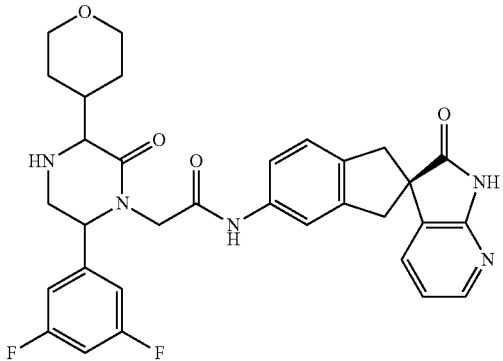 [SMILES: O=C(CN1C(=O)C(C2CCOCC2)NCC1c1cc(F)cc(F)c1)Nc1ccc2c(c1)C[C@@]1(C2)C(=O)Nc2ncccc21] |
| (16) | 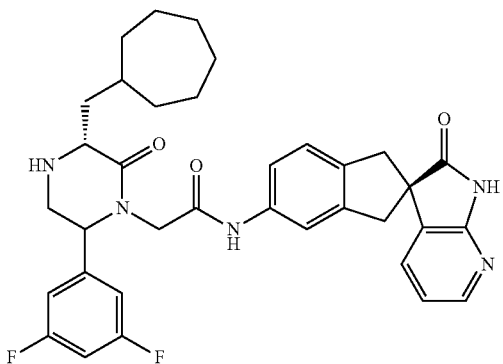 [SMILES: O=C(CN1C(=O)[C@@H](CC2CCCCCC2)NCC1c1cc(F)cc(F)c1)Nc1ccc2c(c1)C[C@@]1(C2)C(=O)Nc2ncccc21] |
| (17) | 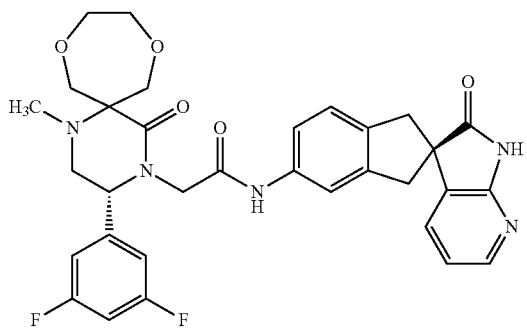 [SMILES: CN1C[C@@H](c2cc(F)cc(F)c2)N(CC(=O)Nc2ccc3c(c2)C[C@@]2(C3)C(=O)Nc3ncccc32)C(=O)C12COCCOC2] |

| No. | Structure |
|---|---|
| (18) | 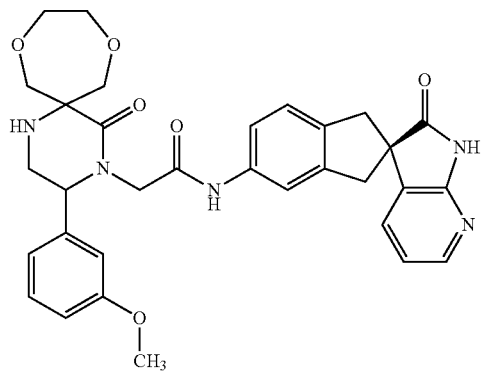 [SMILES: COc1cccc(C2CNC3(COCCOC3)C(=O)N2CC(=O)Nc2ccc3c(c2)C[C@@]2(C3)C(=O)Nc3ncccc32)c1] |
| (19) | 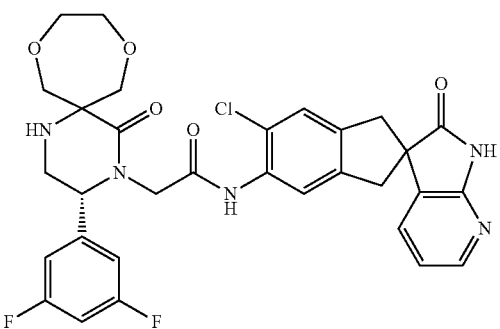 [SMILES: O=C(CN1C(=O)C2(COCCOC2)NC[C@H]1c1cc(F)cc(F)c1)Nc1cc2c(cc1Cl)CC1(C2)C(=O)Nc2ncccc21] |
| (20) | 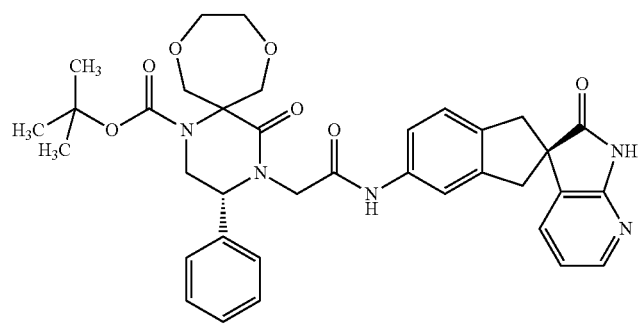 [SMILES: CC(C)(C)OC(=O)N1C[C@@H](c2ccccc2)N(CC(=O)Nc2ccc3c(c2)C[C@@]2(C3)C(=O)Nc3ncccc32)C(=O)C12COCCOC2] |
| (21) | 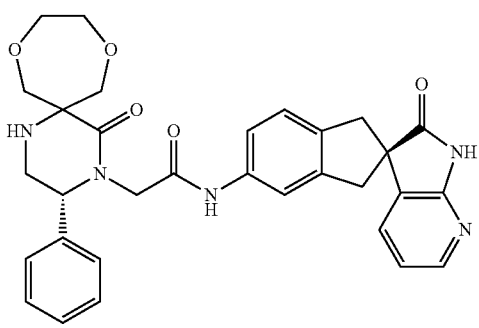 [SMILES: O=C(CN1C(=O)C2(COCCOC2)NC[C@H]1c1ccccc1)Nc1ccc2c(c1)C[C@@]1(C2)C(=O)Nc2ncccc21] |

| No. | Structure |
|---|---|
| (22) | 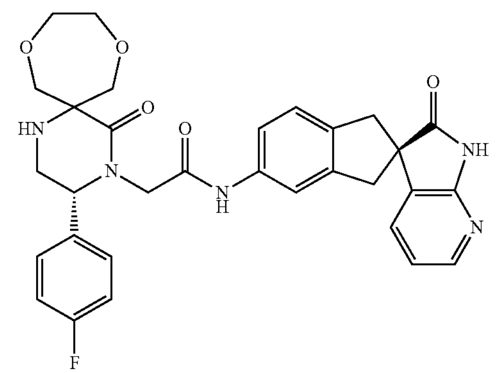 [SMILES: O=C(CN1C(=O)C2(COCCOC2)NC[C@H]1c1ccc(F)cc1)Nc1ccc2c(c1)C[C@@]1(C2)C(=O)Nc2ncccc21] |
| (23) | 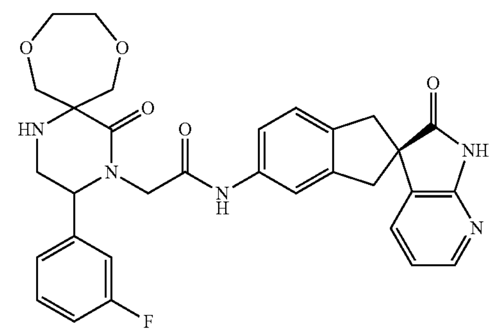 [SMILES: O=C(CN1C(=O)C2(COCCOC2)NCC1c1cccc(F)c1)Nc1ccc2c(c1)C[C@@]1(C2)C(=O)Nc2ncccc21] |
| (24) | 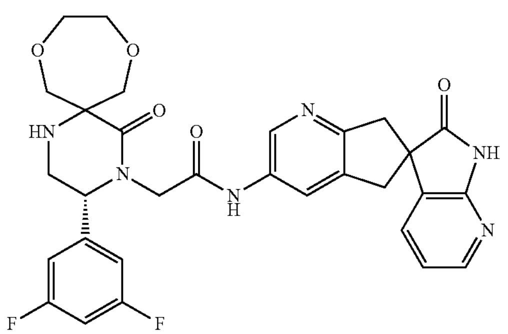 [SMILES: O=C(CN1C(=O)C2(COCCOC2)NC[C@H]1c1cc(F)cc(F)c1)Nc1cnc2c(c1)CC1(C2)C(=O)Nc2ncccc21] |
the individual diastereomers, the individual enantiomers and the salts thereof, particularly the physiologically acceptable salts thereof with inorganic or organic acids or bases.
In another aspect the present invention relates to the compounds of general formula II
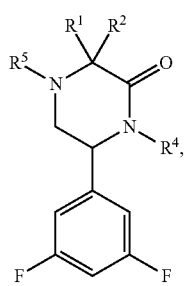
(II)
wherein
$R^1$ denotes H,
$R^2$ denotes a group selected from
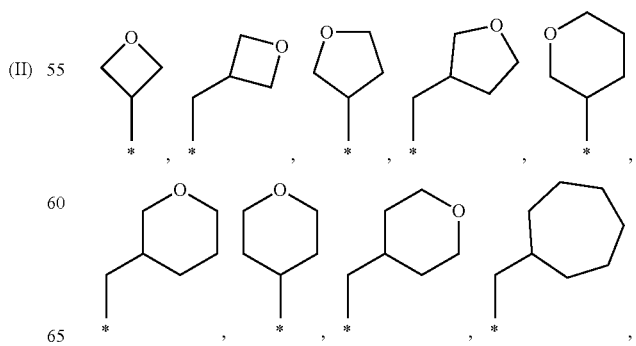

-continued

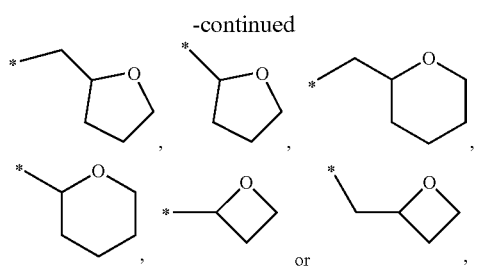

$R^4$ denotes H or $CH_2$—C(O)—$OR^{4.1}$,
$R^{4.1}$ denotes H, $C_{1-6}$-alkyl or benzyl,
$R^5$ denotes H, benzyl or —C(O)—$OR^{5.1}$,
  preferably H or —C(O)—O-tert-butyl, and
$R^{5.1}$ denotes $C_{1-6}$-alkyl or benzyl,
the individual diastereomers, the individual enantiomers and the salts thereof, particularly the physiologically acceptable salts thereof with inorganic or organic acids or bases.

In another preferred aspect the present invention relates to the compounds of general formula IIa (IIa)

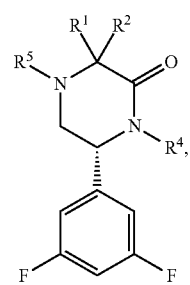

wherein
$R^1$ denotes H,
$R^2$ denotes a group selected from

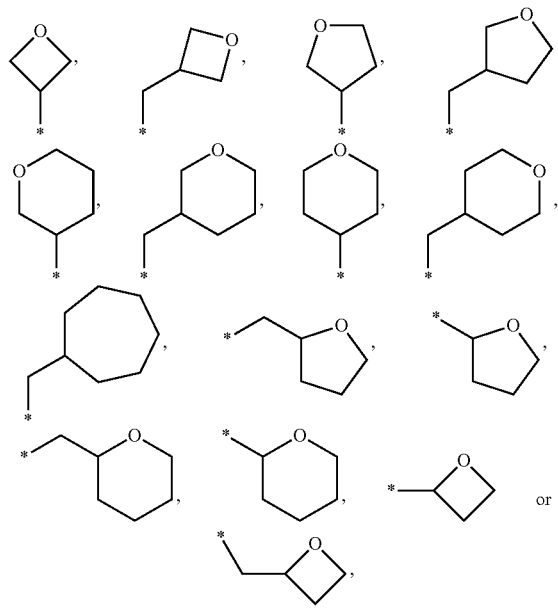

$R^4$ denotes H or —$CH_2$—C(O)—$OR^{4.1}$,
$R^{4.1}$ denotes H, $C_{1-6}$-alkyl or benzyl,
$R^5$ denotes H, benzyl or —C(O)—$OR^{5.1}$,
  preferably H or —C(O)—O-tert-butyl, and
$R^{5.1}$ denotes $C_{1-6}$-alkyl or benzyl,
the individual diastereomers, the individual enantiomers as well as the salts thereof, particularly the physiologically acceptable salts thereof with inorganic or organic acids or bases.

In another aspect the present invention relates to a process for preparing compounds of general formula II (II)

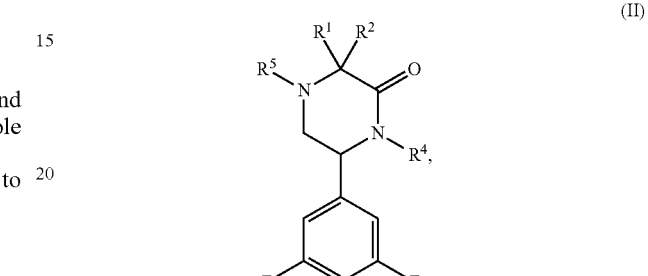

wherein
$R^1$ denotes H,
$R^2$ denotes a group selected from

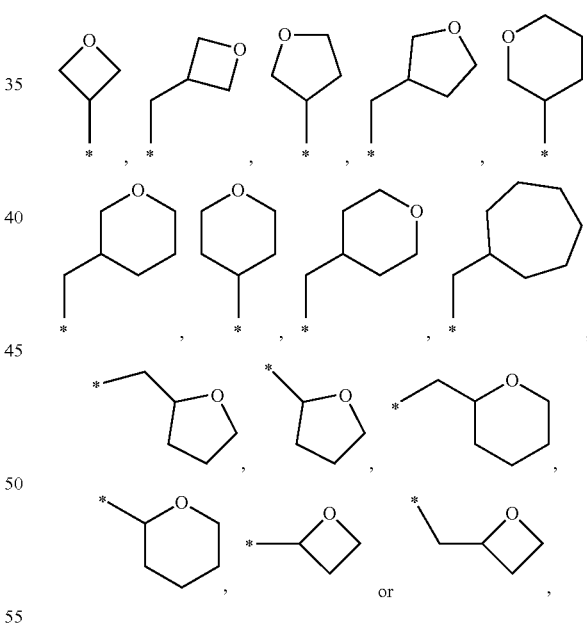

$R^4$ denotes H or —$CH_2$—C(O)—$OR^{4.1}$,
$R^{4.1}$ denotes H, $C_{1-6}$-alkyl or benzyl,
$R^5$ denotes H, benzyl or —C(O)—$OR^{5.1}$,
  preferably H or —C(O)—O-tert-butyl, and
$R^{5.1}$ denotes $C_{1-6}$-alkyl or benzyl,
the individual diastereomers, the individual enantiomers and the salts thereof, particularly the physiologically acceptable salts thereof with inorganic or organic acids or bases,
comprising the steps of:

(a) reacting a compound of general formula III

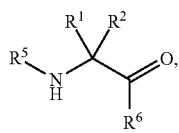
(III)

wherein $R^1$ and $R^2$ are as hereinbefore defined,
$R^5$ denotes benzyl or —C(O)—$OR^{5.1}$,
$R^{5.1}$ denotes benzyl and
$R^6$ denotes —O—$C_{1-6}$-alkyl,
with a compound of general formula IV

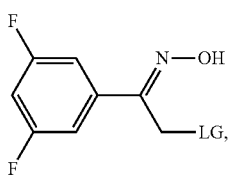
(IV)

wherein LG denotes a leaving group, for example a bromine or iodine atom, a trifluoromethanesulphonyl, methanesulphonyl or toluenesulphonyl group, preferably a bromine atom;
(b) converting a compound of general formula V

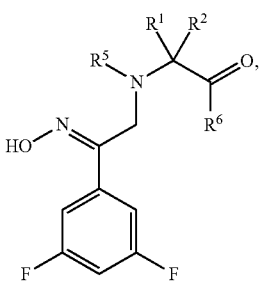
(V)

obtained in step (a), wherein $R^1$ and $R^2$ are as hereinbefore defined, $R^5$ denotes benzyl or —C(O)—O-benzyl and $R^6$ denotes the group —O—$C_{1-6}$-alkyl, under reductive conditions, such as for example in a hydrogen atmosphere at elevated pressure and temperature and in the presence of a catalyst, for example in the presence of palladium on charcoal, into a compound of general formula VI

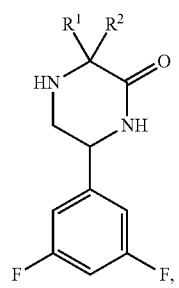
(VI)

wherein $R^1$ and $R^2$ are as hereinbefore defined;
(c) converting a compound of general formula VI obtained in step (b), into a compound of general formula VII

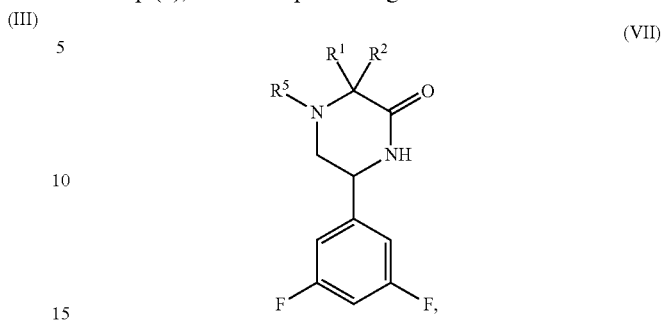
(VII)

wherein $R^1$ and $R^2$ are as hereinbefore defined,
$R^5$ denotes benzyl or —C(O)—$OR^{5.1}$ and
$R^{5.1}$ denotes $C_{1-6}$-alkyl or benzyl;
(d) reacting a compound of general formula VII obtained in step (c) with a compound of general formula VIII

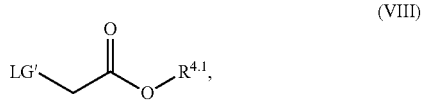
(VIII)

wherein LG' denotes a leaving group, for example a bromine or iodine atom, a trifluoromethanesulphonyl, methanesulphonyl or toluenesulphonyl group, preferably a bromine atom, and
$R^{4.1}$ denotes H, $C_{1-6}$-alkyl or benzyl; and
(e) isolating a compound of general formula II obtained in step (d), wherein $R^1$, $R^2$, $R^4$ and $R^5$ are as hereinbefore defined.

The conversion described in step (c) may be carried out using generally known methods and as described for example in T. W. Greene, P. G. M. Wuts, "Protective Groups in Organic Synthesis", Wiley, 1991 and 1999.

In another aspect the present application relates to the use of the compounds of general formula II, wherein $R^1$, $R^2$, $R^4$ and $R^5$ are as hereinbefore defined, the individual diastereomers, the individual enantiomers and the salts thereof, particularly the physiologically acceptable salts thereof with inorganic or organic acids or bases for preparing compounds of general formula I which have CGRP-antagonistic properties.

In another aspect the present application relates to the compounds of general formula IV, wherein LG is defined as mentioned hereinbefore, and their use as components for preparing compounds of general formula II.

In another aspect the present application relates to the compounds of general formula IX

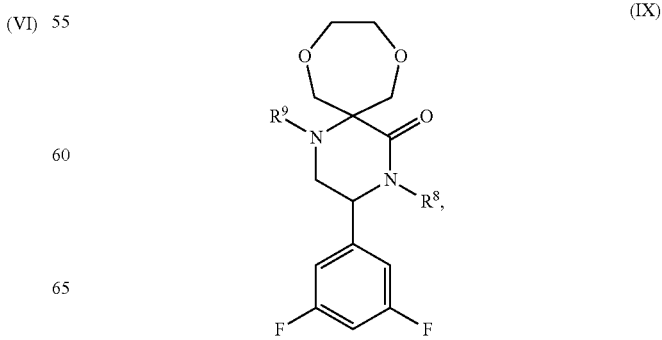
(IX)

wherein
R$^8$ denotes H or —CH$_2$—C(O)—O—R$^{8.1}$,
R$^{8.1}$ denotes H, C$_{1-6}$-alkyl or benzyl and
R$^9$ denotes H, benzyl, benzyl-O—C(O)— or C$_{1-6}$-alkyl-O—C(O)—,
the individual diastereomers, the individual enantiomers and the salts thereof, particularly the physiologically acceptable salts thereof with inorganic or organic acids or bases.

In another preferred aspect the present invention relates to the compounds of general formula IXa

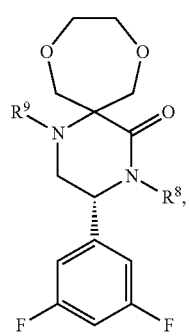

(IXa)

wherein
R$^8$ denotes H or —CH$_2$—C(O)—O—R$^{8.1}$,
R$^{8.1}$ denotes H, C$_{1-6}$-alkyl or benzyl and
R$^9$ denotes H, benzyl, benzyl-O—C(O)— or C$_{1-6}$-alkyl-O—C(O)—,
the individual diastereomers, the individual enantiomers as well as the salts thereof, particularly the physiologically acceptable salts thereof with inorganic or organic acids or bases.

In another aspect the present application relates to a process for preparing compounds of general formula IX,

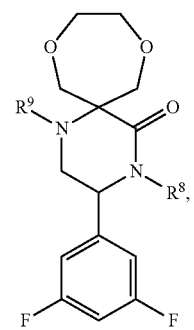

(IX)

wherein
R$^8$ denotes H or —CH$_2$—C(O)—O—R$^{8.1}$,
R$^{8.1}$ denotes H, C$_{1-6}$-alkyl or benzyl and
R$^9$ denotes H, benzyl, benzyl-O—C(O)— or C$_{1-6}$-alkyl-O—C(O)—,
the individual diastereomers, the individual enantiomers and the salts thereof, particularly the physiologically acceptable salts thereof with inorganic or organic acids or bases, comprising the steps of:

(a) reacting a compound of general formula X

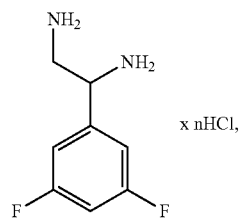

(X)

wherein n denotes one of the numbers 0, 1 or 2, with [1,4]dioxepan-6-one in the presence of a phase transfer catalyst, such as for example benzyltriethylammonium chloride, as well as in the presence of chloroform and sodium hydroxide solution;

(b) isolating a compound of formula XI obtained in step (a)

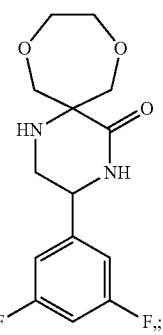

(XI)

(c) converting a compound of formula XI obtained in step (b) into a compound of general formula IX

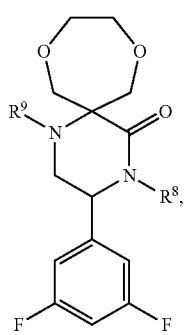

(IX)

wherein
R$^8$ denotes H and
R$^9$ denotes benzyl, benzyl-O—C(O)— or C$_{1-6}$-alkyl-O—C(O)—;

(d) reacting a compound of general formula IX obtained in step (c) with a compound of general formula VIII

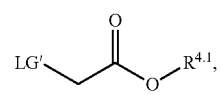

(VIII)

wherein LG' denotes a leaving group, for example a bromine or iodine atom, a trifluoromethanesulphonyl, methanesulphonyl or toluenesulphonyl group, preferably a bromine atom and $R^{4.1}$ denotes H, $C_{1-6}$-alkyl or benzyl; and (e) isolating a compound of general formula IX obtained in step (d)

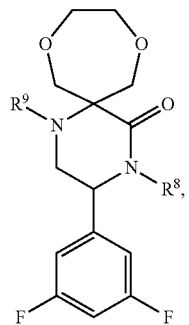

(IX)

wherein
$R^8$ denotes —$CH_2$—C(O)—O—$R^{8.1}$,
$R^{8.1}$ denotes H, $C_{1-6}$-alkyl or benzyl and
$R^9$ denotes benzyl, benzyl-O—C(O)— or $C_{1-6}$-alkyl-O—C(O)—.

The conversion described in step (c) may be carried out according to generally known methods and as described for example in T. W. Greene, P. G. M. Wuts, "Protective Groups in Organic Synthesis", Wiley, 1991 and 1999.

In another aspect the present application relates to the use of the compounds of general formula IX, wherein $R^8$ and $R^9$ are as hereinbefore defined, the individual diastereomers, the individual enantiomers and the salts thereof, particularly the physiologically acceptable salts thereof with inorganic or organic acids or bases for preparing compounds of general formula I which have CGRP-antagonistic properties.

In another aspect the present invention relates to the compounds of general formula XII

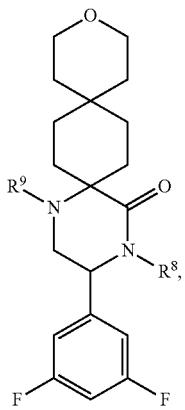

(XII)

wherein
$R^8$ denotes H or —$CH_2$—C(O)—O—$R^{8.1}$,
$R^{8.1}$ denotes H, $C_{1-6}$-alkyl or benzyl and
$R^9$ denotes H, benzyl, benzyl-O—C(O)— or $C_{1-6}$-alkyl-O—C(O)—, the individual diastereomers, the individual enantiomers and the salts thereof, particularly the physiologically acceptable salts thereof with inorganic or organic acids or bases.

In another preferred aspect the present invention relates to the compounds of general formula XIIa

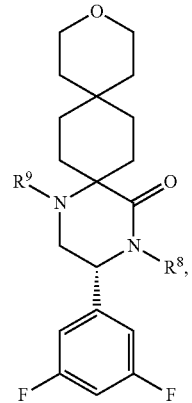

(XIIa)

wherein
$R^8$ denotes H or —$CH_2$—C(O)—O—$R^{8.1}$,
$R^{8.1}$ denotes H, $C_{1-6}$-alkyl or benzyl and
$R^9$ denotes H, benzyl, benzyl-O—C(O)— or $C_{1-6}$-alkyl-O—C(O)—, the individual diastereomers, the individual enantiomers as well as the salts thereof, particularly the physiologically acceptable salts thereof with inorganic or organic acids or bases.

In another aspect the present application relates to a process for preparing compounds of general formula XII,

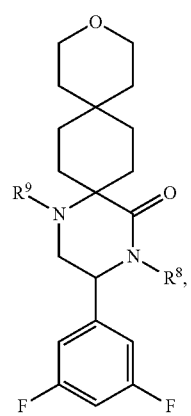

(XII)

wherein
$R^8$ denotes H or —$CH_2$—C(O)—O—$R^{8.1}$,
$R^{8.1}$ denotes H, $C_{1-6}$-alkyl or benzyl and
$R^9$ denotes H, benzyl, benzyl-O—C(O)— or $C_{1-6}$-alkyl-O—C(O)—, the individual diastereomers, the individual enantiomers and the salts thereof, particularly the physiologically acceptable salts thereof with inorganic or organic acids or bases, comprising the steps of:

(a) reacting a compound of general formula X

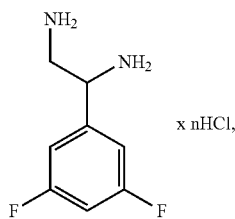

wherein n denotes one of the numbers 0, 1 or 2, with 3-oxaspiro[5.5]undecan-9-one in the presence of a phase transfer catalyst, such as for example benzyltriethylammonium chloride, as well as in the presence of chloroform and sodium hydroxide solution;

(b) isolating a compound of formula XIII obtained in step (a)

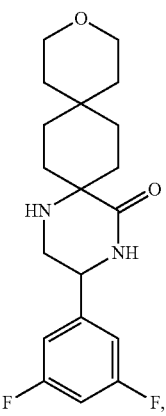

(c) converting a compound of formula XIII obtained in step (b) into a compound of general formula XII

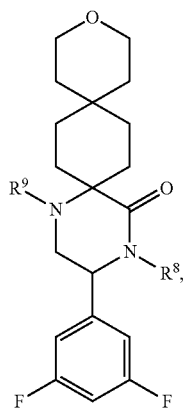

wherein
$R^8$ denotes H and
$R^9$ denotes benzyl, benzyl-O—C(O)— or $C_{1-6}$-alkyl-O—C(O)—;

(d) reacting a compound of general formula XII obtained in step (c) with a compound of general formula VIII

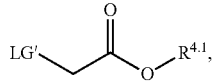

wherein LG' denotes a leaving group, for example a bromine or iodine atom, a trifluoromethanesulphonyl, methanesulphonyl or toluenesulphonyl group, preferably a bromine atom, and
$R^{4.1}$ denotes H, $C_{1-6}$-alkyl or benzyl; and (e) isolating a compound of general formula XII obtained in step (d)

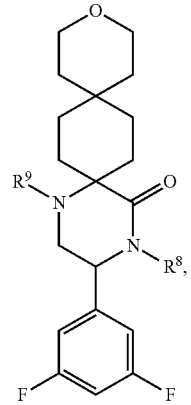

wherein
$R^8$ denotes —$CH_2$—C(O)—O—$R^{8.1}$,
$R^{8.1}$ denotes H, $C_{1-6}$-alkyl or benzyl and
$R^9$ denotes benzyl, benzyl-O—C(O)— or $C_{1-6}$-alkyl-O—C(O)—.

The conversion described in step (c) may be carried out according to generally known methods and as described for example in T. W. Greene, P. G. M. Wuts, "Protective Groups in Organic Synthesis", Wiley, 1991 and 1999.

In another aspect the present application relates to the use of the compounds of general formula XII, wherein $R^8$ and $R^9$ are as hereinbefore defined, the individual diastereomers, the individual enantiomers and the salts thereof, particularly the physiologically acceptable salts thereof with inorganic or organic acids or bases for preparing compounds of general formula I which have CGRP-antagonistic properties.

If there are ester functionalities present in compounds of general formula (II) wherein $R^1$, $R^2$, $R^4$ and $R^5$ are as hereinbefore defined, in compounds of general formula (IX) wherein $R^8$ and $R^9$ are as hereinbefore defined, and in compounds of general formula (XII) wherein $R^8$ and $R^9$ are as hereinbefore defined, these may be converted into the corresponding acid by generally known methods as described in T. W. Greene, P. G. M. Wuts, "Protective Groups in Organic Synthesis", Wiley, 1991 and 1999.

TERMS AND DEFINITIONS USED

The present description of the invention is to be interpreted in accordance with the conventions and rules of chemical bonds. The compounds encompassed by this invention are those that are also chemically stable.

Within the scope of this application, in the definition of possible substituents, these may also be represented in the form of a structural formula. If present, an asterisk (*) in the structural formula of the substituent is to be understood as being the linking point to the rest of the molecule. For example a phenyl group is shown as follows:

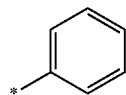 [SMILES: *c1ccccc1]

Moreover, the atom of the substituent that follows the linking point is understood as being the atom at position number 1.

The subject-matter of this invention also includes the compounds according to the invention, including the salts thereof, wherein one or more hydrogen atoms, for example one, two, three, four or five hydrogen atoms, are replaced by deuterium.

The subject-matter of this invention also includes the compounds according to the invention, including the salts thereof, wherein a carbon atom is replaced by silicon.

The subject-matter of this invention also includes the compounds according to the invention that occur as tautomers.

By the term "$C_{1-4}$-alkyl" (including those that are part of other groups) are meant branched and unbranched alkyl groups with 1, 2, 3 or 4 carbon atoms and by the term "$C_{1-6}$-alkyl" are meant branched and unbranched alkyl groups with 1, 2, 3, 4, 5 or 6 carbon atoms. Examples include: methyl, ethyl, n-propyl, iso-propyl, n-butyl, iso-butyl, sec-butyl, tert-butyl, pentyl, neopentyl or n-hexyl. The abbreviations Me, Et, n-Pr, i-Pr, n-Bu, i-Bu, t-Bu, etc. may optionally also be used for the above-mentioned groups. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_1$-alkylene" (including those that are part of other groups) is meant a methylene group with a carbon atom. The definition for $C_0$-alkylene denotes a bond.

By the term "$C_{4-6}$-cycloalkyl" (including those that are part of other groups) are meant cyclic alkyl groups with 4, 5 or 6 carbon atoms. Examples include: cyclobutyl, cyclopentyl or cyclohexyl.

Compounds of general formula I may have acidic and/or basic groups. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali metal alkoxides or alkaline earth metal hydroxides, for example sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine and dicyclohexylamine, inter alia.

The compounds according to the invention may occur as racemates if they have only one chiral element, but they may also be obtained as pure enantiomers, i.e. in the (R)- or (S)-form.

The application also, however, includes the individual diastereomeric pairs of antipodes or the mixtures thereof which are present when more than one chiral element is present in the compounds of general formula I, as well as the individual optically active enantiomers of which the above-mentioned racemates are made up.

The invention relates to the respective compounds optionally in the form of the individual optical isomers, mixtures of the individual enantiomers or racemates, in the form of the tautomers as well as in the form of the free bases or the corresponding acid addition salts with pharmacologically acceptable acids.

So-called prodrugs of compounds of general formula I are also encompassed by this invention. The term prodrug is used to denote any molecule that releases the active principle of general formula I in-vivo after administration to mammals. The prodrug may have little or no pharmacological activity per se, but releases the active principle of general formula I in-vivo after administration and this has the activity described. Prodrugs for compounds of general formula I may be prepared by modifying suitable functional groups in the compound of general formula I, as known to the skilled man in this field. (H. Bundgaard (Editor), Design of Prodrugs (1986), Elsevier).

This invention also includes those metabolites that are derived from compounds of general formula I. By metabolites are meant, in this context, compounds that are formed in-vivo from the compound of general formula I after administration. Examples of metabolites include:

secondary amines of the compound of general formula I may be converted into the corresponding primary amines. (—$NR_1R_2$→—$NHR_1$ or —$NHR_2$)

nitrogen atoms of the compound of general formula I may be converted into the corresponding nitrogen oxides. (=N—→=$N^+$—($O^-$)—)

Methods of Preparation

The invention further relates to a process for preparing the compounds of general formula I

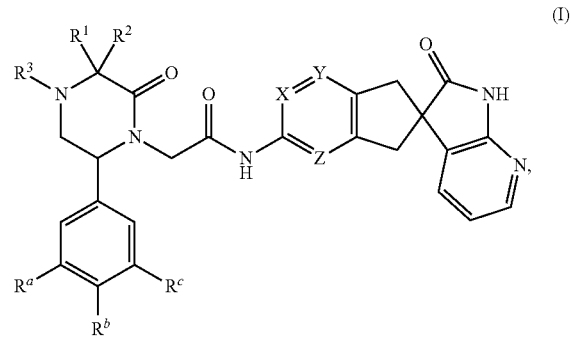

wherein X, Y, Z, $R^1$, $R^2$, $R^3$, $R^a$, $R^b$ and $R^c$ are defined as mentioned hereinbefore.

Some methods of preparing the novel compounds of general formula I and their precursors are illustrated in the following synthesis schemes and Examples.

In some cases the order of carrying out the reaction schemes may be varied in order to simplify the reactions or prevent unwanted by-products. The Examples that follow are provided to make the invention fully comprehensible. The Examples are intended to illustrate the invention and should in no way restrict it.

The compounds according to the invention and their intermediates may be prepared according to the schemes and specific examples provided or corresponding modifications thereof. Modifications to these reactions which are known to the skilled man but not described in detail here may also be implemented. The general methods of preparing the compounds according to the invention will become apparent to the skilled man from a study of the following schemes.

Starting compounds are commercially available or are prepared by processes which are described in the literature, known in the art or as described herein. Before the reaction is carried out corresponding functional groups in the compounds may be protected by conventional protective groups. These protective groups may be cleaved again at a suitable stage within the reaction sequence using methods familiar to the skilled man.

In the reactions described below, any reactive groups present such as hydroxy-, carboxy-, amino-, alkylamino-, amide- or imino groups may be protected during the reaction by conventional protective groups that are cleaved again after the reaction.

For example
suitable protective groups for a carboxyl group may be the trimethylsilyl-, methyl-, ethyl-, tert.-butyl-, benzyl- or tetrahydropyranyl-group, and
suitable protective groups for an amide group may be the N-methoxymethyl- (MOM), N-benzyloxymethyl- (BOM), N-(trimethylsilyl)ethoxymethyl- (SEM), N-tert-butyldimethylsiloxymethyl-, N-tert-butyldimethylsilyl- (TBDMS), N-triisopropylsilyl- (TIPS), N-benzyl-, N-4-methoxybenzyl- (PMB), N-triphenylmethyl- (Tr), N-tert-butoxycarbonyl- (BOC), N-benzyloxycarbonyl- (Cbz) or N-trimethylsilylethylsulphonyl- (SES)
a suitable protective group for an amino, alkylamino or imino group may be the acetyl-, trifluoroacetyl-, benzoyl-, ethoxycarbonyl-, tert.-butoxycarbonyl-, benzyloxycarbonyl-, benzyl, methoxybenzyl- or 2,4-dimethoxybenzyl group and additionally, for the amino-group, the phthalyl group.

Other protective groups and their cleavage are described in T. W. Greene, P. G. M. Wuts, "Protective Groups in Organic Synthesis", Wiley, 1991 and 1999.

A general method of synthesising piperazinones of general formula (1-5), wherein $R^1$ and $R^2$ are defined as mentioned hereinbefore, is illustrated in Scheme 1a.

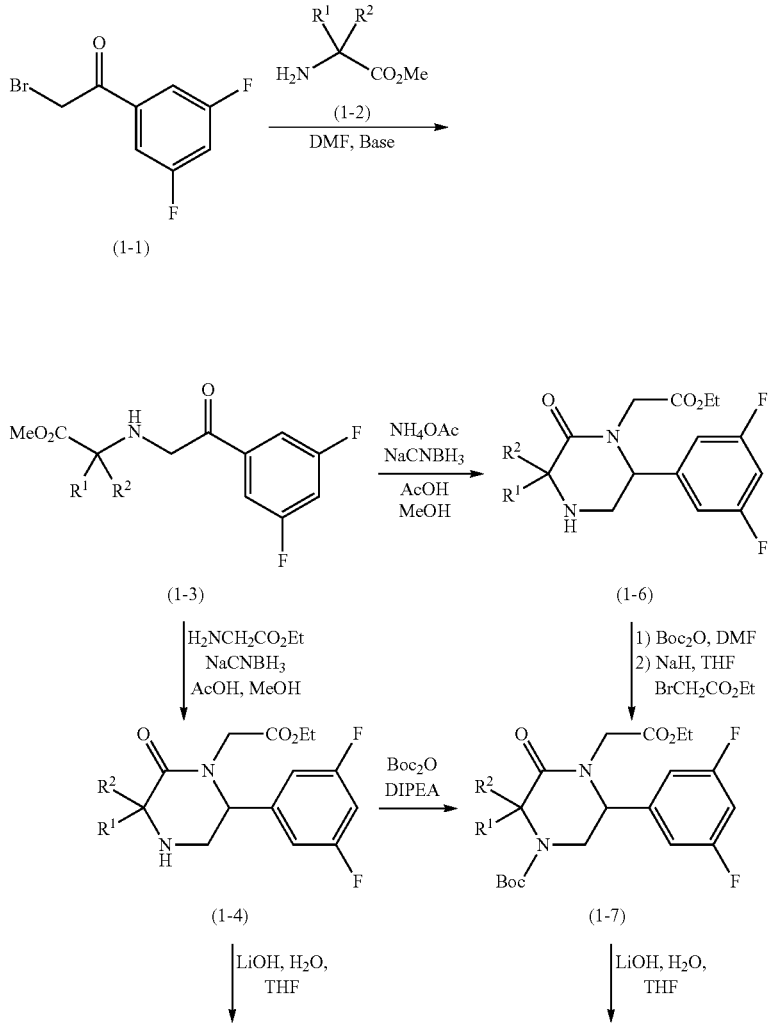

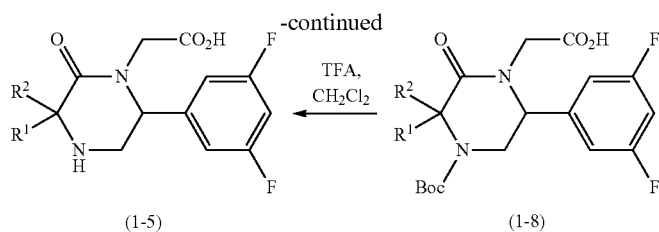

Reacting 2-bromo-1-(3,5-difluoro-phenyl)-ethanone (1-1) with an α-aminoester of general formula (1-2), wherein $R^1$ and $R^2$ are defined as mentioned hereinbefore, yields the aminoketone of general formula (1-3), wherein $R^1$ and $R^2$ are defined as mentioned hereinbefore. Various bases may be used for this reaction, such as for example $NaHCO_3$, $K_2CO_3$ and $Na_3PO_4$. Reductive amination of the aminoketone (1-3) with glycine ethyl ester under suitable reaction conditions yields the piperazinone of general formula (1-4), wherein $R^1$ and $R^2$ are defined as mentioned hereinbefore. Esters of general formula (1-4), wherein $R^1$ and $R^2$ are defined as mentioned hereinbefore, may be converted into the acid of general formula (1-5), wherein $R^1$ and $R^2$ are as hereinbefore defined, by basic or acidic hydrolysis (J. March, Advanced Organic Chemistry (New York: J. Wiley and Sons, 1985) or by reaction with alkali metal salts (preferably LiI or NaCN) in an inert solvent. Inert solvents may be dialkylformamide (particularly preferably N,N-dimethylformamide), dialkylacetamide (particularly preferably N,N-dimethylacetamide), cyclic amide (particularly preferably N-methylpyrrolidone). It is particularly preferable to carry out alkaline saponification with alkali metal hydroxides such as sodium hydroxide or lithium hydroxide in inert solvents. Suitable inert solvents are water and cyclic ethers such as 1,4-dioxane or tetrahydrofuran as well as solvent mixtures.

Alternatively the aminoketone of general formula (1-3) may be converted, in a reductive amination with ammonium acetate, into the corresponding diamine, which is cyclised immediately under suitable test conditions to form the piperazinone of general formula (1-6), wherein $R^1$ and $R^2$ are defined as mentioned hereinbefore. The piperazinone of general formula (1-6) may be reacted under suitable reaction conditions first of all to form the corresponding tert-butylcarbamate and then with ethyl bromoacetate to form the ester of general formula (1-7), wherein $R^1$ and $R^2$ are defined as mentioned hereinbefore. Alternatively compounds of general formula (1-7), wherein $R^1$ and $R^2$ are defined as mentioned hereinbefore, may be prepared from compounds of general formula (1-4), wherein $R^1$ and $R^2$ are defined as mentioned hereinbefore, with di-tert-butyldicarbonate and a base, such as for example diisopropylethylamine, in a suitable solvent. The saponification of the ester (1-7) to form the corresponding acid of general formula (1-8), wherein $R^1$ and $R^2$ are defined as mentioned hereinbefore, may be carried out as described hereinbefore. It is particularly preferable to use alkali metal hydroxides such as lithium hydroxide in a mixture of water and tetrahydrofuran.

The Boc-protective group of the acid of general formula (1-8) may be cleaved under suitable conditions as described for example in T. W. Greene, P. G. M. Wuts, "Protective Groups in Organic Synthesis", Wiley, 1991 and 1999. Preferably, trifluoroacetic acid is used in dichloromethane at ambient temperature under normal pressure. After the deprotection the acid of general formula (1-5) is obtained, wherein $R^1$ and $R^2$ are defined as mentioned hereinbefore.

Scheme 1b:

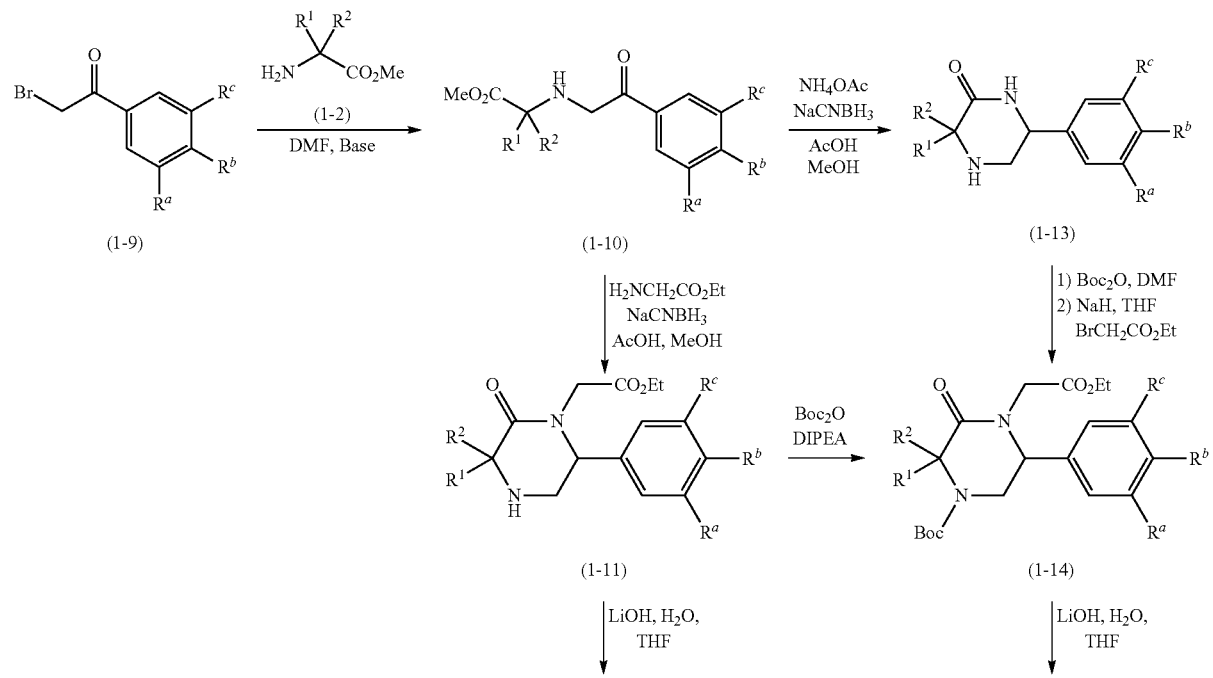

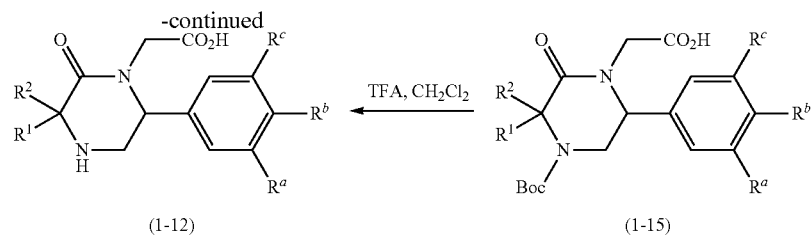

As shown in Scheme 1b, compounds of general formula (1-12) wherein $R^1$, $R^2$, $R^a$, $R^b$ and $R^c$ are defined as mentioned hereinbefore may be synthesised analogously to Scheme 1a:

Reacting 2-bromo-1-(3,5-difluoro-phenyl)-ethanone (1-9) with an α-aminoester of general formula (1-2), wherein $R^1$ and $R^2$ are defined as mentioned hereinbefore, yields the aminoketone of general formula (1-10), wherein $R^1$, $R^2$, $R^a$, $R^b$ and $R^c$ are defined as mentioned hereinbefore. Various bases may be used for this reaction, for example $NaHCO_3$, $K_2CO_3$ and $Na_3PO_4$. Reductive amination of the aminoketone (1-10) with glycinethylester under suitable reaction conditions yields the piperazinone of general formula (1-11), wherein $R^1$, $R^2$, $R^a$, $R^b$ and $R^c$ are defined as mentioned hereinbefore. Esters of general formula (1-11), wherein $R^1$, $R^2$, $R^a$, $R^b$ and $R^c$ are defined as mentioned hereinbefore, may be converted into the acid of general formula (1-12), wherein $R^1$, $R^2$, $R^a$, $R^b$ and $R^c$ are as hereinbefore defined, by basic or acidic hydrolysis (J. March, Advanced Organic Chemistry (New York: J. Wiley and Sons, 1985) or by reaction with alkali metal salts (preferably LiI or NaCN) in an inert solvent. Inert solvents may be dialkylformamides (particularly preferably N,N-dimethylformamide), dialkylacetamides (particularly preferably N,N-dimethylacetamide), cyclic amides (particularly preferably N-methylpyrrolidone). It is particularly preferable to carry out alkaline saponification with alkali metal hydroxides such as sodium hydroxide or lithium hydroxide in inert solvents. Suitable inert solvents are water and cyclic ethers such as 1,4-dioxane or tetrahydrofuran as well as solvent mixtures.

Alternatively the aminoketone of general formula (1-10) may be converted, in a reductive amination with ammonium acetate, into the corresponding diamine, which is cyclised immediately under suitable test conditions to form the piperazinone of general formula (1-13), wherein $R^1$, $R^2$, $R^a$, $R^b$ and $R^c$ are defined as mentioned hereinbefore. The piperazinone of general formula (1-13) may be reacted under suitable reaction conditions first of all to form the corresponding tert-butylcarbamate and then with ethyl bromoacetate to form the ester of general formula (1-14), wherein $R^1$, $R^2$, $R^a$, $R^b$ and $R^c$ are defined as mentioned hereinbefore. Alternatively compounds of general formula (1-14), wherein $R^1$, $R^2$, $R^a$, $R^b$ and $R^c$ are defined as mentioned hereinbefore, may be prepared from compounds of general formula (1-11), wherein $R^1$, $R^2$, $R^a$, $R^b$ and $R^c$ are defined as mentioned hereinbefore, with di-tert-butyldicarbonate and a base, such as for example diisopropylethylamine, in a suitable solvent. The saponification of the ester (1-14) to form the corresponding acid of general formula (1-15), wherein $R^1$, $R^2$, $R^a$, $R^b$ and $R^c$ are defined as mentioned hereinbefore, may be carried out as described hereinbefore. It is particularly preferable to use alkali metal hydroxides such as lithium hydroxide in a mixture of water and tetrahydrofuran.

The Boc-protective group of the acid of general formula (1-15) may be cleaved under suitable conditions as described for example in T. W. Greene, P. G. M. Wuts, "Protective Groups in Organic Synthesis", Wiley, 1991 and 1999. Preferably, trifluoroacetic acid is used in dichloromethane at ambient temperature under normal pressure. After the deprotection the acid of general formula (1-12) is obtained, wherein $R^1$, $R^2$, $R^a$, $R^b$ and $R^c$ are defined as mentioned hereinbefore.

Compounds of general formula (2-5), wherein X, Y, Z, and $R^2$ are defined as mentioned hereinbefore, may be prepared as shown in Scheme 2a.

Scheme 2a:

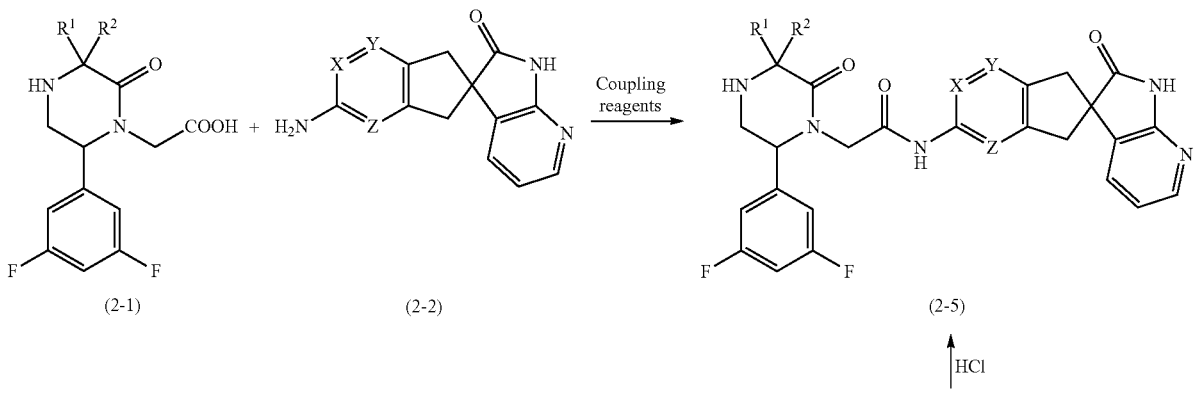

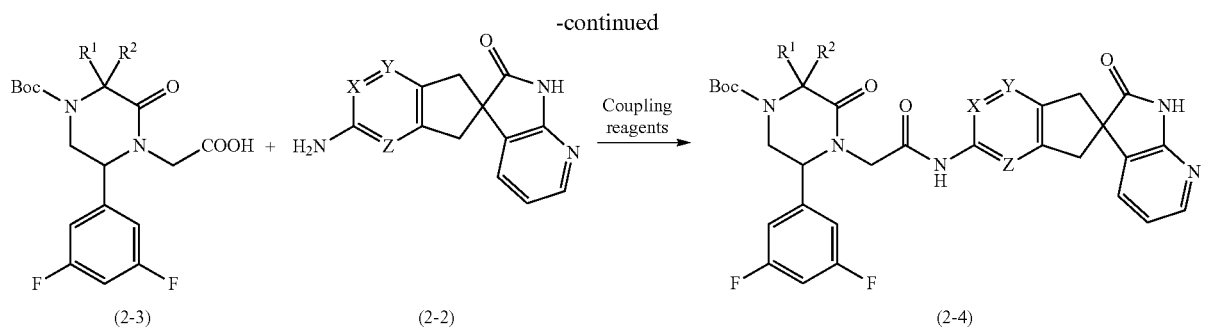

Carboxylic acids of general formula (2-1), wherein $R^1$ and $R^2$ are defined as mentioned hereinbefore, may be reacted with the aid of standard peptide coupling reagents and a base in an inert solvent with amines of general formula (2-2), wherein X, Y and Z are defined as mentioned hereinbefore, to form amides of general formula (2-5), wherein X, Y, Z, and $R^2$ are defined as mentioned hereinbefore (cf. e.g. Houben-Weyl, Methoden der Organischen Chemie, vol. 15/2). Inert solvents that may be used are dimethylformamide, N-methylpyrrolidone, dimethoxyethane, dichloromethane, acetonitrile or solvent mixtures. The preferred solvent is dimethylformamide. Suitable bases are particularly amine bases such as e.g. triethylamine or diisopropylethylamine. Coupling reagents that may be used are for example 1H-benzotriazol-1-yl-oxy-tripyrrolidino-phosphonium-hexafluorophosphate (PyBOP), dicyclohexylcarbodiimide (DCC), diisopropylcarbodiimide (DIC), ethyl-(3-dimethylamino-propyl)-carbodiimide (EDC), O-(1H-benzotriazol-1-yl)-N,N—N,N-tetramethyl-uronium hexafluorophosphate (HBTU) or -tetrafluoroborate (TBTU) or 1H-benzotriazol-1-yl-oxy-tris-(dimethylamino)-phosphonium-hexafluorophosphate (BOP). Particularly preferred is the use of EDC. Moreover 1-hydroxybenzotriazole (HOBt) may be added to the reaction mixture. The activation of the carboxyl group may also be carried out via a corresponding acid anhydride or acid chloride. The reaction is generally carried out in a temperature range from −20° C. to the reflux temperature of the solvent at under normal pressure. Particularly preferred is the use of diisopropylethylamine as base and dimethylformamide as solvent. Analogously, compounds of general formula (2-5), wherein X, Y, Z, $R^1$ and $R^2$ are defined as mentioned hereinbefore, may be synthesised from the corresponding carboxylic acids of general formula (2-3), wherein $R^1$ and $R^2$ are defined as mentioned hereinbefore, and amines of general formula (2-2), wherein X, Y and Z are defined as mentioned hereinbefore. For this, the corresponding amides of general formula (2-4), wherein X, Y, Z, $R^1$ and $R^2$ are defined as mentioned hereinbefore, must be deprotected accordingly. The Boc protective group is eliminated using methods known from the literature, such as for example with HCl in a suitable solvent.

In some cases the end product may be further derivatised, e.g. by manipulation of the substituents. These manipulations may be, inter alia, those that are generally known in the art, such as oxidation, reduction, alkylation, acylation and hydrolysis, but need not necessary be restricted to these.

Analogously to Scheme 2a, compounds of general formula (2-8), wherein X, Y, Z, $R^1$, $R^2$, $R^3$, $R^a$, $R^b$ and $R^c$ are defined as mentioned hereinbefore, may be prepared as shown in Scheme 2b.

Scheme 2b:

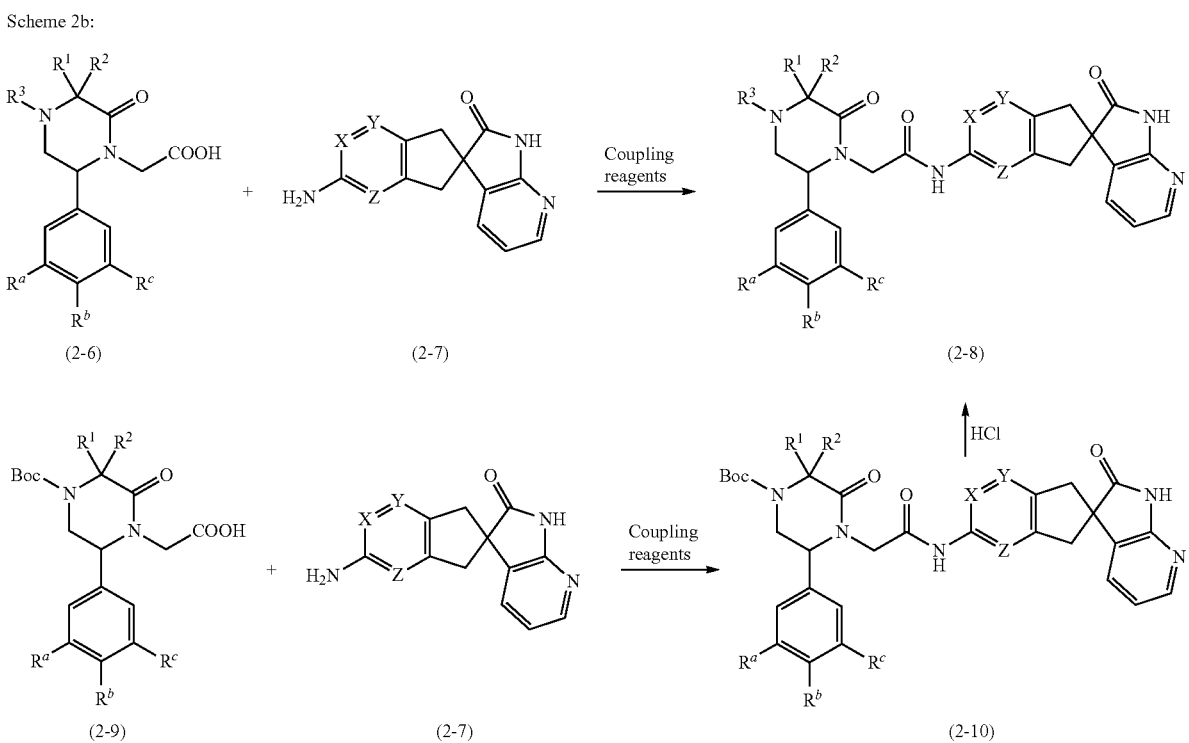

Carboxylic acids of general formula (2-6), wherein $R^1$, $R^2$, $R^3$, $R^a$, $R^b$ and $R^c$ are defined as mentioned hereinbefore, may be reacted with the aid of standard peptide coupling reagents and a base in an inert solvent with amines of general formula (2-7), wherein X, Y and Z are defined as mentioned hereinbefore, to form amides of general formula (2-8), wherein X, Y, Z, $R^1$, $R^2$, $R^3$, $R^a$, $R^b$ and $R^c$ are defined as mentioned hereinbefore (cf. e.g. Houben-Weyl, Methoden der Organischen Chemie, vol. 15/2). Inert solvents that may be used are dimethylformamide, N-methylpyrrolidone, dimethoxyethane, dichloromethane, acetonitrile or solvent mixtures. The preferred solvent is dimethylformamide. Suitable bases are particularly amine bases such as e.g. triethylamine or diisopropylethylamine. Coupling reagents that may be used are for example 1H-benzotriazol-1-yl-oxy-tripyrrolidino-phosphonium-hexafluorophosphate (PyBOP), dicyclohexylcarbodiimide (DCC), diisopropylcarbodiimide (DIC), ethyl-(3-dimethylamino-propyl)-carbodiimide (EDC), O-(1H-benzotriazol-1-yl)-N,N—N,N-tetramethyl-uronium hexafluorophosphate (HBTU) or -tetrafluoroborate (TBTU) or 1H-benzotriazol-1-yl-oxy-tris-(dimethylamino)-phosphonium-hexafluorophosphate (BOP). Particularly preferred is the use of EDC. Moreover 1-hydroxybenzotriazole (HOBt) may be added to the reaction mixture. The activation of the carboxyl group may also be carried out via a corresponding acid anhydride or acid chloride. The reaction is generally carried out in a temperature range from −20° C. to the reflux temperature of the solvent under normal pressure. Particularly preferred is the use of diisopropylethylamine as base and dimethylformamide as solvent. Analogously, compounds of general formula (2-8), wherein X, Y, Z, $R^1$, $R^2$, $R^a$, $R^b$ and $R^c$ are defined as mentioned hereinbefore and $R^3$ denotes a hydrogen atom, may be synthesised from the corresponding carboxylic acids of general formula (2-9), wherein $R^1$, $R^2$, $R^a$, $R^b$ and $R^c$ are defined as mentioned hereinbefore, and amines of general formula (2-7), wherein X, Y and Z are defined as mentioned hereinbefore. For this, the corresponding amides of general formula (2-10), wherein X, Y, Z, $R^1$, $R^2$, $R^a$, $R^b$ and $R^c$ are defined as mentioned hereinbefore, must be deprotected accordingly. The Boc protective group is eliminated using methods known from the literature, such as for example with HCl in a suitable solvent.

The α-aminoesters used as intermediates are synthesised using methods known in the art or described in the literature. By way of example, the synthesis of α-aminoesters is described in Scheme 3 and Scheme 4. The processes described therein are intended purely as an illustration and are not restricted thereto.

Scheme 3:

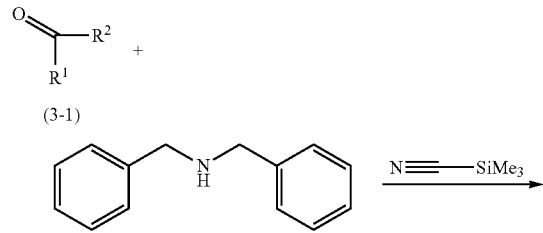

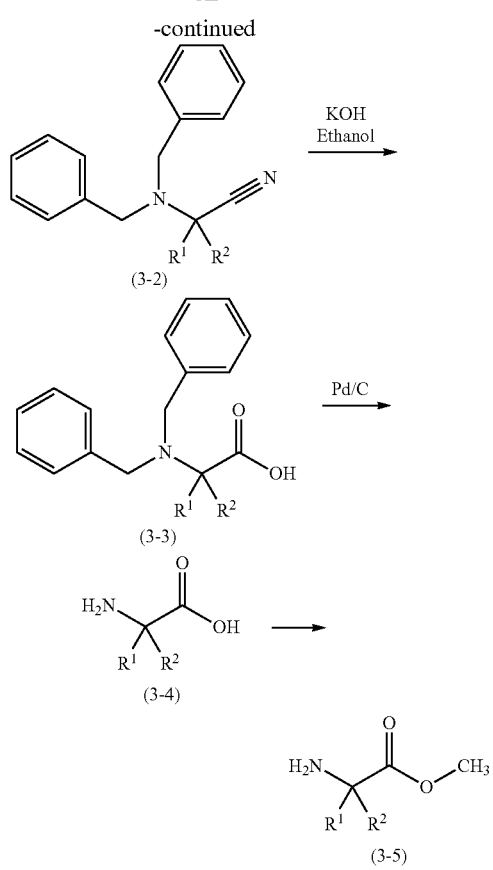

Ketones of general formula (3-1), wherein $R^1$ and $R^2$ are defined as mentioned hereinbefore, may be reacted with dibenzylamine and trimethylsilylcyanide in a suitable solvent such as acetic acid to form the corresponding nitriles of general formula (3-2), wherein $R^1$ and $R^2$ are defined as mentioned hereinbefore. Nitriles of general formula (3-2) may be reacted with sodium hydroxide in a suitable solvent such as for example in ethanol to form the corresponding acid of general formula (3-3), wherein $R^1$ and $R^2$ are defined as mentioned hereinbefore. The cleaving of the benzyl protecting groups is carried out for example by hydrogenolysis, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0° C. and 50° C., but preferably at ambient temperature, and under a hydrogen pressure of 1 to 7 bar, but preferably 1 to 5 bar. After the cleaving of the benzyl protecting group an amino acid of general formula (3-4) is obtained wherein $R^1$ and $R^2$ are defined as mentioned hereinbefore. The amino acid of general formula (3-4) may be converted by generally known methods and as described for example in T. W. Greene, P. G. M. Wuts, "Protective Groups in Organic Synthesis", Wiley, 1991 and 1999, into the corresponding α-aminoester of general formula (3-5), wherein $R^1$ and $R^2$ are defined as mentioned hereinbefore.

As shown in Scheme 4, α-aminoesters of general formula (4-4), wherein $R^1$ is as hereinbefore defined and $R^2$ preferably denotes a hydrogen atom, may also be synthesised using the Schökopf-Hartwig method.

Scheme 4:

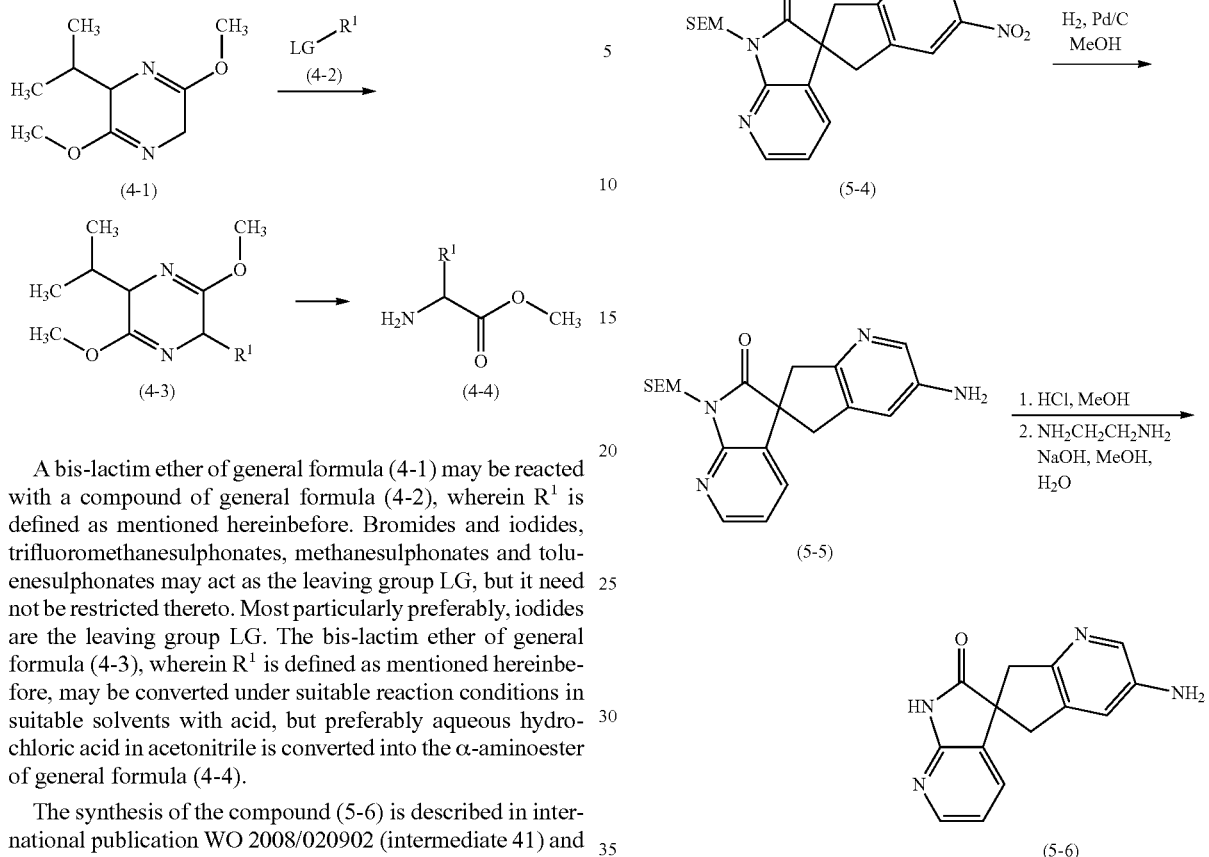

A bis-lactim ether of general formula (4-1) may be reacted with a compound of general formula (4-2), wherein $R^1$ is defined as mentioned hereinbefore. Bromides and iodides, trifluoromethanesulphonates, methanesulphonates and toluenesulphonates may act as the leaving group LG, but it need not be restricted thereto. Most particularly preferably, iodides are the leaving group LG. The bis-lactim ether of general formula (4-3), wherein $R^1$ is defined as mentioned hereinbefore, may be converted under suitable reaction conditions in suitable solvents with acid, but preferably aqueous hydrochloric acid in acetonitrile is converted into the α-aminoester of general formula (4-4).

The synthesis of the compound (5-6) is described in international publication WO 2008/020902 (intermediate 41) and shown here in Scheme 5:

Scheme 5:

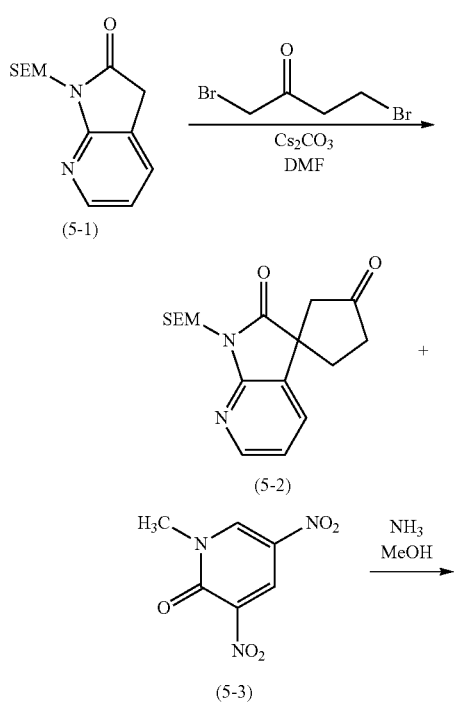

The synthesis of compound (6-5) is described in international publication WO 2008/020902 (intermediate 42) and shown here in Scheme 6:

Scheme 6:

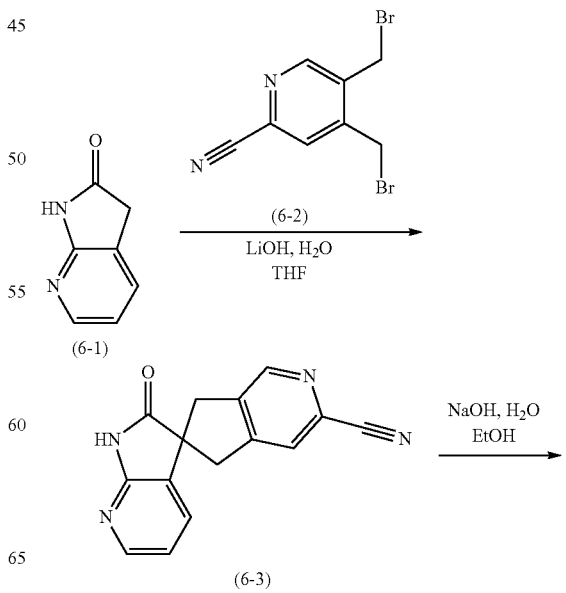

-continued

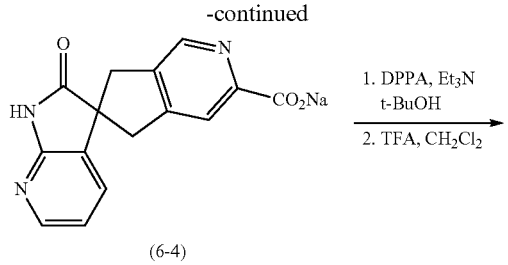

(6-4)

1. DPPA, Et₃N
   t-BuOH
2. TFA, CH₂Cl₂

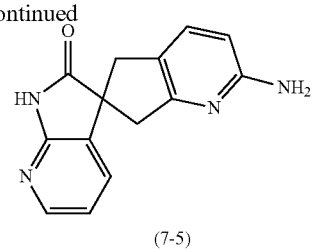

(7-5)

Compounds of general formula (8-3), wherein $m^1$ denotes one of the numbers 1 or 2, $m^2$ denotes one of the numbers 1 or 2, $n^3$ denotes one of the numbers 0 or 1 and $n^2$ denotes one of the numbers 1 or 2, may be prepared as shown in Scheme 8. Synthesis is carried out analogously to US 2005/0261501.

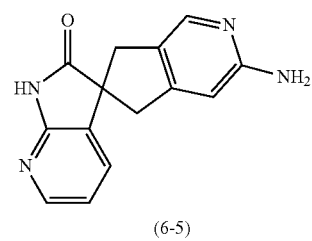

(6-5)

Scheme 8:

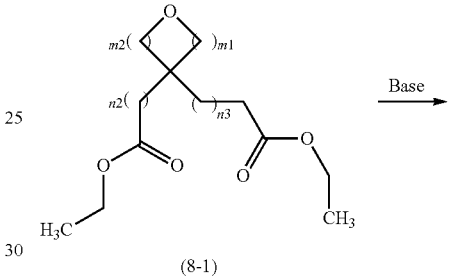

(8-1)

Base →

The synthesis of compound (7-5) is described in international publication WO 2008/020902 (intermediate 43) and shown here in Scheme 7:

Scheme 7:

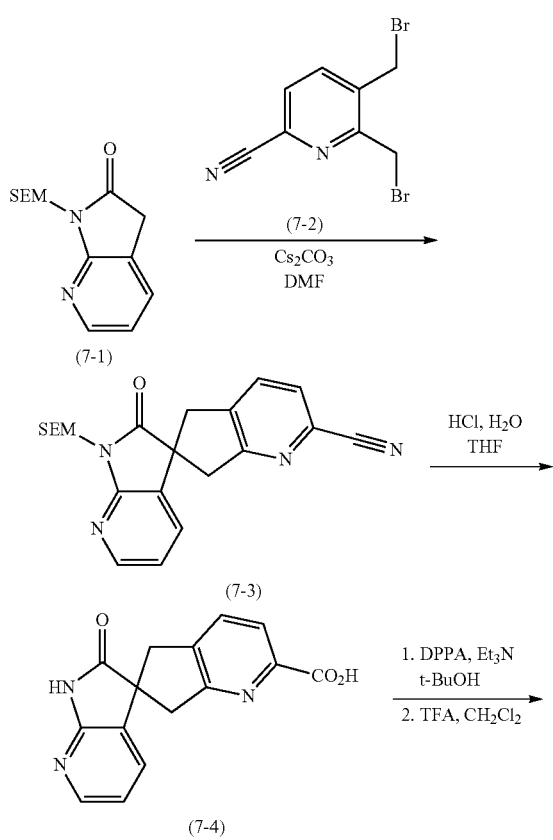

A compound of general formula (8-1), wherein $m^1$ denotes one of the numbers 1 or 2, $m^2$ denotes one of the numbers 1 or 2, $n^3$ denotes one of the numbers 0 or 1 and $n^2$ denotes one of the numbers 1 or 2, may be deprotonated with a base, such as for example sodium hydride or sodium ethoxide, and in a suitable solvent, such as for example tetrahydrofuran, and then cyclised to form a compound of general formula (8-2), wherein $m^1$ denotes one of the numbers 1 or 2, $m^2$ denotes one of the numbers 1 or 2, $n^3$ denotes one of the numbers 0 or 1 and $n^2$ denotes one of the numbers 1 or 2. The ester group may first of all be saponified under suitable conditions, for example with HCl in ethanol, and then decarboxylated, in order to obtain the compound of general formula (8-3), wherein $m^1$ denotes one of the numbers 1 or 2, $m^2$ denotes one of the numbers 1 or 2, $n^3$ denotes one of the numbers 0 or 1 and $n^2$ denotes one of the numbers 1 or 2.

Compounds of general formula (9-3), wherein $m^1$ denotes one of the numbers 1 or 2 and $m^2$ denotes one of the numbers 1 or 2, may be prepared as shown in Scheme 9. Synthesis is carried out analogously to US 2005/0261501.

Scheme 9:

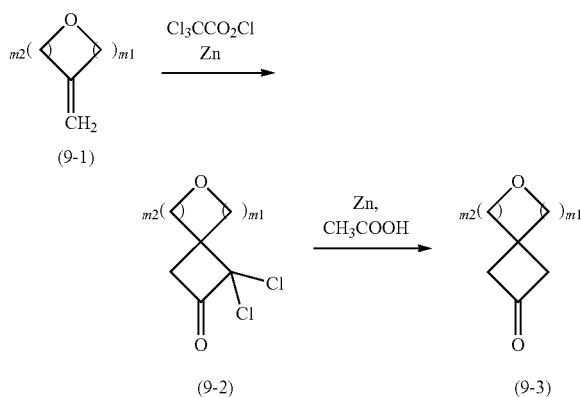

Compounds of general formula (9-1), wherein m¹ denotes one of the numbers 1 or 2 and m² denotes one of the numbers 1 or 2, may be reacted with zinc and trichloroacetic acid chloride in a suitable solvent, such as for example in diethyl ether. Optionally the reaction is carried out under ultrasound. Compounds of general formula (9-2), wherein m¹ denotes one of the numbers 1 or 2 and m² denotes one of the numbers 1 or 2, may optionally be converted in a suitable solvent, such as for example water with acetic acid and zinc powder, into compounds of general formula (9-3), wherein m¹ denotes one of the numbers 1 or 2 and m² denotes one of the numbers 1 or 2.

Compounds of general formula (10-3), wherein m¹ denotes one of the numbers 1 or 2 and m² denotes one of the numbers 1 or 2, may be prepared as shown in Scheme 10. Synthesis is carried out analogously to US 2005/0261501.

Scheme 10:

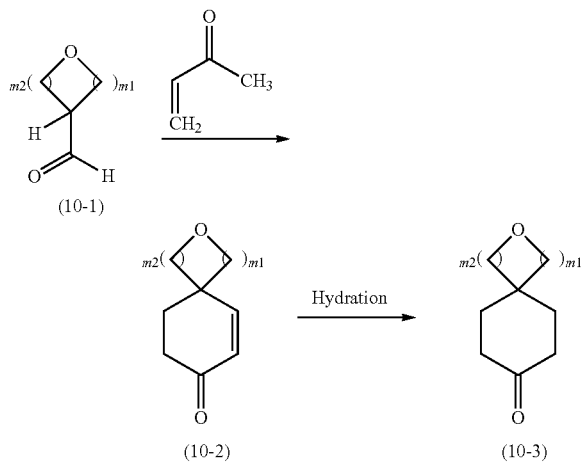

Compounds of general formula (10-1), wherein m¹ denotes one of the numbers 1 or 2 and m² denotes one of the numbers 1 or 2, are reacted in a suitable solvent with methylvinylketone in a Michael reaction and a subsequent intramolecular aldol reaction to obtain the cyclohexenone derivative of general formula (10-2), wherein m¹ denotes one of the numbers 1 or 2 and m² denotes one of the numbers 1 or 2. The reactions may be base-catalysed, for example with ethanolic potassium hydroxide solution, or acid-catalysed, for example with sulphuric acid. The cyclohexenone of general formula (10-2), wherein m¹ denotes one of the numbers 1 or 2 and m² denotes one of the numbers 1 or 2, may be hydrogenated to form the corresponding cyclohexanone derivatives of general formula (10-3), wherein m¹ denotes one of the numbers 1 or 2 and m² denotes one of the numbers 1 or 2. The hydrogenation may be carried out for example in a hydrogen atmosphere with a catalyst, such as for example palladium on charcoal, and in a suitable solvent.

Scheme 11:

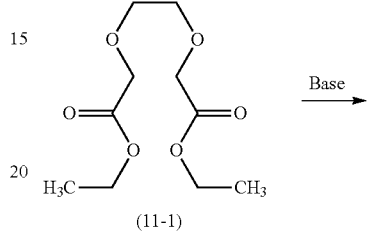

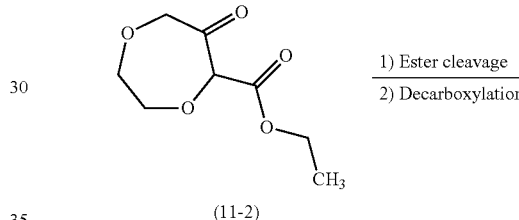

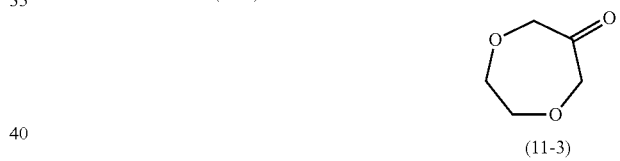

A compound of formula (11-1) may be deprotonated with a base, such as for example sodium-tert-butoxide, and in a suitable solvent, such as for example tetrahydrofuran, and then cyclised to form a compound of formula (11-2). The ester group may first of all be saponified under suitable conditions, for example with HCl in ethanol, and then decarboxylated, to obtain the compound of formula (11-3).

A general method of synthesising piperazinones of general formula (12-7), wherein $R^1$ and $R^2$ are defined as mentioned hereinbefore, is shown in Scheme 12a.

Scheme 12a:

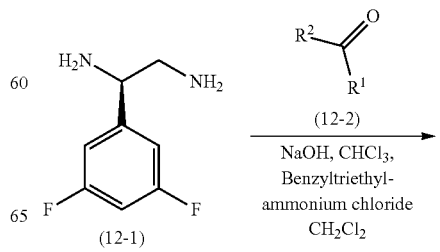

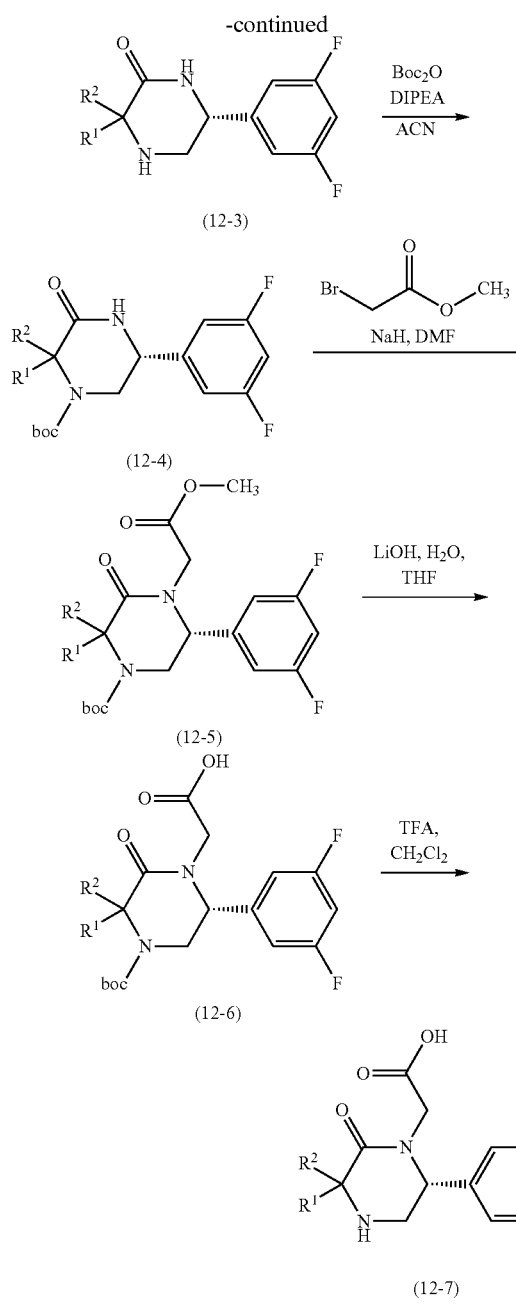

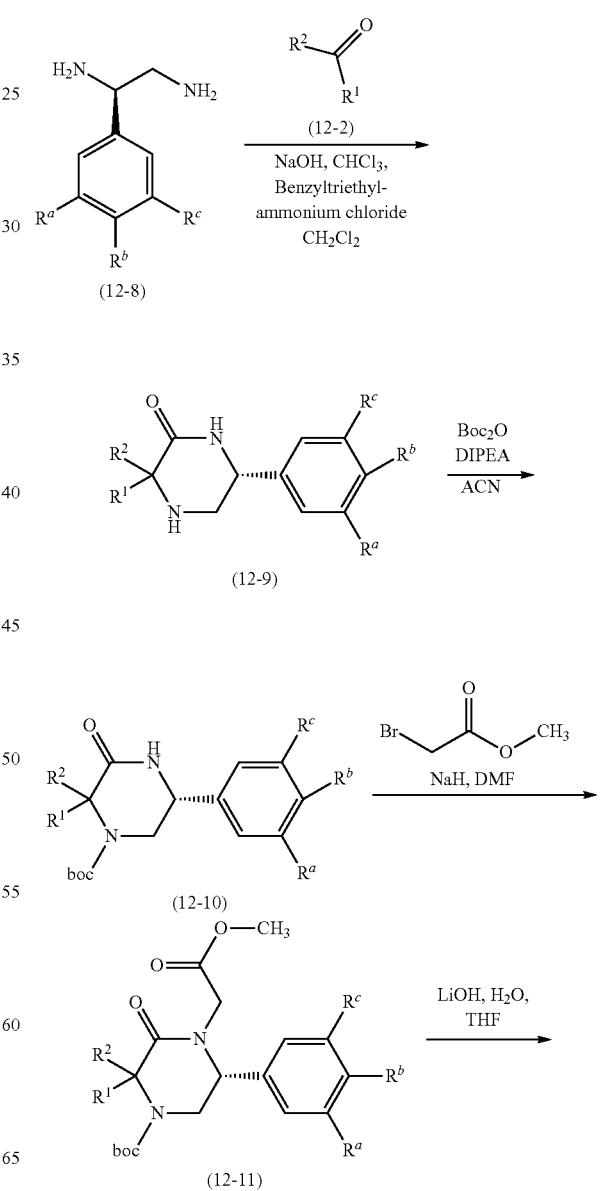

are defined as mentioned hereinbefore, may be carried out by basic or acidic hydrolysis (J. March, Advanced Organic Chemistry (New York: J. Wiley and Sons, 1985) in an inert solvent. It is particularly preferable to use alkali metal hydroxides such as lithium hydroxide in a mixture of water and tetrahydrofuran.

The Boc protective group of the acid of general formula (12-6) may be cleaved under suitable conditions as described for example in T. W. Greene, P. G. M. Wuts, "Protective Groups in Organic Synthesis", Wiley, 1991 and 1999. It is preferable to use trifluoroacetic acid in dichloromethane at ambient temperature under normal pressure. After the deprotection, the acid of general formula (12-7) is obtained, wherein $R^1$ and $R^2$ are defined as mentioned hereinbefore.

As shown in Scheme 12b, piperazinones of general formula (12-13), wherein $R^1$, $R^2$, $R^a$, $R^b$ and $R^c$ are defined as mentioned hereinbefore, may be prepared analogously to Scheme 12a.

Scheme 12b:

Reacting 1-(3,5-difluoro-phenyl)-ethane-1,2-diamine (12-1) with a ketone of general formula (12-2), wherein $R^1$ and $R^2$ are defined as mentioned hereinbefore, in a suitable solvent such as for example dichloromethane and in the presence of chloroform, benzyltriethylammonium chloride and a base such as for example sodium hydroxide solution, yields the piperazinone of general formula (12-3), wherein $R^1$ and $R^2$ are defined as mentioned hereinbefore. The piperazinone of general formula (12-3) may be reacted under suitable reaction conditions first of all into the corresponding tert-butylcarbamate of general formula (12-4), wherein $R^1$ and $R^2$ are defined as mentioned hereinbefore, and then with methyl bromoacetate to form the ester of general formula (12-5), wherein $R^1$ and $R^2$ are defined as mentioned hereinbefore. The saponification of the ester (12-5) to obtain the corresponding acid of general formula (12-6), wherein $R^1$ and $R^2$ -continued

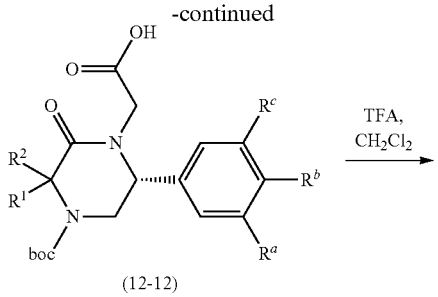
(12-12)

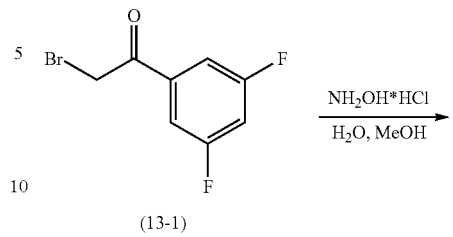

Scheme 13a:

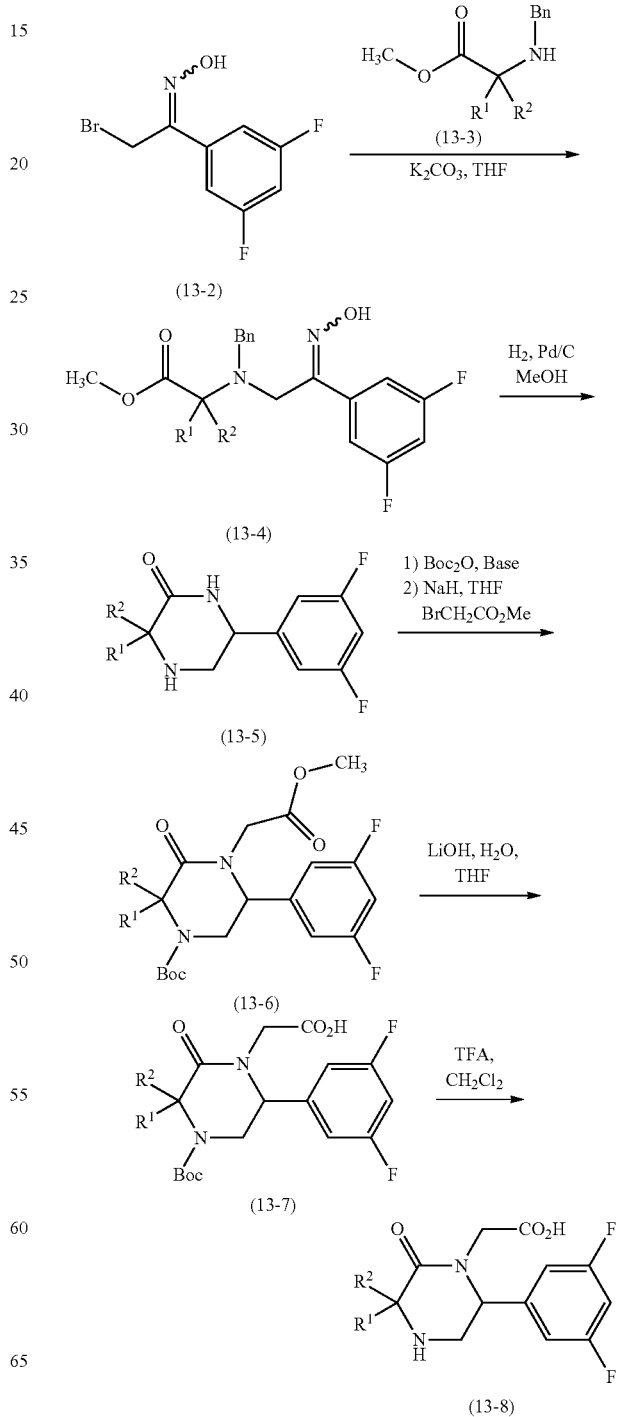

Reacting a compound of general formula (12-8), wherein $R^a$, $R^b$ and $R^c$ are defined as mentioned hereinbefore, with a ketone of general formula (12-2), wherein $R^1$ and $R^2$ are defined as mentioned hereinbefore, in a suitable solvent such as for example dichloromethane and in the presence of chloroform, benzyltriethylammonium chloride and a base, such as for example sodium hydroxide solution, yields a piperazinone of general formula (12-9), wherein $R^1$, $R^2$, $R^a$, $R^b$ and $R^c$ are defined as mentioned hereinbefore. The piperazinone of general formula (12-9) may be reacted under suitable reaction conditions first of all to form a corresponding tert-butylcarbamate of general formula (12-10), wherein $R^1$, $R^2$, $R^a$, $R^b$ and $R^c$ are defined as mentioned hereinbefore, and then with methyl bromoacetate, to form the ester of general formula (12-11), wherein $R^1$, $R^2$, $R^a$, $R^b$ and $R^c$ are defined as mentioned hereinbefore. The saponification of the ester (12-11) to form a corresponding acid of general formula (12-12), wherein $R^1$, $R^2$, $R^a$, $R^b$ and $R^c$ are defined as mentioned hereinbefore, may be carried out by basic or acidic hydrolysis (J. March, Advanced Organic Chemistry (New York: J. Wiley and Sons, 1985) in an inert solvent. It is particularly preferred to use alkali metal hydroxides such as lithium hydroxide in a mixture of water and tetrahydrofuran.

The Boc-protective group of an acid of general formula (12-12), wherein $R^1$, $R^2$, $R^a$, $R^b$ and $R^c$ are defined as mentioned hereinbefore, may be cleaved under suitable conditions as described for example in T. W. Greene, P. G. M. Wuts, "Protective Groups in Organic Synthesis", Wiley, 1991 and 1999. It is preferable to use trifluoroacetic acid in dichloromethane at ambient temperature under normal pressure. After the deprotection the acid of general formula (12-13) is obtained, wherein $R^1$, $R^2$, $R^a$, $R^b$ and $R^c$ are defined as mentioned hereinbefore.

A general method of synthesising piperazinones of general formula (13-8), wherein $R^1$ and $R^2$ are defined as mentioned hereinbefore, is shown in Scheme 13a.

Reacting 2-bromo-1-(3,5-difluoro-phenyl)-ethanone (13-1) with hydroxylamine hydrochloride yields the oxime of general formula (13-2). Reacting 2-bromo-1-(3,5-difluoro-phenyl)-ethanone oxime with an α-aminoester of general formula (13-3), wherein $R^1$ and $R^2$ are defined as mentioned hereinbefore, yields the oxime of general formula (13-4), wherein $R^1$ and $R^2$ are defined as mentioned hereinbefore. Various bases in inert solvents may be used for this reaction, for example $NaHCO_3$, $K_2CO_3$ and $Na_3PO_4$. A suitable solvent is THF, for example. Under suitable reaction conditions the hydrogenation of the oxime of general formula (13-4), wherein $R^1$ and $R^2$ are defined as mentioned hereinbefore, in the presence of a catalyst yields the piperazinone of general formula (13-5), wherein $R^1$ and $R^2$ are defined as mentioned hereinbefore. Hydrogenations with palladium on charcoal as catalyst at elevated hydrogen pressure and elevated temperatures are preferred. The introduction of a suitable protective group onto the piperazinone of general formula (13-5), wherein $R^1$ and $R^2$ are defined as mentioned hereinbefore, may be carried out analogously to methods described (T. W. Greene, P. G. M. Wuts, "Protective Groups in Organic Synthesis", Wiley, 1991 and 1999). The introduction of a Boc protective group by means of Boc-anhydride in a suitable solvent in the presence of a base is particularly preferred. The piperazinone thus obtained may be reacted under suitable reaction conditions with a bromoacetic acid ester derivative, methyl bromoacetate being most particularly preferred, to form an ester of general formula (13-6), wherein $R^1$ and $R^2$ are defined as mentioned hereinbefore. The saponification of the ester of general formula (13-6), wherein $R^1$ and $R^2$ are defined as mentioned hereinbefore, to form the corresponding acid of general formula (13-7), wherein $R^1$ and $R^2$ are defined as mentioned hereinbefore, may be carried out as described in T. W. Greene, P. G. M. Wuts, "Protective Groups in Organic Synthesis", Wiley, 1991 and 1999. The use of alkali metal hydroxides such as lithium hydroxide in a mixture of water and tetrahydrofuran is particularly preferred.

The deprotection of the piperazinone of general formula (13-7), wherein $R^1$ and $R^2$ are defined as mentioned hereinbefore, may be carried out under suitable conditions as described for example in T. W. Greene, P. G. M. Wuts, "Protective Groups in Organic Synthesis", Wiley, 1991 and 1999. The cleaving of the Boc protective group may be carried out for example with trifluoroacetic acid in dichloromethane or methanolic hydrochloric acid. After the cleaving of the protective group the acid of general formula (13-8) is obtained, wherein $R^1$ and $R^2$ are defined as mentioned hereinbefore.

A general method of synthesising piperazinones of general formula (13-16), wherein $R^1$, $R^2$, $R^a$, $R^b$ and $R^c$ are defined as mentioned hereinbefore, is shown in Scheme 13b.

Scheme 13b:

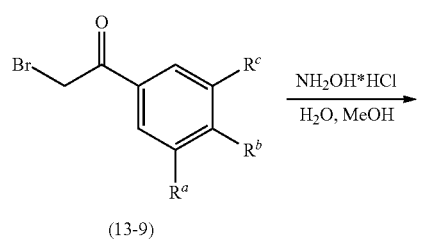

(13-9)

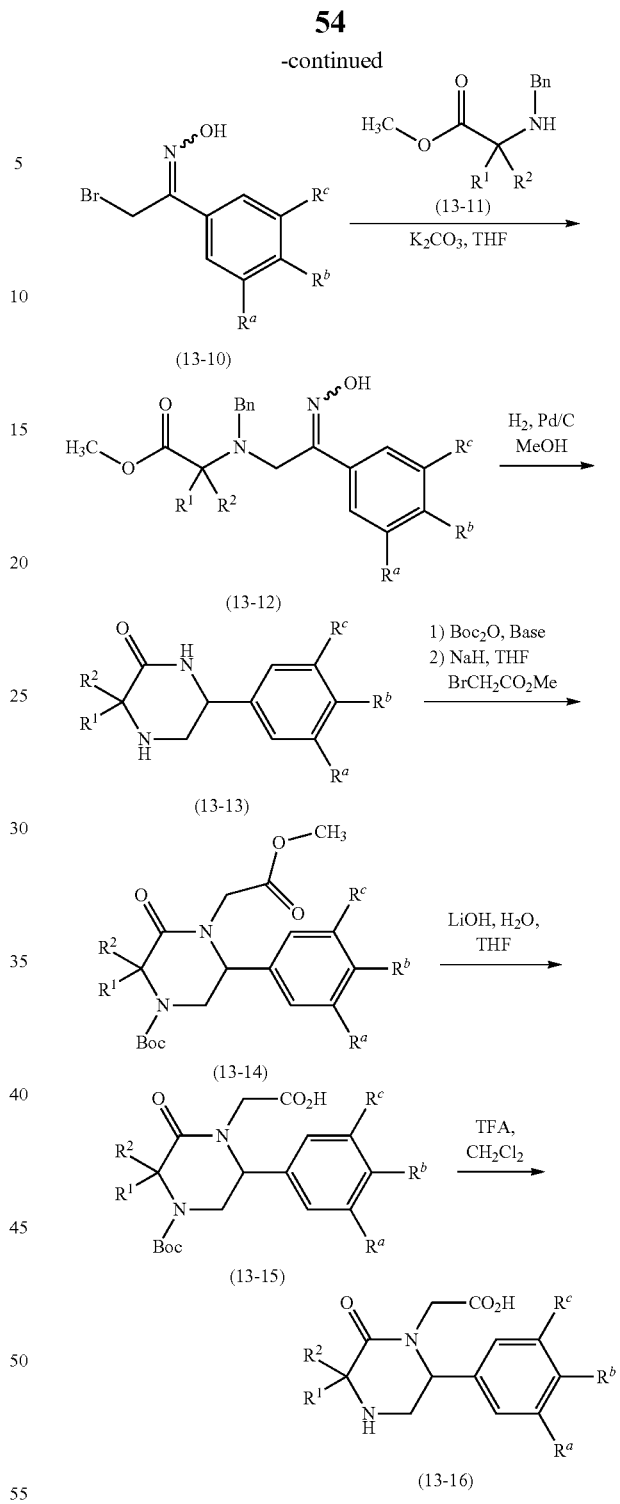

The reaction of a bromoketone of general formula (13-9), wherein $R^a$, $R^b$ and $R^c$ are defined as mentioned hereinbefore, with hydroxylamine hydrochloride yields the oxime of general formula (13-10), wherein $R^a$, $R^b$ and $R^c$ are defined as mentioned hereinbefore. Reacting the oxime of general formula (13-10), wherein $R^a$, $R^b$ and $R^c$ are defined as mentioned hereinbefore, with an α-aminoester of general formula (13-11), wherein $R^1$ and $R^2$ are defined as mentioned hereinbefore, yields the oxime of general formula (13-12), wherein $R^1$, $R^2$, $R^a$, $R^b$ and $R^c$ are defined as mentioned hereinbefore.

Various bases in inert solvents may be used for this reaction, for example NaHCO$_3$, K$_2$CO$_3$ and Na$_3$PO$_4$. A suitable solvent is THF, for example. Under suitable reaction conditions the hydrogenation of the oxime of general formula (13-12), wherein R$^1$, R$^2$, R$^a$, R$^b$ and R$^c$ are defined as mentioned hereinbefore, in the presence of a catalyst yields the piperazinone of general formula (13-13), wherein R$^1$, R$^2$, R$^a$, R$^b$ and R$^c$ are defined as mentioned hereinbefore. Hydrogenations with palladium on charcoal as catalyst at elevated hydrogen pressure and elevated temperatures are preferred. The introduction of a suitable protective group onto the piperazinone of general formula (13-13), wherein R$^1$, R$^2$, R$^a$, R$^b$ and R$^c$ are defined as mentioned hereinbefore, may be carried out analogously to methods described (T. W. Greene, P. G. M. Wuts, "Protective Groups in Organic Synthesis", Wiley, 1991 and 1999). The introduction of a Boc protective group by means of Boc-anhydride in a suitable solvent in the presence of a base is particularly preferred. The piperazinone thus obtained may be reacted under suitable reaction conditions with a bromoacetic acid ester derivative, methyl bromoacetate being most particularly preferred, to form an ester of general formula (13-14), wherein R$^1$, R$^2$, R$^a$, R$^b$ and R$^c$ are defined as mentioned hereinbefore. The saponification of the ester of general formula (13-14), wherein R$^1$, R$^2$, R$^a$, R$^b$ and R$^c$ are defined as mentioned hereinbefore, to form the corresponding acid of general formula (13-15), wherein R$^1$, R$^2$, R$^a$, R$^b$ and R$^c$ are defined as mentioned hereinbefore, may be carried out as described in T. W. Greene, P. G. M. Wuts, "Protective Groups in Organic Synthesis", Wiley, 1991 and 1999. The use of alkali metal hydroxides such as lithium hydroxide in a mixture of water and tetrahydrofuran is particularly preferred.

The deprotection of the piperazinone of general formula (13-15), wherein R$^1$, R$^2$, R$^a$, R$^b$ and R$^c$ are defined as mentioned hereinbefore, may be carried out under suitable conditions as described for example in T. W. Greene, P. G. M. Wuts, "Protective Groups in Organic Synthesis", Wiley, 1991 and 1999. The cleaving of the Boc protective group may be carried out for example with trifluoroacetic acid in dichloromethane or methanolic hydrochloric acid. After the cleaving of the protective group the acid of general formula (13-16) is obtained, wherein R$^1$, R$^2$, R$^a$, R$^b$ and R$^c$ are defined as mentioned hereinbefore.

Compounds of general formula (14-5), wherein R$^1$, R$^2$, R$^a$, R$^b$ and R$^c$ are defined as mentioned hereinbefore, may be prepared as shown in Scheme 14.

Scheme 14:

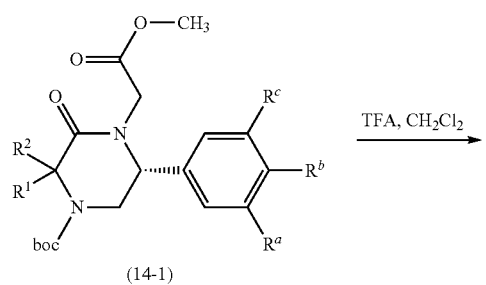

(14-1)

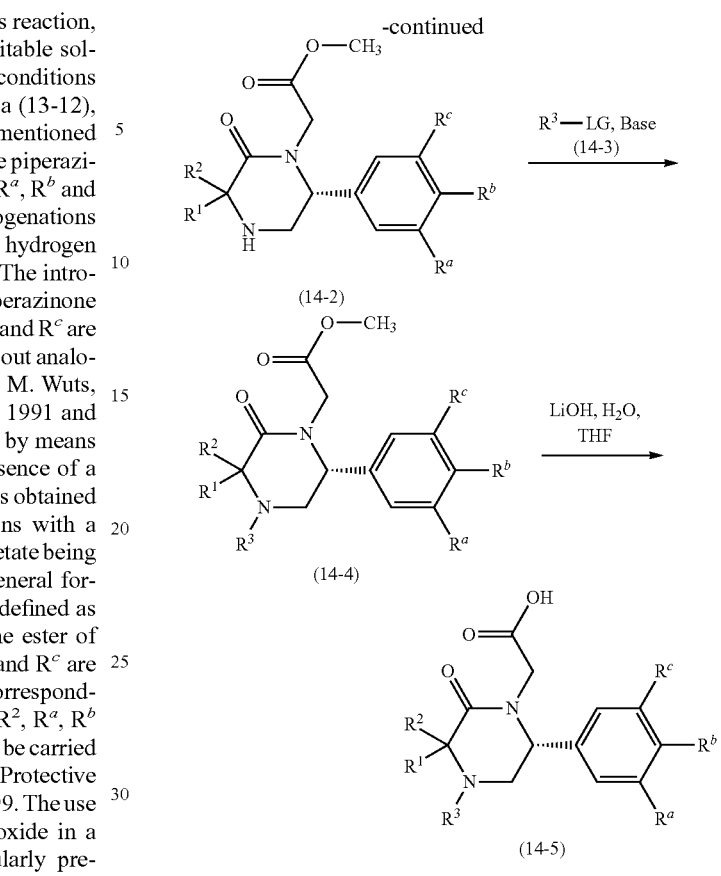

The Boc protective group of the compound of general formula (14-1), wherein R$^1$, R$^2$, R$^a$, R$^b$ and R$^c$ are defined as mentioned hereinbefore, may be cleaved under suitable conditions as described for example in T. W. Greene, P. G. M. Wuts, "Protective Groups in Organic Synthesis", Wiley, 1991 and 1999.

Compounds of general formula (14-2), wherein R$^1$, R$^2$, R$^a$, R$^b$ and R$^c$ are defined as mentioned hereinbefore, may be reacted with compounds of general formula (14-3), wherein R$^3$ is defined as mentioned hereinbefore and LG denotes a leaving group, in a suitable solvent and optionally with the aid of a base. Bromides and iodides, trifluoromethanesulphonates, methanesulphonates and toluenesulphonates may act as the leaving group LG, but it need not be restricted thereto. Most particularly preferably, iodides are the leaving group LG. Most particularly preferably methyl is R$^3$. Acetonitrile is a suitable solvent and potassium carbonate is a suitable base. The saponification of the ester of general formula (14-4), wherein R$^1$, R$^2$, R$^3$, R$^a$, R$^b$ and R$^c$ are defined as mentioned hereinbefore, to form the corresponding acid of general formula (14-5), wherein R$^1$, R$^2$, R$^3$, R$^a$, R$^b$ and R$^c$ are defined as mentioned hereinbefore, may be carried out using basic or acidic hydrolysis (J. March, Advanced Organic Chemistry (New York: J. Wiley and Sons, 1985) in an inert solvent. It is particularly preferable to use alkali metal hydroxides such as lithium hydroxide in a mixture of water and tetrahydrofuran.

The new compounds of general formula I according to the invention and their intermediates may contain one or more chiral centres. If for example there are two chiral centres, the compounds may occur in the form of two diastereomeric pairs of antipodes. The invention includes the individual isomers and the mixtures thereof.

The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I and their intermediates may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (–)-tartaric acid, (+) or (–)-diacetyl tartaric acid, (+) or (–)-monomethyl tartrate or (+) or (–)-camphorsulphonic acid, or an optically active base, for example with (R)-(+)-1-phenylethylamine, (S)-(–)-1-phenylethylamine or (S)-brucine.

According to a conventional method of separating isomers, the racemate of a compound of general formula I and its intermediates is reacted with one of the above-mentioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (–) form.

The (R) or (S) enantiomer alone or a mixture of two optically active diastereomeric compounds covered by general formula I may also be obtained by performing the syntheses described above with a suitable reaction component in the (R) or (S) configuration.

The absolute stereochemistry may be determined by X-ray crystallography of crystalline products or intermediates. These compounds are optionally reacted with suitable reagents that have an asymmetric centre of a known configuration.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC membranes (~20 μg protein) are incubated for 180 minutes at ambient temperature with 50 pM $^{125}$I-iodotyrosyl-Calcitonin-Gene-Related Peptide and increasing concentrations of the test substances in a total volume of 250 μl (assay buffer: 10 mM tris, 50 mM NaCl, 5 mM $MgCl_2$, 1 mM EDTA, pH=7.4). The incubation is ended by rapid filtration through GF/B-glass fibre filters treated with polyethyleneimine (0.1%) using a cell harvester. The protein-bound radioactivity is measured using a gamma counter. Non-specific binding is defined as the bound radioactivity after the presence of 1 μM BIBN4096BS during incubation.

The concentration binding curves are analysed using computer-aided non-linear curve fitting.

The compounds mentioned hereinbefore show $K_i$ values ≤50 μm in the test described.

B. CGRP Antagonism in SK-N-MC Cells

SK-N-MC cells (~1000 cells per well) are incubated for 30 minutes in the presence of increasing concentrations of CGRP and different concentrations of the test substance.

The cAMP contents of the samples are determined using an AlphaScreen cAMP assay kit (Perkin Elmer) and the $pA_2$ values of antagonistically acting substances are determined graphically.

To demonstrate that the compounds of general formula I exhibit good to very good CGRP-antagonistic activities with different structural elements, the following Table gives the $K_i$ values obtained according to the test procedure described above.

| No. | CGRP binding $K_i$ [nM] |
|---|---|
| (1a) | 0.03 |
| (1b) | 1.77 |
| (2) | 1.02 |
| (3) | 0.72 |
| (13) | 0.72 (Diastereomer 1) |
|  | 0.71 (Diastereomer 2) |
| (14) | 0.07 |
| (15a) | 0.10 |
| (15b) | 0.39 |
| (16a) | 5.40 |
| (16b) | 0.13 |
| (17) | 0.03 |
| (18) | 0.84 |
| (19) | 1.41 |
| (20) | 0.96 |
| (21) | 0.44 |
| (22) | 0.11 |
| (23) | 0.05 |
| (24) | 0.07 |

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects.

Preferably, the compounds according to the invention are suitable for the acute and prophylactic treatment of migraine and cluster headaches, for treating irritable bowel syndrome (IBS) and for the preventive and acute-therapeutic treatment of hot flushes in oestrogen-deficient women.

Therefore in another aspect the present invention relates to the use of the compounds of the previously mentioned general formula I for the treatment of the above-mentioned diseases (indications).

In another aspect the present invention relates to the use of the compounds of the previously mentioned general formula I for preparing a pharmaceutical composition for the treatment of the above-mentioned diseases (indications).

By a "treatment" is meant according to the invention an acute, preventive, palliative or curative treatment.

The present invention further relates to the use of previously mentioned general formula I for the preventive treatment of the above-mentioned diseases (indications).

The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to 10 mg/kg of body weight when administered orally, nasally or by inhalation, 1 to 3× a day in each case.

In another aspect the present invention relates to a process for the treatment of one of the previously mentioned diseases (indications) on a living creature, preferably in a human, requiring such a treatment, comprising administering a therapeutically effective amount of a compound of general formula I, optionally together with one or more excipients and/or diluents.

If the treatment with CGRP antagonists and/or CGRP release inhibitors is given as a supplement to conventional hormone replacement, it is advisable to reduce the doses specified above, in which case the dosage may be from 1/5 of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal anti-inflammatories, corticosteroids, calcium antagonists, 5-$HT_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal anti-inflammatories aceclofenac, acemetacin, acetyl-salicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other 5-$HT_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. mGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. INOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. sst2 receptor agonists may be added.

The dosage of these active substances is expediently 1/5 of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of the general formula according to the preferred embodiments above.

It is particularly preferable if the compounds of general formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of general formula I are administered by inhalation, particularly preferably if they are administered once or twice a day. For this purpose, the compounds of general formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

EXPERIMENTAL SECTION

The following compounds may be synthesised analogously to the general methods of preparation described hereinbefore (Schemes 1 to 14):

Example 1

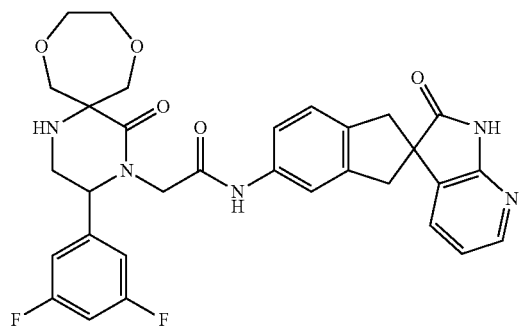

Example 2

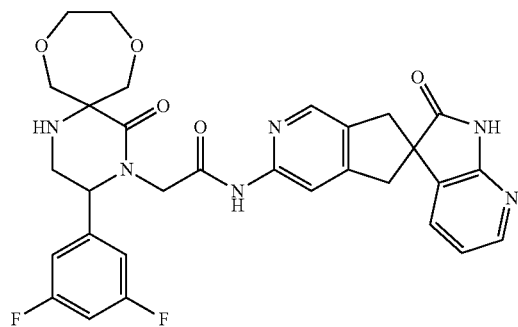

Example 3
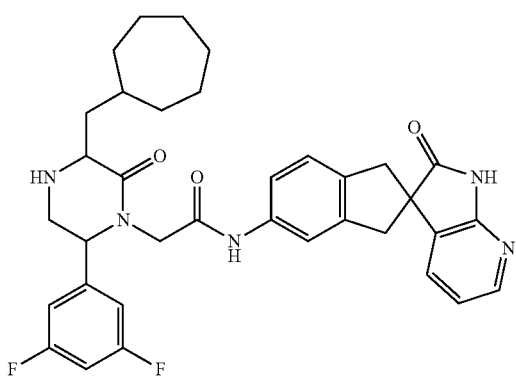
Example 4
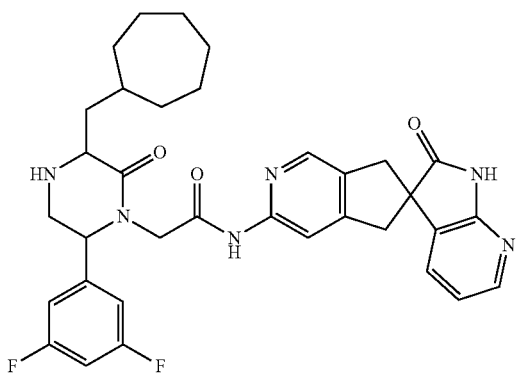
Example 5
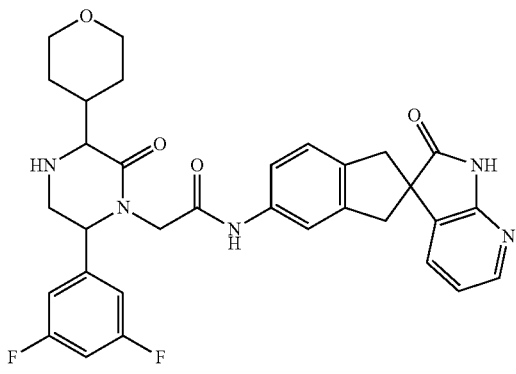
Example 6
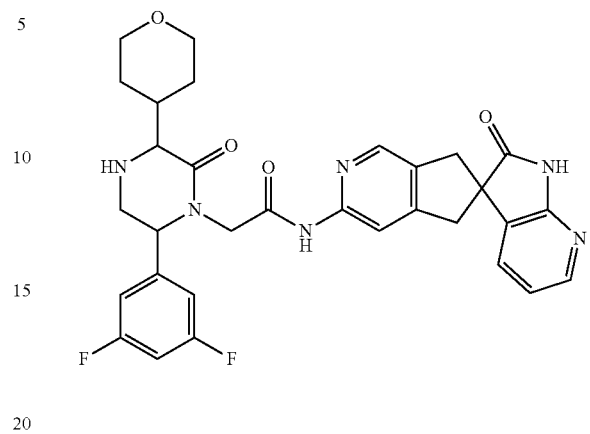
Example 7
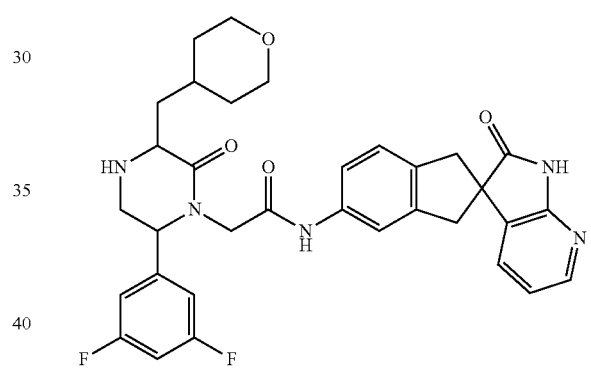
Example 8
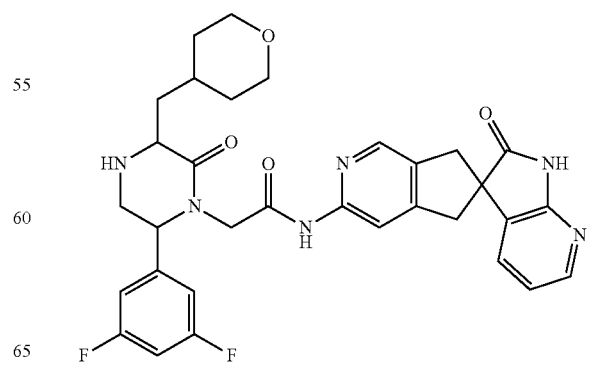

| 65 | 66 |
|---|---|
| Example 9 | Example 12 |
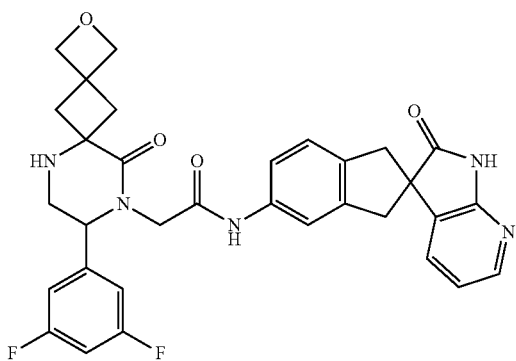 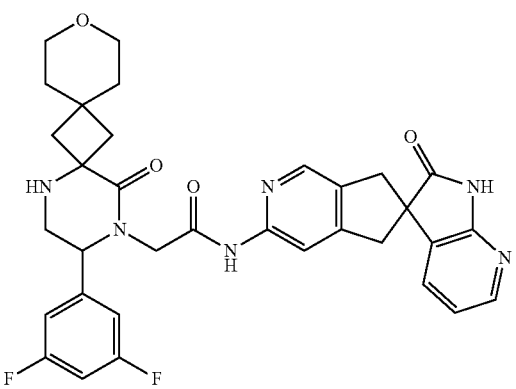
| Example 10 | Example 13 |
|---|---|
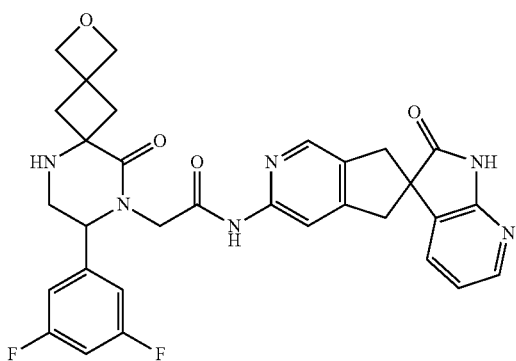 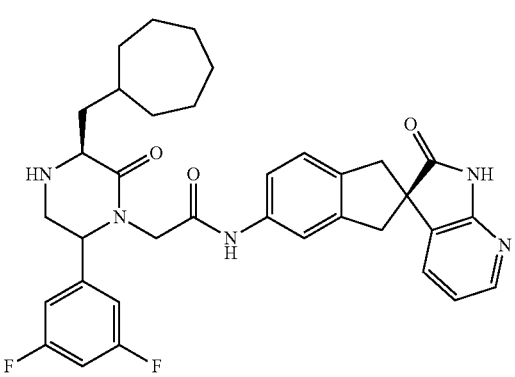 [SMILES: O=C(CN1C(=O)[C@H](CC2CCCCCC2)NCC1c1cc(F)cc(F)c1)Nc1ccc2c(c1)C[C@@]1(C2)C(=O)Nc2ncccc21]
| Example 11 | Example 14 |
|---|---|
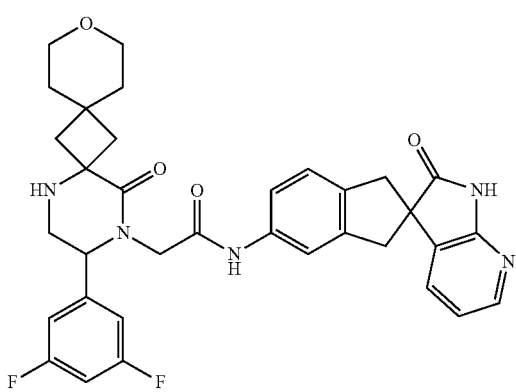 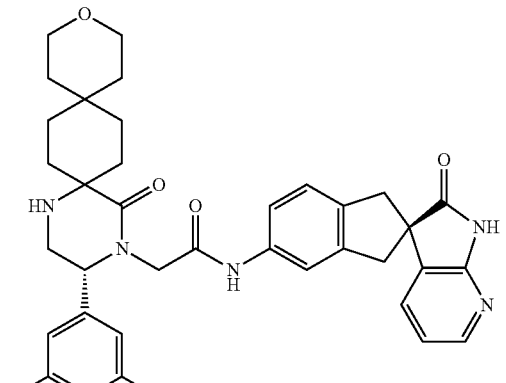

67
Example 15
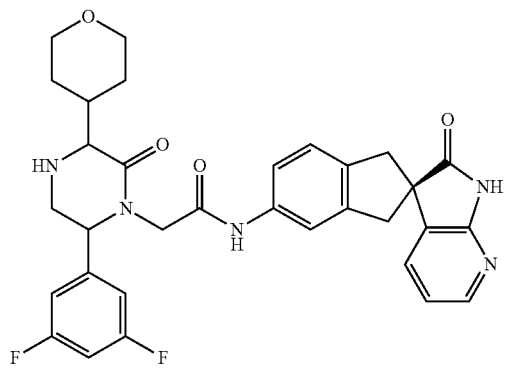 [SMILES: O=C(CN1C(=O)C(C2CCOCC2)NCC1c1cc(F)cc(F)c1)Nc1ccc2c(c1)C[C@@]1(C2)C(=O)Nc2ncccc21]
Example 16
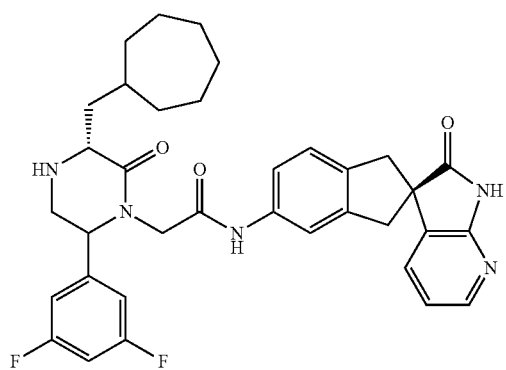 [SMILES: O=C(CN1C(=O)[C@@H](CC2CCCCCC2)NCC1c1cc(F)cc(F)c1)Nc1ccc2c(c1)C[C@@]1(C2)C(=O)Nc2ncccc21]
Example 17
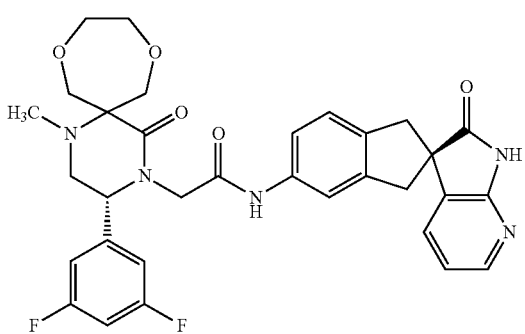 [SMILES: CN1C[C@@H](c2cc(F)cc(F)c2)N(CC(=O)Nc2ccc3c(c2)C[C@@]2(C3)C(=O)Nc3ncccc32)C(=O)C12COCCOC2]
68
Example 18
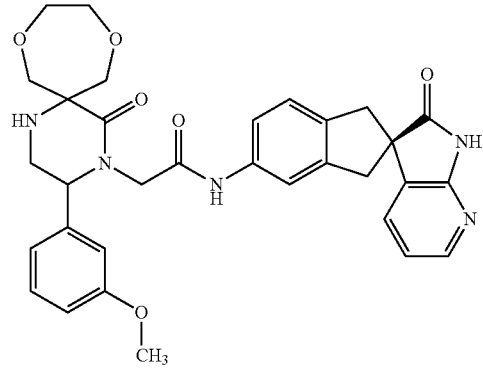 [SMILES: COc1cccc(C2CNC3(COCCOC3)C(=O)N2CC(=O)Nc2ccc3c(c2)C[C@@]2(C3)C(=O)Nc3ncccc32)c1]
Example 19
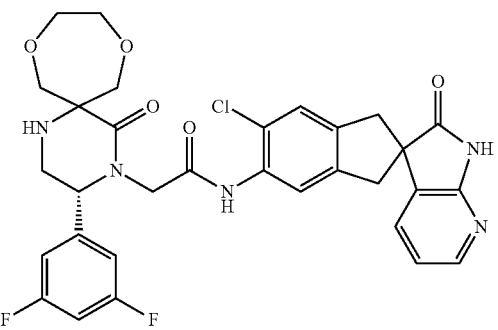 [SMILES: O=C(CN1C(=O)C2(COCCOC2)NC[C@H]1c1cc(F)cc(F)c1)Nc1cc2c(cc1Cl)CC1(C2)C(=O)Nc2ncccc21]
Example 20
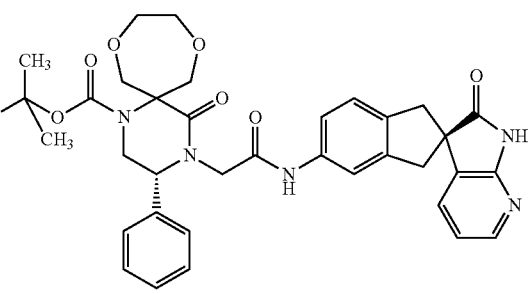

Example 21

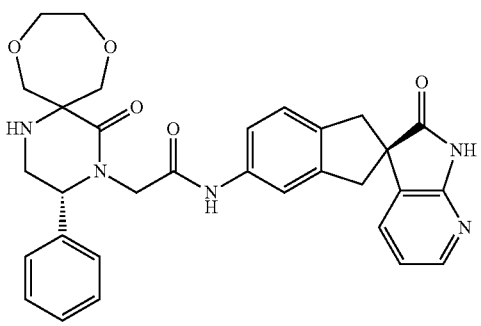 [SMILES: O=C(CN1C(=O)C2(COCCOC2)NC[C@H]1c1ccccc1)Nc1ccc2c(c1)C[C@@]1(C2)C(=O)Nc2ncccc21]

Example 22

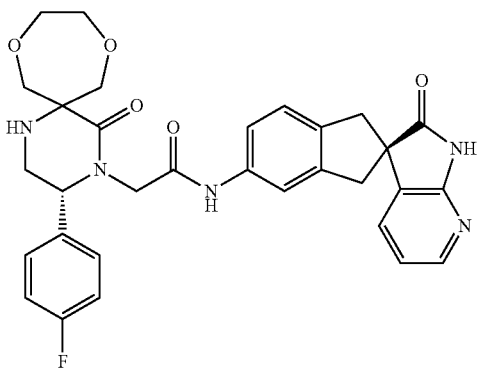 [SMILES: O=C(CN1C(=O)C2(COCCOC2)NC[C@H]1c1ccc(F)cc1)Nc1ccc2c(c1)C[C@@]1(C2)C(=O)Nc2ncccc21]

Example 23

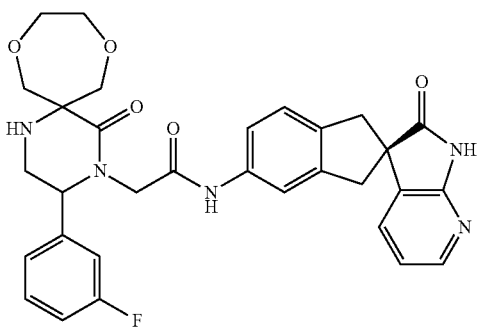 [SMILES: O=C(CN1C(=O)C2(COCCOC2)NCC1c1cccc(F)c1)Nc1ccc2c(c1)C[C@@]1(C2)C(=O)Nc2ncccc21]

Example 24

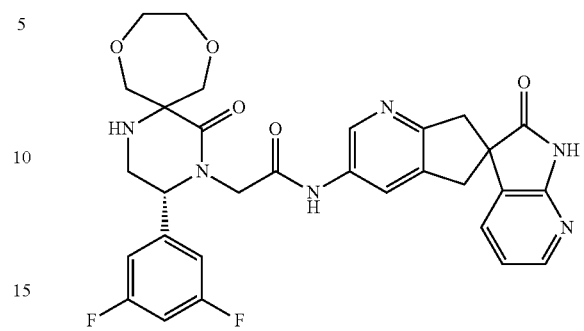

As a rule, ¹H-NMR and/or mass spectra have been obtained for the compounds prepared. Unless stated otherwise, $R_f$-values are determined using ready-made TLC silica gel plates 60 F254 (E. Merck, Darmstadt, Item no. 1.05714) without chamber saturation. The ratios given for the eluants relate to units by volume of the particular solvents. The units by volume given for $NH_3$ relate to a concentrated solution of $NH_3$ in water. Unless stated otherwise, the acid, base and salt solutions used in working up the reaction solutions are aqueous systems of the specified concentrations. Silica gel made by Millipore (MATREX™, 35-70 μm) is used for chromatographic purifications.

The HPLC data provided are measured under the parameters listed below and using the columns mentioned:

Columns Used:
(column temperature: 30° C.; injection volume: 5 μL; detection at 254 nm)

| S1 | Zorbax column (Agilent Technologies), SB (Stable Bond) C18; 1.8 μm; 3.0 × 30 mm |
| S2 | Sunfire C18 (Waters); C18; 2.5 μm; 3.0 × 30 mm |
| S3 | Zorbax column (Agilent Technologies), SB (Stable Bond) C18; 3.5 μm; 4.6 × 75 mm |
| S4 | Waters XBridge; C18; 2.5 μM; 3.0 × 30 mm |

Solvents Used:
Acidic Conditions:
solvent A: water (with 0.1% formic acid)
solvent B: acetonitrile (with 0.1% formic acid)
(The percentages stated relate to the total volume.)
Gradients:

| gradient | time [min] | % A | % B |
|---|---|---|---|
| G1 | 0.00 | 95 | 5 |
| (1.6 ml/min) | 0.10 | 95 | 5 |
| | 1.75 | 5 | 95 |
| | 1.90 | 5 | 95 |
| | 1.95 | 95 | 5 |
| | 2.00 | 95 | 5 |
| G2 | 0.00 | 95 | 5 |
| (1.6 ml/min) | 4.50 | 10 | 90 |
| | 5.00 | 10 | 90 |
| | 5.50 | 95 | 5 |

Acidic Conditions:
solvent A: water (with 0.2% formic acid)
solvent B: methanol (The percentages stated relate to the total volume.)
Gradients:

| gradient | time [min] | % A | % B |
|---|---|---|---|
| G3 | 0.00 | 95 | 5 |
| (1.6 ml/min) | 4.50 | 10 | 90 |
|  | 6.50 | 10 | 90 |
|  | 7.00 | 95 | 5 |
| G4 | 0.00 | 95 | 5 |
| (1.6 ml/min) | 2.00 | 10 | 90 |
|  | 7.00 | 10 | 90 |
|  | 7.50 | 95 | 5 |

Basic Conditions:
solvent A: water (with 0.2% ammonia)
solvent B: methanol+3% water
(The percentages stated relate to the total volume.)
Gradients:

| gradient | time [min] | % A | % B |
|---|---|---|---|
| G5 | 0.00 | 95 | 5 |
| (1.6 ml/min) | 0.20 | 95 | 5 |
|  | 2.80 | 5 | 95 |
|  | 3.00 | 5 | 95 |
|  | 3.10 | 0 | 100 |
|  | 3.80 | 0 | 100 |

Methods:

The particular method of HPLC used will be the result of the combination of the columns and gradients described above:

|  | column | gradient |
|---|---|---|
| method A | S1 | G1 |
| method B | S2 | G1 |
| method C | S3 | G2 |
| method D | S3 | G3 |
| method E | S3 | G4 |
| method F | S4 | G5 |

In preparative HPLC purification, generally the same gradients are used as were used to obtain the analytical HPLC data. The collection of the products is mass-controlled and the fractions containing the product are combined and freeze-dried.

In the absence of any more information regarding the configuration, it is unclear whether there are pure enantiomers involved or whether partial or even total racemisation has taken place.

The following abbreviations are used in the test descriptions:
AcOH acetic acid
BINAP 2,2'-bis(diphenylphosphino)-1,1'-binaphthyl
Boc tert-butyloxycarbonyl
cyc cyclohexane
CDI 1,1'-carbonyldimidazole
DCM dichloromethane
DIPE diisopropylether
DIPEA diisopropylethylamine
DMF N,N-dimethylformamide
DMSO dimethylsulphoxide
dppf 1,1'-bis(diphenyl-phosphino)ferrocene
of theoretical of theory
EI electron jet ionisation (in MS)
ESI electron spray ionisation (in MS)
EtOAc ethyl acetate
EtOH ethanol
E-water de-ionised water
FM eluant
HATU O-(7-azabenzotriazol-1-yl)-N,N,N,N-tetramethylamethyluronium
HCl hydrogen chloride
HCOOH formic acid
HOBT 1-hydroxybenzotriazole
HPLC High Performance Liquid Chromatography
HPLC-MS HPLC coupled mass spectrometry
i.vac. in vacuo (under vacuum)
conc. concentrated
MeOH methanol
MS mass spectrometry
MW molecular weight [g/mol]
NaOH sodium hydroxide
NH$_4$OH ammonium hydroxide (aqueous ammonia solution, 30%)
NMP N-methyl-2-pyrrolidine
Pd$_2$dba$_3$ bis(dibenzylideneacetone)-palladium(0)
PE petroleum ether
R$_f$ retention index (in TLC)
RP reversed phase
RT ambient temperature
R$_t$ retention time (in HPLC)
TEA triethylamine
TFA trifluoroacetic acid
THF tetrahydrofuran
ULTS circulating air dryer

| AcOH | acetic acid |
|---|---|
| BINAP | 2,2'-bis(diphenylphosphino)-1,1'-binaphthyl |
| Boc | tert-butyloxycarbonyl |
| cyc | cyclohexane |
| CDI | 1,1'-carbonyldimidazole |
| DCM | dichloromethane |
| DIPE | diisopropylether |
| DIPEA | diisopropylethylamine |
| DMF | N,N'-dimethylformamide |
| DMSO | dimethylsulphoxide |
| dppf | 1,1'-bis(diphenyl-phosphino)ferrocene |
| of theoretical | of theory |
| EI | electron jet ionisation (in MS) |
| ESI | electron spray ionisation (in MS) |
| EtOAc | ethyl acetate |
| EtOH | ethanol |
| E-water | de-ionised water |
| FM | eluant |
| HATU | O-(7-azabenzotriazol-1-yl)-N,N,N,N-tetramethylamethyluronium |
| HCl | hydrogen chloride |
| HCOOH | formic acid |
| HOBT | 1-hydroxybenzotriazole |
| HPLC | High Performance Liquid Chromatography |
| HPLC-MS | HPLC coupled mass spectrometry |
| i. vac. | in vacuo (under vacuum) |
| conc. | concentrated |
| MeOH | methanol |
| MS | mass spectrometry |
| MW | molecular weight [g/mol] |
| NaOH | sodium hydroxide |
| NH$_4$OH | ammonium hydroxide (aqueous ammonia solution, 30%) |
| NMP | N-methyl-2-pyrrolidine |
| Pd$_2$dba$_3$ | bis(dibenzylideneacetone)-palladium(0) |
| PE | petroleum ether |
| R$_1$ | retention index (in TLC) |
| RP | reversed phase |
| RT | ambient temperature |
| R$_t$ | retention time (in HPLC) |
| TEA | triethylamine |
| TFA | trifluoroacetic acid |

-continued

| THF | tetrahydrofuran |
| ULTS | circulating air dryer |

Preparation of the Starting Compounds

Intermediate 1 ethyl 6-oxo-[1,4]dioxepan-5-carboxylate

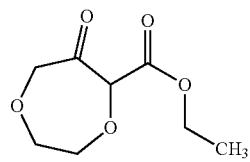

The mixing was carried out under a protective nitrogen gas atmosphere. 7.93 g (80.0 mmol) sodium-tert-butoxide were placed in 150 ml THF and heated to boiling point. At this temperature 8.50 g (36.3 mmol) ethyl (2-ethoxycarbonyl-methoxy-ethoxy)-acetate (prepared analogously to Canadian Journal of Chemistry; 74; 8; 1996; 1437-1446) in 100 ml THF were added dropwise within 3 h. After the addition had ended the mixture was refluxed for 1 h and then stirred overnight at RT. Then the reaction mixture was adjusted to pH 5 with glacial acetic acid and concentrated by rotary evaporation. The residue was mixed with water and extracted with ethyl acetate. The organic phases were combined, dried and the solvent was eliminated under reduced pressure and with gentle heating.

Yield: 2.4 g (35% of theoretical)
ESI-MS: m/z=189 (M+H)$^+$
$R_f$: 0.5 (silica gel, petroleum ether/ethyl acetate=2:1)

Intermediate 2

[1,4]dioxepan-6-one

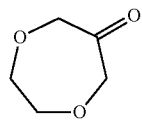

11.5 g (61.1 mmol) ethyl 6-oxo-[1,4]dioxepan-5-carboxylate were refluxed with 100 ml of a 10% aqueous hydrochloric acid solution for 2.5 h. After cooling the reaction mixture was saturated with potassium carbonate and then extracted with diethyl ether. The organic phases were combined and evaporated to dryness by rotary evaporation.

Yield: 4.50 g (63% of theoretical)
EI-MS: m/z=116 (M*)$^+$
$R_t$ (HPLC): 1.27 min (method C)

Intermediate 3

(R)-3-(3,5-difluoro-phenyl)-8,11-dioxa-1,4-diaza-spiro[5.6]dodecan-5-one

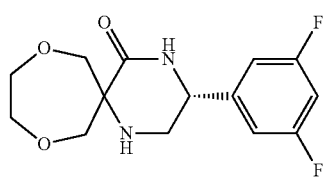 [SMILES: O=C1N[C@H](c2cc(F)cc(F)c2)CNC12COCCOC2]

3.13 g (15.0 mmol) (R)-1-(3,5-difluorophenyl)ethan-1,2-diamine-hydrochloride were placed with 0.17 g (0.73 mmol) benzyltriethylammonium chloride in 30 ml dichloromethane and cooled with ice/acetone. Then 5.21 ml (102.2 mmol) of a 50% sodium hydroxide solution were added. At 0° C. to 2° C., 1.70 g (14.6 mmol) [1,4]dioxepan-6-one together with 1.83 ml (22.7 mmol) chloroform and 20 ml dichloromethane were added dropwise within 1.5 h. The mixture was left overnight to warm up to RT. Then it was cooled to 0° C. and the reaction mixture was adjusted to pH1 with a 6N aqueous hydrochloric acid solution. The phases were separated. The aqueous phase was made alkaline with a 4N sodium hydroxide solution and extracted with ethyl acetate. The combined organic phases were dried and evaporated to dryness by rotary evaporation. Purification was carried out by flash chromatography.

Yield: 1.10 g (25% of theoretical)
ESI-MS: m/z=299 (M+H)$^+$
$R_t$ (HPLC): 0.95 min (method A)

The enantiomeric (S) compound may be obtained analogously to the method of synthesis described above using the corresponding (S)-configured reaction component.

Intermediate 4

(R)-tert-butyl 3-(3,5-difluorophenyl)-5-oxo-8,11-dioxa-1,4-diazaspiro[5.6]dodecane-1-carboxylate 3.93 g (18.0 mmol) di-tert-butyl-dicarbonate was added at RT to 1.10 g (3.69 mmol) (R)-3-(3,5-difluoro-phenyl)-8,11-dioxa-1,4-diaza-spiro[5.6]dodecan-5-one and 0.64 ml (3.70 mmol) DIPEA in 30 ml acetonitrile. After 7 h refluxing another 2.00 g (9.16 mmol) di-tert-butyl-dicarbonate were added and the mixture was refluxed overnight. Then the solvent was spun off and the residue was purified by flash chromatography.

Yield: 0.52 g (35% of theoretical)
ESI-MS: m/z=399 (M+H)$^+$
$R_t$ (HPLC): 1.33 min (method A)
The enantiomeric (S) compound may be obtained analogously to the method of synthesis described above using the corresponding (S)-configured starting component.

Intermediate 5

(R)-tert-butyl 3-(3,5-difluoro-phenyl)-4-methoxycarbonylmethyl-5-oxo-8,11-dioxa-1,4-diaza-spiro[5.6]dodecane-1-carboxylate

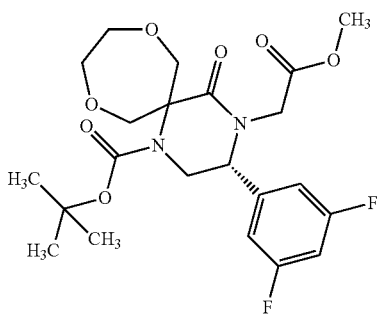 [SMILES: COC(=O)CN1C(=O)C2(COCCOC2)N(C(=O)OC(C)(C)C)C[C@H]1c1cc(F)cc(F)c1]

The mixture was prepared under a protective nitrogen gas atmosphere. 62.8 mg (1.44 mmol) sodium hydride (55% in paraffin oil) were added at 0° C. to 0.52 g (1.31 mmol) 5-(R)-tert-butyl 3-(3,5-difluorophenyl)-5-oxo-8,11-dioxa-1,4-diazaspiro[5.6]-dodecane-1-carboxylate in 20 ml DMF and the mixture was stirred for 20 min at 0° C. Then 0.14 ml (1.44 mmol) methyl bromoacetate in 5 ml DMF were slowly added dropwise and the mixture was stirred for 30 min at 0° C. and for 5 h at RT. The mixture was mixed with water and extracted with ethyl acetate. The combined organic phases were dried and evaporated to dryness by rotary evaporation.
Yield: 0.49 g (80% of theoretical)
ESI-MS: m/z=471 (M+H)$^+$
$R_t$ (HPLC): 1.43 min (method A)
The enantiomeric (S) compound may be obtained analogously to the method of synthesis described above using the corresponding (S)-configured starting component.

Intermediate 6 tert-butyl (R)-4-carboxymethyl-3-(3,5-difluoro-phenyl)-5-oxo-8,11-dioxa-1,4-diaza-spiro[5.6]dodecane-1-carboxylate

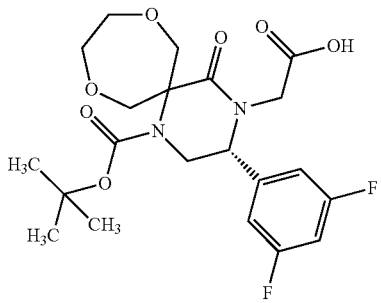 [SMILES: CC(C)(C)OC(=O)N1C[C@@H](c2cc(F)cc(F)c2)N(CC(=O)O)C(=O)C12COCCOC2]

0.235 g (0.50 mmol) tert-butyl (R)-3-(3,5-difluoro-phenyl)-4-methoxycarbonylmethyl-5-oxo-8,11-dioxa-1,4-diaza-spiro[5.6]dodecane-1-carboxylate, 5 ml THF, 1 ml of water and 13.2 mg (0.55 mmol) lithium hydroxide were stirred for 2 h at RT. Then the mixture was adjusted to pH7 with a 0.1N hydrochloric acid. The reaction mixture was evaporated to dryness by rotary evaporation.
Yield: 228 mg (quantitative)
ESI-MS: m/z=455 (M−H)$^−$
$R_t$ (HPLC): 1.30 min (method A)
The enantiomeric (S) compound may be obtained analogously to the method of synthesis described above using the corresponding (S)-configured starting component.

Intermediate 7

Methyl (S)-2-amino-3-cycloheptyl-propionate

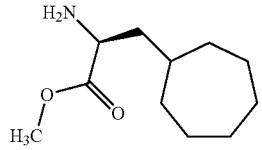

At −78° C. 7.80 ml (19.5 mmol) n-butyllithium (2.5 M in hexane) were added dropwise to 2.90 ml (16.2 mmol) (R)-2-isopropyl-3.6-dimethoxy-2,5-dihydropyrazine in 55 ml THF and the mixture was stirred for 2 h at −50° C. Then at −70° C. 4.25 g (17.8 mmol) (iodomethyl)cycloheptane in 15 ml THF were added dropwise, then the mixture was stirred for 30 min at −78° C., for 3 h at 0° C. and overnight at RT. After the addition of water and methanol it was stirred for 20 min at RT. Ethyl acetate was added and the mixture was extracted with saturated, aqueous saline solution. The organic phase was dried and evaporated to dryness by rotary evaporation. The residue was purified by flash chromatography. The fractions containing the product were combined and concentrated by rotary evaporation. The residue obtained was combined with acetonitrile, water and 1M hydrochloric acid and stirred overnight at RT. The acetonitrile was evaporated off and the aqueous phase was neutralised with potassium hydrogen carbonate. It was extracted with ethyl acetate. The combined organic phases were dried and evaporated to dryness by rotary evaporation.
Yield: 1.04 g (32% of theoretical)
ESI-MS: m/z=200 (M+H)$^+$
$R_t$ (HPLC): 0.96 min (method A)
The enantiomeric (R)-compound may be obtained analogously to the method of synthesis described above using the corresponding (R)-configured reaction component.

Intermediate 8 methyl (S)-2-benzylamino-3-cycloheptyl-propionate

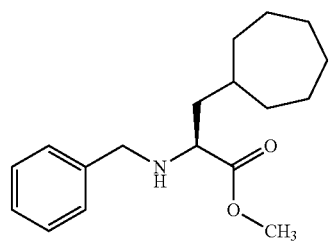 [SMILES: COC(=O)[C@H](CC1CCCCCC1)NCc1ccccc1]

1.04 g (5.22 mmol) methyl (S)-2-amino-3-cycloheptyl-propionate were stirred with 0.62 ml (5.22 mmol) benzylbromide, 1.44 g (10.4 mmol) potassium carbonate and 20 ml DMF at 100° C. for 3.5 h. Then water was added and the mixture was extracted with ethyl acetate. The organic phase was evaporated down and the residue was purified by flash chromatography.

Yield: 824 mg (55% of theoretical)
ESI-MS: m/z=290 (M+H)$^+$
R$_t$ (HPLC): 1.25 min (method A)

The enantiomeric (R)-compound may be obtained analogously to the method of synthesis described above using the corresponding (R)-configured starting component.

Intermediate 9 methyl (S)-2-(benzyl-{2-(3,5-difluoro-phenyl)-2-[hydroxyimino]-ethyl}-amino)-3-cycloheptyl-propionate

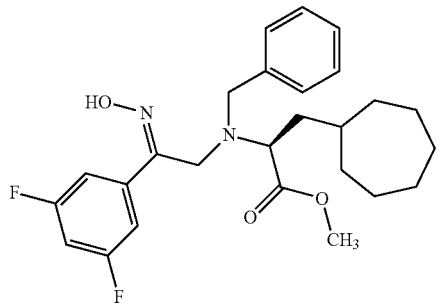 [SMILES: COC(=O)[C@H](CC1CCCCCC1)N(C/C(=N/O)c1cc(F)cc(F)c1)Cc1ccccc1]

820 mg (2.83 mmol) methyl (S)-2-benzylamino-3-cycloheptyl-propionate were stirred overnight at RT together with 0.71 g (2.83 mmol) 2-bromo-1-(3,5-difluoro-phenyl)-ethanone-oxime, 0.51 g (3.68 mmol) potassium carbonate and 10 ml THF. After the addition of water and ethyl acetate the organic phases were combined, washed with water, dried and evaporated to dryness by rotary evaporation. The residue was purified by RP-HPLC. The product-containing fractions were combined, the organic solvent was removed and the aqueous residue was made alkaline with saturated, aqueous sodium hydrogen carbonate solution. It was extracted with ethyl acetate, the organic phase was dried and concentrated by rotary evaporation.

Yield: 600 mg (46% of theoretical)
ESI-MS: m/z=459 (M+H)$^+$
R$_t$ (HPLC): 5.70 min/5.93 min (method D)

The enantiomeric (R)-compound may be obtained analogously to the method of synthesis described above using the corresponding (R)-configured starting component.

Intermediate 10

(S)-3-cycloheptylmethyl-6-(3,5-difluoro-phenyl)-piperazin-2-one

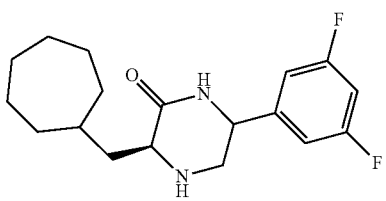 [SMILES: O=C1NC(c2cc(F)cc(F)c2)CN[C@H]1CC1CCCCCC1]

Under a hydrogen atmosphere 0.590 g (1.29 mmol) methyl (S)-2-(benzyl-{2-(3,5-difluoro-phenyl)-2-[hydroxyimino]-ethyl}-amino)-3-cycloheptyl-propionate and 0.10 g palladium on charcoal (10%) in 10 ml of methanol were hydrogenated for 3 days at 50° C. and 3.45 bar hydrogen pressure. After elimination of the catalyst the filtrate was concentrated by rotary evaporation. The residue was stirred with petroleum ether and diisopropylether and filtered off.

Yield: 210 mg (51% of theoretical)
ESI-MS: m/z=323 (M+H)$^+$
R$_t$ (HPLC): 0.92 min/1.00 min (method A)

Intermediate 11

(2S)-tert-butyl-2-(cycloheptylmethyl)-5-(3,5-difluorophenyl)-3-oxopiperazine-1-carboxylate

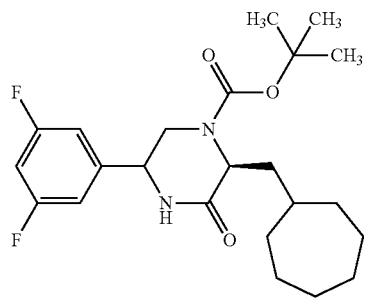 [SMILES: CC(C)(C)OC(=O)N1CC(c2cc(F)cc(F)c2)NC(=O)[C@@H]1CC1CCCCCC1]

120 mg (0.37 mmol) (3S)-3-(cycloheptylmethyl)-6-(3,5-difluorophenyl)piperazin-2-one, 90 mg (0.41 mmol) di-tert-butyldicarbonate and 0.06 ml (0.37 mmol) DIPEA were stirred overnight in 4 ml acetonitrile at RT. The reaction mixture was evaporated down and the residue was distributed between water and ethyl acetate. The aqueous phase was extracted with ethyl acetate. The organic phase was dried and evaporated down.

Yield: 90 mg (57% of theoretical)
ESI-MS: m/z=421 (M–H)$^-$
R$_t$ (HPLC): 2.26/2.39 min (method F)

Intermediate 12

(2S)-tert-butyl-2-(cycloheptylmethyl)-5-(3,5-difluorophenyl)-4-(2-methoxy-2-oxoethyl)-3-oxopiperazine-1-carboxylate

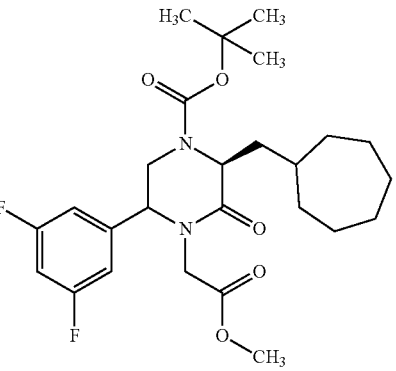 [SMILES: COC(=O)CN1C(=O)[C@H](CC2CCCCCC2)N(C(=O)OC(C)(C)C)CC1c1cc(F)cc(F)c1]

Under a nitrogen atmosphere 10 mg (0.23 mmol) sodium hydride were added at 0° C. to 90 mg (0.21 mmol) (2S)-tert-butyl-2-(cycloheptylmethyl)-5-(3,5-difluorophenyl)-3-oxopiperazine-1-carboxylate in 3 ml DMF. After 30 min at 0° C. 0.02 ml (0.26 mmol) methyl bromoacetate were added and then the reaction mixture was heated to RT overnight.

After evaporation the residue was mixed with water and extracted twice with ethyl acetate. The organic phase was dried and evaporated down.

Yield: 105 mg (quantitative)
ESI-MS: m/z=395 (M-Boc+H)$^+$
$R_t$ (HPLC): diastereomers: 2.26/2.39 min (method E)

Intermediate 13

2-((3S)-4-(tert-butoxycarbonyl)-3-(cycloheptylmethyl)-6-(3,5-difluorophenyl)-2-oxopiperazin-1-yl)ethanoic acid

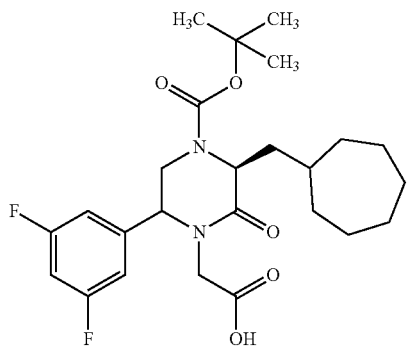 [SMILES: CC(C)(C)OC(=O)N1CC(c2cc(F)cc(F)c2)N(CC(=O)O)C(=O)[C@@H]1CC1CCCCCC1]

10 mg (0.42 mmol) lithium hydroxide in 800 µl water were added to 105 mg (0.21 mmol) (2S)-tert-butyl-2-(cycloheptylmethyl)-5-(3,5-difluorophenyl)-4-(2-methoxy-2-oxoethyl)-3-oxopiperazine-1-carboxylate in 2 ml THF. After 2 h tetrahydrofuran was distilled off and the aqueous solution was neutralised with hydrochloric acid. The aqueous phase was extracted with ethyl acetate. The ethyl acetate phase was dried and evaporated down.

Yield: 100 mg (98% of theoretical)
ESI-MS: m/z=381 (M-Boc+H)$^+$
$R_t$ (HPLC): 1.36/1.51 min (method E)

Intermediate 14

3-oxaspiro[5.5]undec-7-en-9-one

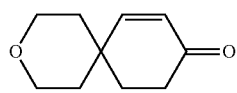 [SMILES: O=C1C=CC2(CCOCC2)CC1]

5.00 g (43.8 mmol) tetrahydropyran-4-carboxaldehyde and 3.56 ml (43.9 mmol) methylvinylketone were boiled in 70 ml of toluene with 0.07 ml conc. sulphuric acid using a water separator. After 3 h another 3.56 ml methylvinylketone were added and the mixture was boiled for a further 3 h. After cooling the reaction mixture was taken up in ethyl acetate, washed with water, dried and concentrated by rotary evaporation.

Yield: 1.30 g (18% of theoretical)
ESI-MS: m/z=167 (M+H)$^+$
$R_t$ (HPLC): 1.07 min (method A)

Intermediate 15

3-oxaspiro[5.5]undecan-9-one

Under a hydrogen atmosphere 1.30 g (7.82 mmol) 3-oxaspiro[5.5]undec-7-en-9-one were hydrogenated with 0.2 g Pd/C (10%) in 15 ml of ethyl acetate at 50° C. and 3 bar hydrogen pressure for three days. The reaction mixture was suction filtered and evaporated down.

Yield: 1.20 g (91% of theoretical)
ESI-MS: m/z=168 M*+
$R_t$ (HPLC): 0.69 min (method A)

Intermediate 16

(3R)-(3,5-difluorophenyl)-12-oxa-1,4-diaza-dispiro[5.2.5.2]hexadecan-5-one

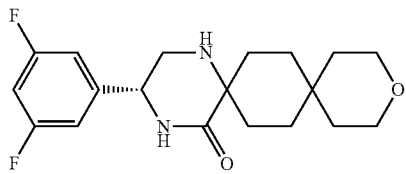

1.53 g (7.32 mmol) (1R)-1-(3,5-difluorophenyl)-ethan-1,2-diamine-hydrochloride and 82 mg (0.36 mmol) benzyltriethylammonium chloride were placed in 50 ml dichloromethane. While cooling with ice/acetone 2.55 ml (50.0 mmol) of 50% aqueous NaOH were added. At 0-2° C., 1.20 g (7.13 mmol) 3-oxaspiro[5.5]undecan-9-one and 0.89 ml (11.0 mmol) chloroform in 20 ml dichloromethane were added within 1.5 h. The reaction mixture was heated to RT overnight. At 0° C. 2.14 ml (12.9 mmol) of a 6M hydrochloric acid were added. The aqueous phase was adjusted to pH1 with a 6M hydrochloric acid. The organic phase was separated off and discarded. The aqueous phase was made alkaline and extracted twice with dichloromethane. The combined organic phases were dried and evaporated down. The residue was purified by flash chromatography.

Yield: 220 mg (9% of theoretical)
ESI-MS: m/z=351 (M+H)$^+$
$R_t$ (HPLC): 0.78 min (method A)

The enantiomeric (S) compound may be obtained analogously to the method of synthesis described above using the corresponding (S)-configured starting component.

Intermediate 17 tert-butyl (3R)-(3,5-difluorophenyl)-5-oxo-12-oxa-1,4-diaza-dispiro[5.2.5.2]hexadecane-1-carboxylate

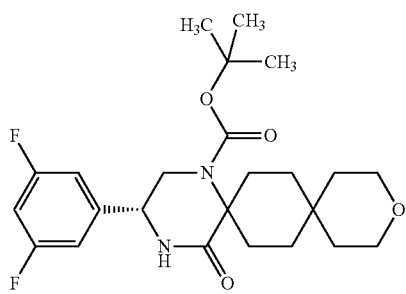 [SMILES: CC(C)(C)OC(=O)N1C[C@@H](c2cc(F)cc(F)c2)NC(=O)C12CCC1(CCOCC1)CC2]

687 mg (3.15 mmol) di-tert-butyldicarbonate were added at RT to 220 mg (0.63 mmol) (3R)-(3,5-difluorophenyl)-12-oxa-1,4-diaza-dispiro[5.2.5.2]-hexadecan-5-one and 0.10 ml (0.60 mmol) DIPEA in 10 ml ACN. After 4 h at 60° C. another 687 mg di-tert-butyldicarbonate were added. After another 3 h at 60° C., 687 mg of di-tert-butyldicarbonate were added and the mixture was stirred overnight at 60° C. The reaction mixture was evaporated down. The residue was crystallised with diisopropylether/petroleum ether. The solid was suction filtered, washed with diisopropylether/petroleum ether and dried.

Yield: 83 mg (29% of theoretical)
ESI-MS: m/z=451 (M+H)$^+$
$R_t$ (HPLC): 1.65 min (method A)

The enantiomeric (S) compound may be obtained analogously to the method of synthesis described above using the corresponding (S)-configured starting component.

Intermediate 18 tert-butyl (3R)-(3,5-difluorophenyl)-4-methoxycarbonylmethyl-5-oxo-12-oxa-1,4-diaza-dispiro[5.2.5.2]-hexadecane-1-carboxylate

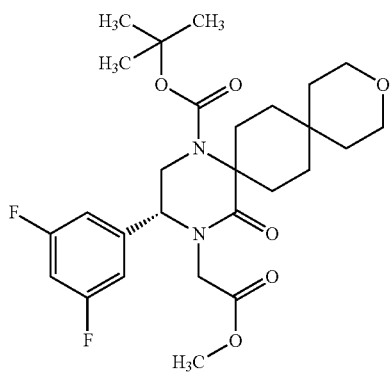 [SMILES: COC(=O)CN1C(=O)C2(CCC3(CCOCC3)CC2)N(C(=O)OC(C)(C)C)C[C@H]1c1cc(F)cc(F)c1]

Under a nitrogen atmosphere 9 mg (0.20 mmol) sodium hydride were added at 0° C. to 80 mg (0.18 mmol) tert-butyl (3R)-(3,5-difluorophenyl)-5-oxo-12-oxa-1,4-diaza-dispiro[5.2.5.2]-hexadecane-1-carboxylate in 15 ml DMF. After 20 min at 0° C. 20 µl (0.20 mmol) methyl bromoacetate were added. The reaction mixture was stirred for 30 min at 0° C. and for 5 h at RT. The mixture was poured onto water and extracted twice with ethyl acetate. The combined organic phases were washed with water, dried and evaporated down.

Yield: 83 mg (89% of theoretical)
ESI-MS: m/z=523 (M+H)$^+$
$R_t$ (HPLC): 1.75 min (method A)

The enantiomeric (S) compound may be obtained analogously to the method of synthesis described above using the corresponding (S)-configured starting component.

Intermediate 19 tert-butyl 4-carboxymethyl-(3R)-(3,5-difluorophenyl)-5-oxo-12-oxa-1,4-diaza-dispiro[5.2.5.2]-hexadecane-1-carboxylate

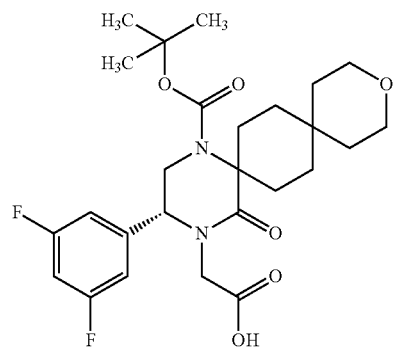 [SMILES: CC(C)(C)OC(=O)N1C[C@@H](c2cc(F)cc(F)c2)N(CC(=O)O)C(=O)C12CCC1(CCOCC1)CC2]

4 mg (0.18 mmol) lithium hydroxide were added to 80 mg (0.15 mmol) tert-butyl (3R)-(3,5-difluorophenyl)-4-methoxycarbonylmethyl-5-oxo-12-oxa-1,4-diaza-dispiro[5.2.5.2]hexadecane-1-carboxylate in 5 ml THF and 1 ml of water and the mixture was stirred for 2 h at RT. The mixture was adjusted to pH 7 with a 0.1M hydrochloric acid, evaporated down and dried.

Yield: 78 mg (quantitative)
ESI-MS: m/z=507 (M−H)$^−$
$R_t$ (HPLC): 1.56 min (method A)

The enantiomeric (S) compound may be obtained analogously to the method of synthesis described above using the corresponding (S)-configured starting component.

Intermediate 20

(S)-5-amino-1,3-dihydrospiro[indene-2,3-pyrrolo[2,3-b]pyridin]-2'(1'H)-one

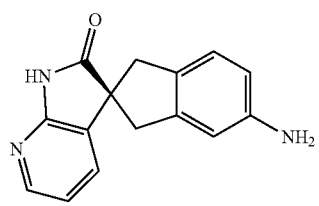 [SMILES: Nc1ccc2c(c1)C[C@]1(C2)C(=O)Nc2ncccc21]

This compound and its precursors were synthesised analogously to WO 2007/061677.

Intermediate 21

(R)-5-amino-1,3-dihydrospiro[inden-2,3'-pyrrolo[2,3-b]pyridin]-2'(1'H)-one

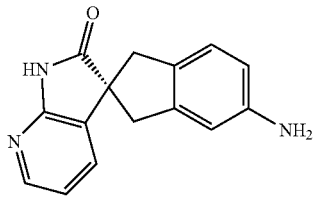 [SMILES: Nc1ccc2c(c1)C[C@@]1(C2)C(=O)Nc2ncccc21]

This compound and its precursors were synthesised analogously to WO 2007/061677.

Intermediate 22

2-bromo-1-(3,5-difluoro-phenyl)-ethanone oxime

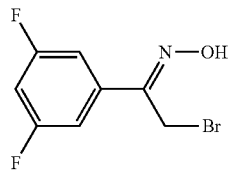 [SMILES: O/N=C(\CBr)c1cc(F)cc(F)c1]

34.5 g (146.8 mmol) 3,5-difluorophenacylbromide, 30.6 g (440.4 mmol) hydroxylamine-hydrochloride, 44.0 ml of water and 320.0 mL methanol were stirred overnight at RT. The reaction mixture was concentrated by rotary evaporation using the rotary evaporator and mixed with 150 mL water and extracted twice with ethyl acetate. The combined organic phases were washed with water, dried and evaporated to dryness by rotary evaporation.
Yield: 32.7 g (89% of theoretical)

Intermediate 23

3-(3-methoxyphenyl-1)-8,11-dioxa-1,4-diazaspiro[5.6]dodecan-5-one

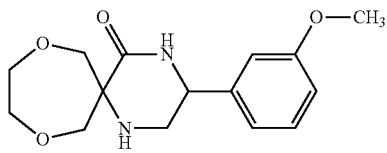 [SMILES: COc1cccc(C2CNC3(COCCOC3)C(=O)N2)c1]

32 mg (0.14 mmol) benzyltriethylammonium chloride and 0.50 g 1-(3-methoxyphenyl)ethan-1,2-diamine (prepared analogously to DE2240256) in 5 ml DCM were cooled to 0° C. and combined with 1.04 ml (19 mmol) 50% aqueous sodium hydroxide solution. At this temperature 0.44 g of 80% (3 mmol) [1,4]dioxepan-6-one and 0.37 ml (4.6 mmol) trichloromethane in 4 ml DCM were added dropwise. The reaction mixture was left to warm up to RT overnight. The reaction was acidified with a 4N hydrochloric acid solution and the phases were separated. The aqueous phase was made basic with a 4N sodium hydroxide solution and extracted with EtOAc. The organic phase was dried and evaporated down. The residue was purified by flash chromatography.
Yield: 390 mg (45% of theoretical)
ESI-MS: m/z=293 (M−H)⁻
$R_t$ (HPLC): 0.63 min (method A)

Intermediate 24 tert-butyl 3-(3-methoxyphenyl)-5-oxo-8,11-dioxa-1,4-diazaspiro[5.6]dodecane-1-carboxylate

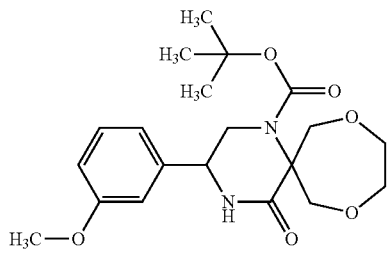 [SMILES: COc1cccc(C2CN(C(=O)OC(C)(C)C)C3(COCCOC3)C(=O)N2)c1]

0.44 ml (2.6 mmol) DIPEA and 0.40 g (1.8 mmol) di-tert-butyldicarbonate were added to 0.38 g (1.3 mmol) 3-(3-methoxyphenyl)-8,11-dioxa-1,4-diazaspiro[5.6]dodecan-5-one in 10 ml THF. The reaction was refluxed overnight. The reaction mixture was evaporated down. The residue was triturated with diethyl ether. The solid was suction filtered, washed with diethyl ether and dried.
Yield: 345 mg (69% of theoretical)
ESI-MS: m/z=393 (M+H)⁺

Intermediate 25 tert-butyl 3-(3-methoxyphenyl)-5-oxo-8,11-dioxa-1,4-diazaspiro[5.6]dodecane-1-carboxylate

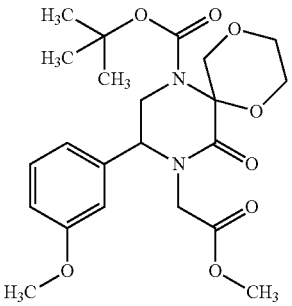 [SMILES: COC(=O)CN1C(=O)C2(COCCO2)N(C(=O)OC(C)(C)C)CC1c1cccc(OC)c1]

30 mg (0.91 mmol) sodium hydride were added to 0.33 g (0.83 mmol) tert-butyl 3-(3-methoxyphenyl)-5-oxo-8,11-dioxa-1,4-diazaspiro[5.6]dodecane-1-carboxylate in 5 ml DMF. After 5 min at RT 89 µl (0.91 mmol) methyl bromoacetate were added and then the reaction mixture was stirred for 1 h at RT. The reaction mixture was poured onto ice water and extracted with ethyl acetate. The organic phase was washed with water, dried and evaporated down.

Intermediate 26

2-(1-(tert-butoxycarbonyl)-3-(3-methoxyphenyl)-5-oxo-8,11-dioxa-1,4-diazaspiro[5.6]-dodecan-4-yl)ethanoic acid

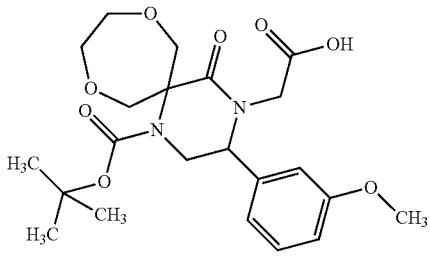 [SMILES: COc1cccc(C2CN(C(=O)OC(C)(C)C)C3(COCCOC3)C(=O)N2CC(=O)O)c1]

2.5 ml (2.5 mmol) of a 1N aqueous sodium hydroxide solution were added to 0.38 g (0.82 mmol) tert-butyl (3-(3-methoxyphenyl)-5-oxo-8,11-dioxa-1,4-diazaspiro[5.6]dodecane-1-carboxylate in 5 ml MeOH. After 1 h MeOH was distilled off and the aqueous solution was acidified with 1N hydrochloric acid. The aqueous phase was extracted with ethyl acetate. The ethyl acetate phase was dried and evaporated down.

Yield: 360 mg (98% of theoretical)
ESI-MS: m/z=451 (M+H)+
$R_t$ (HPLC): 1.24 min (method A)

Intermediate 27 tert-butyl 3-(3-methoxyphenyl)-5-oxo-4-(2-oxo-2-((R)-2'-oxo-1,1',2',3-tetrahydrospiro[inden-2,3'-pyrrolo[2,3-b]pyridin]-5-ylamino)ethyl)-8,11-dioxa-1,4-diazaspiro[5.6]dodecane-1-carboxylate

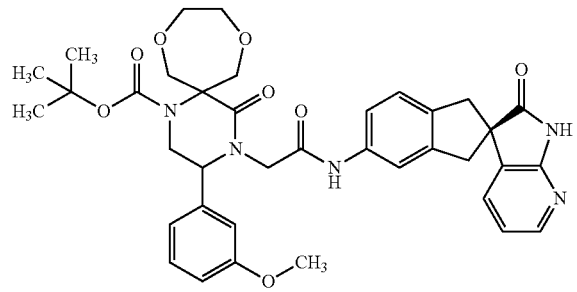 [SMILES: COc1cccc(C2CN(C(=O)OC(C)(C)C)C3(COCCOC3)C(=O)N2CC(=O)Nc2ccc3c(c2)C[C@@]2(C3)C(=O)Nc3ncccc32)c1]

0.44 g (0.81 mmol) 80% 2-(1-(tert-butoxycarbonyl)-3-(3-methoxyphenyl)-5-oxo-8,11-dioxa-1,4-diazaspiro[5.6]dodecan-4-yl)ethanoic acid in 10 ml DMF were combined with 0.75 g (2.0 mmol) HATU and 0.34 ml (2.4 mmol) TEA and stirred for 10 min at RT. Then 0.25 g (0.98 mmol) (S)-5-amino-1,3-dihydrospiro[inden-2,3'-pyrrolo[2,3-b]pyridin]-2'(1'H)-one were added and the mixture was stirred overnight at RT. The reaction mixture was poured onto water. The precipitate formed was suction filtered, washed with water and dried.

Yield: 610 mg (99% of theoretical)
ESI-MS: m/z=682 (M−H)−
$R_t$ (HPLC): 1.39 min (method A)

Intermediate 28

5-amino-6-chloro-1,3-dihydrospiro[inden-2,3'-pyrrolo[2,3-b]pyridin]-2'(1'H)-one

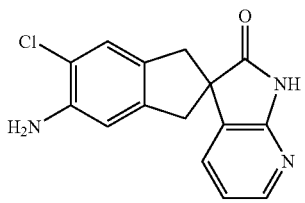 [SMILES: Nc1cc2c(cc1Cl)CC1(C2)C(=O)Nc2ncccc21]

0.50 g (2.0 mmol) 5-amino-1,3-dihydrospiro[inden-2,3'-pyrrolo[2,3-b]pyridin]-2'(1'H)-one in 20 ml DCM were combined with 0.27 g (2 mmol) N-chlorosuccinimide versetzt and stirred for 5 h at RT. The mixture was evaporated down and the residue was purified by HPLC.

Yield: 0.14 g (25% of theoretical)
ESI-MS: m/z=286 (M+H)+
$R_t$ (HPLC): 1.10 min (method A)

Intermediate 29

(3R)-tert-butyl 4-(2-(5-chloro-2'-oxo-1,1',2',3-tetrahydrospiro[inden-2,3'-pyrrolo[2,3-b]pyridin]-6-ylamino)-2-oxoethyl)-3-(3,5-difluorophenyl)-5-oxo-8,11-dioxa-1,4-diazaspiro[5.6]dodecane-1-carboxylate

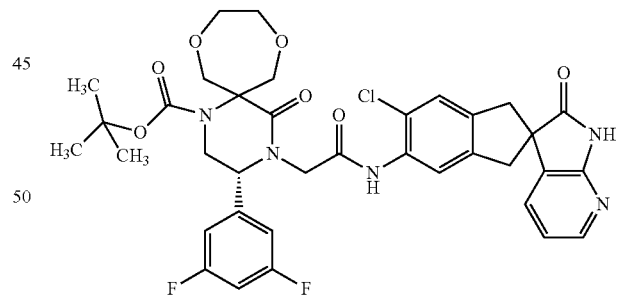

0.11 g (0.24 mmol) (R)-2-(1-(tert-butoxycarbonyl)-3-(3,5-difluorophenyl)-5-oxo-8,11-dioxa-1,4-diazaspiro[5.6]dodecan-4-yl)acetic acid in 4 ml DMF were combined with 0.11 g (0.3 mmol) HATU and 0.07 ml (0.5 mmol) TEA and stirred for 5 min at RT. Then 70 mg (0.24 mmol) 5-amino-6-chloro-1,3-dihydrospiro[inden-2,3'-pyrrolo[2,3-b]pyridin]-2'(1'H)-one were added and the mixture was stirred overnight at RT. The reaction mixture was purified by HPLC.

Yield: 40 mg (23% of theoretical)
ESI-MS: m/z=725 (M+H)+
$R_t$ (HPLC): 1.5 min (method A)

Intermediate 30

(R)-3-phenyl-8,11-dioxa-1,4-diazaspiro[5.6]dodecan-5-one

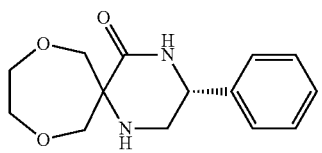 [SMILES: O=C1N[C@H](c2ccccc2)CNC12COCCOC2]

0.63 g (3.0 mmol) (1S)1-phenylethane dihydrochloride were placed with 32 mg (0.14 mmol) benzyltriethylammonium chloride in 6 ml dichloromethane and cooled with ice/acetone. Then 1.0 ml (19 mmol) of a 50% sodium hydroxide solution were added. At 0° C. 0.44 g (3 mmol) 80% [1.4]dioxepan-6-one together with 0.37 ml (4.6 mmol) chloroform and 5 ml dichloromethane were added dropwise. The mixture was left overnight to warm up to RT. Then the reaction mixture was acidified with an aqueous 4N hydrochloric acid solution. The phases were separated. The aqueous phase was made alkaline with a 4N sodium hydroxide solution and extracted with ethyl acetate. The combined organic phases were dried and evaporated to dryness by rotary evaporation. Purification was carried out by flash chromatography.

Yield: 250 mg (32% of theoretical)

ESI-MS: m/z=263 (M+H)$^+$ $R_t$ (HPLC): 0.44 min (method A)

Intermediate 31

(R)-tert-butyl 5-oxo-3-phenyl-8,11-dioxa-1,4-diazaspiro[5.6]dodecane-1-carboxylate

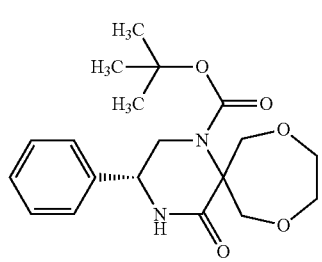 [SMILES: CC(C)(C)OC(=O)N1C[C@@H](c2ccccc2)NC(=O)C12COCCOC2]

0.31 ml (1.8 mmol) DIPEA and 0.28 g (1.2 mmol) di-tert-butyldicarbonate were added to 0.22 g (0.84 mmol) (3R)-3-phenyl-8,11-dioxa-1,4-diazaspiro[5.6]dodecan-5-one in 10 ml THF. The reaction was refluxed overnight. The reaction mixture was evaporated down.

The residue was triturated with diethyl ether. The solid was suction filtered, washed with diethyl ether and dried.

Yield: 190 mg (63% of theoretical)

ESI-MS: m/z=363 (M+H)$^+$ $R_t$ (HPLC): 1.26 min (method A)

Intermediate 32

(R)-tert-butyl 4-(2-methoxy-2-oxoethyl)-5-oxo-3-phenyl-8,11-dioxa-1,4-diazaspiro[5.6]dodecane-1-carboxylate

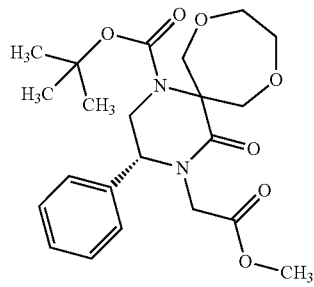 [SMILES: COC(=O)CN1C(=O)C2(COCCOC2)N(C(=O)OC(C)(C)C)C[C@H]1c1ccccc1]

24 mg (0.55 mmol) sodium hydride were added to 0.18 g (0.5 mmol) (3R)-tert-butyl 5-oxo-3-phenyl-8,11-dioxa-1,4-diazaspiro[5.6]dodecane-1-carboxylate in 3 ml DMF. After 5 min at RT 54 µl (0.91 mmol) methyl bromoacetate were added and then the reaction mixture was stirred for 1 h at RT. The reaction was poured onto ice water and extracted with ethyl acetate. The organic phase was washed with water, dried and evaporated down.

Yield: 215 mg (quantitative)

ESI-MS: m/z=435 (M+H)$^+$ $R_t$ (HPLC): 1.33 min (method A)

Intermediate 33

(R)-2-(1-(tert-butoxycarbonyl)-5-oxo-3-phenyl-8,11-dioxa-1,4-diazaspiro[5.6]dodecan-4-yl)ethanoic acid

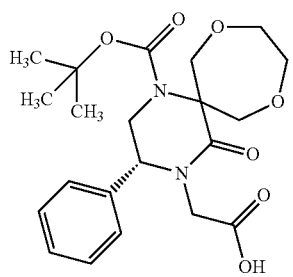 [SMILES: CC(C)(C)OC(=O)N1C[C@@H](c2ccccc2)N(CC(=O)O)C(=O)C12COCCOC2]

24 mg (1.0 mmol) lithium hydroxide in 1 ml of water were added to 0.22 g (0.5 mmol) (R)-tert-butyl 4-(2-methoxy-2-oxoethyl)-5-oxo-3-phenyl-8,11-dioxa-1,4-diazaspiro[5.6]dodecane-1-carboxylate in 10 ml MeOH. The reaction mixture was stirred overnight at RT and then the MeOH was distilled off. The residue was mixed with water and acidified with an aqueous 4N hydrochloric acid. The aqueous phase was extracted with ethyl acetate. The ethyl acetate phase was dried and evaporated down.

Yield: 210 mg (quantitative)

ESI-MS: m/z=421 (M+H)$^+$ $R_t$ (HPLC): 1.23 min (method A)

Intermediate 34

3-(4-fluorophenyl)-8,11-dioxa-1,4-diazaspiro[5.6]dodecan-5-one

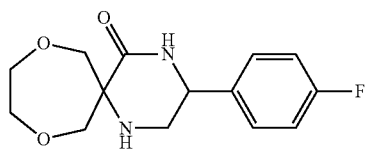 [SMILES: O=C1NC(c2ccc(F)cc2)CNC12COCCOC2]

0.68 g (3.0 mmol) 1-(4-fluorophenyl)ethane-1,2-diamine dihydrochloride were placed with 32 mg (0.14 mmol) benzyltriethylammonium chloride in 6 ml dichloromethane and cooled with ice/acetone. Then 1.0 ml (19 mmol) 50% sodium hydroxide solution were added. At 0° C. 0.44 g (3.0 mmol) 80% [1,4]dioxepan-6-one were added dropwise together with 0.37 ml (4.6 mmol) chloroform and 5 ml dichloromethane. The reaction mixture was left overnight to warm up to RT. Then the reaction mixture was acidified with an aqueous 4N hydrochloric acid solution. The phases were separated. The aqueous phase was made alkaline with a 4N sodium hydroxide solution and extracted with ethyl acetate. The combined organic phases were dried and evaporated to dryness by rotary evaporation. Purification was carried out by flash chromatography.

Yield: 260 mg (31% of theoretical)

ESI-MS: m/z=281 (M+H)$^+$ $R_t$ (HPLC): 0.56 min (method A)

Intermediate 35 tert-butyl-3-(4-fluorophenyl)-5-oxo-8,11-dioxa-1,4-diazaspiro[5.6]dodecane-1-carboxylate

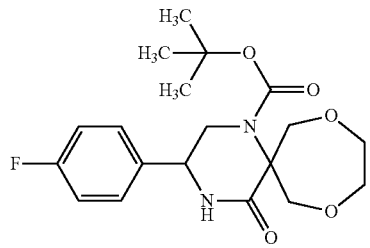 [SMILES: CC(C)(C)OC(=O)N1CC(c2ccc(F)cc2)NC(=O)C12COCCOC2]

0.31 ml (1.8 mmol) DIPEA and 0.28 g (1.2 mmol) di-tert-butyldicarbonate were added to 0.25 g (0.89 mmol) 3-(4-fluorophenyl)-8,11-dioxa-1,4-diazaspiro[5.6]dodecan-5-one in 10 ml THF. The reaction was heated for 2 h at RT and refluxed overnight. The reaction mixture was evaporated down. The residue was triturated with diethyl ether. The solid was suction filtered, washed with diethyl ether and dried.

Yield: 240 mg (71% of theoretical)

ESI-MS: m/z=381 (M+H)$^+$ $R_t$ (HPLC): 1.28 min (method A)

Intermediate 36 tert-butyl-3-(4-fluorophenyl)-4-(2-methoxy-2-oxoethyl)-5-oxo-8,11-dioxa-1,4-diazaspiro[5.6]dodecane-1-carboxylate

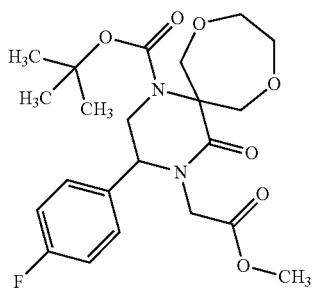 [SMILES: COC(=O)CN1C(=O)C2(COCCOC2)N(C(=O)OC(C)(C)C)CC1c1ccc(F)cc1]

28 mg (0.66 mmol) sodium hydride were added to 0.23 g (0.6 mmol) tert-butyl-3-(4-fluorophenyl)-5-oxo-8,11-dioxa-1,4-diazaspiro[5.6]dodecane-1-carboxylate in 5 ml DMF. After 5 min at RT 64 µl (0.91 mmol) methyl bromoacetate were added dropwise and then the reaction mixture was stirred for 1 h at RT. The reaction was poured onto ice water and extracted with ethyl acetate. The organic phase was washed with water, dried and evaporated down.

Yield: 290 mg (quantitative)

ESI-MS: m/z=453 (M+H)$^+$ $R_t$ (HPLC): 1.39 min (method A)

Intermediate 37

2-(1-(tert-butoxycarbonyl)-3-(4-fluorophenyl)-5-oxo-8,11-dioxa-1,4-diazaspiro[5.6]dodecan-4-yl)ethanoic acid

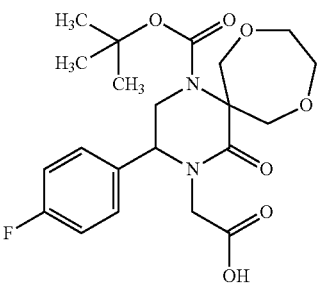 [SMILES: CC(C)(C)OC(=O)N1CC(c2ccc(F)cc2)N(CC(=O)O)C(=O)C12COCCOC2]

2.0 ml (2.0 mmol) of a 1N aqueous sodium hydroxide solution were added to 0.29 mg (0.61 mmol) tert-butyl 3-(4-fluorophenyl)-4-(2-methoxy-2-oxoethyl)-5-oxo-8,11-dioxa-1,4-diazaspiro[5.6]dodecane-1-carboxylate in 5 ml MeOH. After 1 h at RT MeOH was distilled off and the aqueous solution was acidified with 1N hydrochloric acid. The aqueous phase was extracted with ethyl acetate. The ethyl acetate phase was dried and evaporated down.

Yield: 265 mg (quantitative)

ESI-MS: m/z=439 (M+H)$^+$ $R_t$ (HPLC): 1.25 min (method A)

Intermediate 38

2-(3-(4-fluorophenyl)-5-oxo-8,11-dioxa-1,4-diazaspiro[5.6]dodecan-4-yl)-N-((R)-2'-oxo-1,1',2',3-tetrahydrospiro[inden-2,3'-pyrrolo[2,3-b]pyridin]-5-yl)acetamide

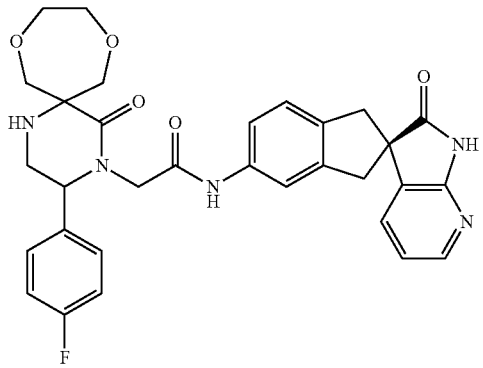

0.26 g (0.6 mmol) 2-(1-(tert-butoxycarbonyl)-3-(4-fluorophenyl)-5-oxo-8,11-dioxa-1,4-diazaspiro[5.6]dodecan-4-yl)ethanoic acid in 10 ml DMF were combined with 0.46 g (1.2 mmol) HATU and 0.20 ml (1.4 mmol) TEA and stirred for 10 min at RT. Then 0.17 g (0.66 mmol) (S)-5-amino-1,3-dihydrospiro[inden-2,3'-pyrrolo[2,3-b]pyridin]-2'(1'H)-one were added and the mixture was stirred overnight at RT. The reaction mixture was poured onto water. The precipitate formed was suction filtered, washed with water and dried.

Yield: 370 mg (92% of theoretical)
ESI-MS: m/z=672 (M–H)⁻
R_t (HPLC): 1.40 min (method A)

Intermediate 39

2-(3-(4-fluorophenyl)-5-oxo-8,11-dioxa-1,4-diazaspiro[5.6]dodecan-4-O—N—((R)-2'-oxo-1,1',2',3-tetrahydrospiro[inden-2,3'-pyrrolo[2,3-b]pyridin]-5-yl)acetamide

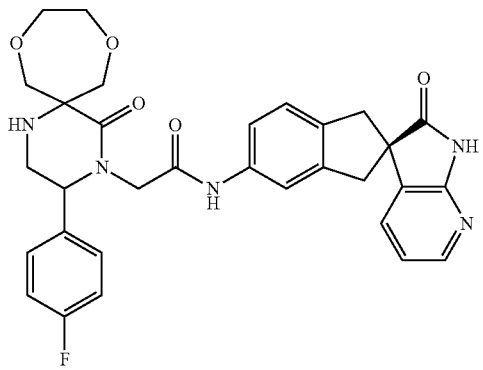

0.36 g (0.53 mmol) 2-(3-(4-fluorophenyl)-5-oxo-8,11-dioxa-1,4-diazaspiro[5.6]dodecan-4-yl)-N—((R)-2'-oxo-1,1',2',3-tetrahydrospiro[inden-2,3'-pyrrolo[2,3-b]pyridin]-5-yl)acetamide in 5 ml of methanol were combined with 10 ml of a 1.25 M methanolic hydrochloric acid and stirred for 0.5 h at RT and 3 h at 50° C. The reaction mixture was concentrated by rotary evaporation, mixed with water and neutralised with a saturated NaHCO₃ solution. The precipitate formed was suction filtered, washed with water and dried.

Yield: 220 mg (73% of theoretical)
ESI-MS: m/z=572 (M+H)⁺
R_t (HPLC): 1.02 min (method A)

Intermediate 40

3-(3-fluorophenyl)-8,11-dioxa-1,4-diazaspiro[5.6]dodecan-5-one

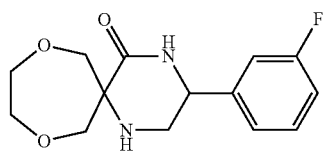 [SMILES: O=C1NC(c2cccc(F)c2)CNC12COCCOC2]

0.47 g (2.1 mmol) 1-(3-fluorophenyl)ethan-1,2-diamine dihydrochloride were placed with 23 mg (0.10 mmol) benzyltriethylammonium chloride in 50 ml dichloromethane and cooled with ice/acetone. Then 0.71 ml (14 mmol) of a 50% sodium hydroxide solution were added. At 0° C. 0.23 g (2 mmol) [1,4]dioxepan-6-one were added dropwise together with 0.24 ml (4.6 mmol) chloroform and 20 ml dichloromethane. The mixture was left overnight to warm up to RT. Then the reaction mixture was cooled to 0° C. and adjusted to pH 1 with a 6N aqueous hydrochloric acid solution. The phases were separated. The aqueous phase was made alkaline with a 4N sodium hydroxide solution and extracted with DCM. The combined organic phases were dried and evaporated to dryness by rotary evaporation.

Yield: 250 mg (44% of theoretical)
ESI-MS: m/z=281 (M+H)⁺
R_t (HPLC): 0.62 min (method A)

Intermediate 41 tert-butyl 3-(3-fluorophenyl)-5-oxo-8,11-dioxa-1,4-diazaspiro[5.6]dodecane-1-carboxylate

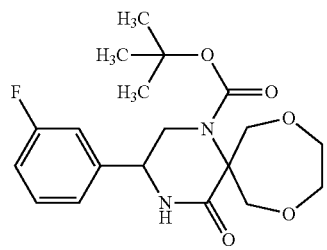 [SMILES: CC(C)(C)OC(=O)N1CC(c2cccc(F)c2)NC(=O)C12COCCOC2]

0.33 ml (1.9 mmol) DIPEA and 0.30 g (1.4 mmol) di-tert-butyldicarbonate were added to 0.25 g (0.84 mmol) 3-(3-fluorophenyl)-8,11-dioxa-1,4-diazaspiro[5.6]dodecan-5-one in 30 ml THF. The reaction mixture was refluxed overnight. Then a further 0.30 g di-tert-butyldicarbonate were added and the mixture was refluxed for 12 h. Then another 0.30 g di-tert-butyldicarbonate were added and the mixture was refluxed overnight. The reaction mixture was evaporated down. The residue was triturated with diisopropylether. The solid was suction filtered, washed with diisopropylether and dried.

Yield: 210 mg (62% of theoretical)
ESI-MS: m/z=381 (M+H)⁺
R_t (HPLC): 1.274 min (method A)

Intermediate 42 tert-butyl 3-(3-fluorophenyl)-4-(2-methoxy-2-oxoethyl)-5-oxo-8,11-dioxa-1,4-diazaspiro[5.6]dodecane-1-carboxylate

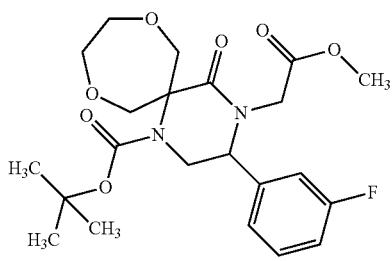 [SMILES: COC(=O)CN1C(=O)C2(COCCOC2)N(C(=O)OC(C)(C)C)CC1c1cccc(F)c1]

28 mg (0.66 mmol) sodium hydride were added to 0.21 g (0.55 mmol) tert-butyl 3-(3-fluorophenyl)-5-oxo-8,11-dioxa-1,4-diazaspiro[5.6]dodecane-1-carboxylate in 20 ml DMF. After 20 min at RT 63 µl (0.65 mmol) methyl bromoacetate were added dropwise at 0° C. Then the mixture was stirred for 30 min in the ice bath and then for 5 h at RT. The reaction mixture was poured onto water poured and extracted with ethyl acetate. The organic phase was washed with water, dried and evaporated down.
Yield: 250 mg (quantitative)
ESI-MS: m/z=453 (M+H)⁺
R_t (HPLC): 1.386 min (method A)

Intermediate 43

2-(1-(tert-butoxycarbonyl)-3-(3-fluorophenyl)-5-oxo-8,11-dioxa-1,4-diazaspiro[5.6]dodecan-4-yl)ethanoic acid

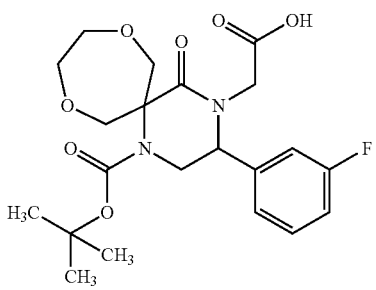 [SMILES: CC(C)(C)OC(=O)N1CC(c2cccc(F)c2)N(CC(=O)O)C(=O)C12COCCOC2]

15 mg (0.62 mmol) lithium hydroxide were added to 0.25 g (0.55 mmol) tert-butyl 3-(3-fluorophenyl)-4-(2-methoxy-2-oxoethyl)-5-oxo-8,11-dioxa-1,4-diazaspiro[5.6]dodecane-1-carboxylate in 5 ml THF and 1 ml of water. The mixture was stirred for 2 h at RT and then the MeOH was distilled off. The residue was mixed with water and acidified with formic acid. The aqueous phase was extracted with ethyl acetate. The ethyl acetate phase was dried and evaporated down.
Yield: 230 mg (quantitative)
ESI-MS: m/z=439 (M+H)⁺
R_t (HPLC): 1.253 min (method A)

Intermediate 44

3-amino-5,7-dihydrospiro[cyclopenta[b]pyridin-6,3'-pyrrolo[2,3-b]pyridin]-2'(1'H)-one

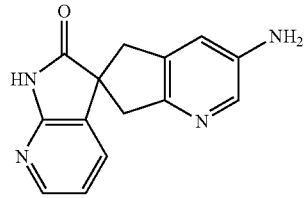 [SMILES: Nc1cnc2c(c1)CC1(C2)C(=O)Nc2ncccc21]

This compound and its precursors were synthesised analogously to US 2007/265225.

Intermediate 45

(3R)-tert-butyl 3-(3,5-difluorophenyl)-5-oxo-4-(2-oxo-2-(2'-oxo-1',2',5,7-tetrahydrospiro[cyclopenta[b]pyridin-6,3'-pyrrolo[2,3-b]pyridin]-3-ylamino)ethyl)-8,11-dioxa-1,4-diaza-spiro[5.6]dodecane-1-carboxylate

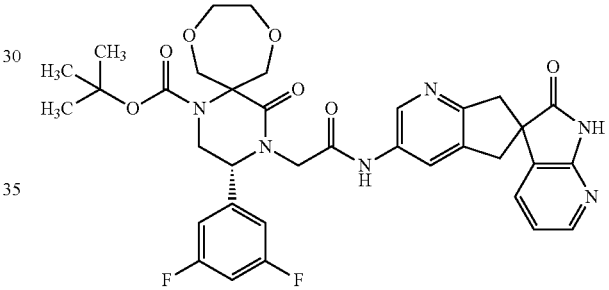

0.13 g (0.28 mmol) tert-butyl (R)-4-carboxymethyl-3-(3,5-difluoro-phenyl)-5-oxo-8,11-dioxa-1,4-diaza-spiro[5.6]dodecane-1-carboxylate in 2 ml DMF were combined with 0.11 g (0.29 mmol) HATU and 0.08 ml (0.60 mmol) TEA and stirred for 3 min at RT. Then 72 mg (0.28 mmol) 3-amino-5,7-dihydrospiro[cyclopenta-[b]pyridin-6.3'-pyrrolo[2,3-b]pyridin]-2'(1'H)-one were added and the mixture was stirred overnight at RT. The reaction mixture was poured onto saturated sodium hydrogen carbonate solution. The precipitate formed was suction filtered, washed with water and dried.
Yield: 180 mg (92% of theoretical)
ESI-MS: m/z=691 (M+H)⁺
R_t (HPLC): 1.30 min (method A)

Intermediate 46 ethyl (rac)-benzylamino-(tetrahydro-pyran-4-yl)-acetate

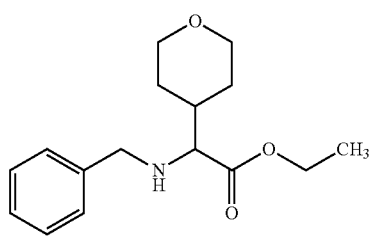 [SMILES: CCOC(=O)C(NCc1ccccc1)C1CCOCC1]

0.53 ml (4.5 mmol) benzylbromide, 0.85 g (4.5 mmol) ethyl (rac)-amino-(tetrahydropyran-4-yl)-acetate and 1.9 g (13.7 mmol) potassium carbonate in 10 mL DMF were stirred for 2 h at 100° C. After cooling the mixture was mixed with water and extracted three times with ethyl acetate. The combined organic phases were extracted with saturated, aqueous saline solution, three times with 0.5 M hydrochloric acid and once more with saturated saline solution. The combined aqueous phases were adjusted to pH 9 with conc. aqueous ammonia solution and extracted three times with dichloromethane. The combined organic phases were washed with saturated saline solution, dried and concentrated by rotary evaporation.

Yield: 0.39 g (31% of theoretical)

ESI-MS: m/z=278 (M+H)$^+$

R$_t$ (HPLC): 0.813 min (method A)

Intermediate 47 ethyl (rac)-E/Z-{benzyl-[2-(3,5-difluoro-phenyl)-2-hydroxyimino-ethyl]-amino}-(tetrahydro-pyran-4-yl)-acetate

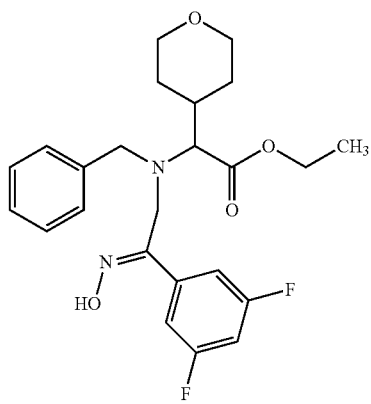 [SMILES: CCOC(=O)C(C1CCOCC1)N(C/C(=N/O)c1cc(F)cc(F)c1)Cc1ccccc1]

0.35 g (1.4 mmol) 2-bromo-1-(3,5-difluoro-phenyl)-ethanone oxime, 0.39 g (1.4 mmol) ethyl (rac)-benzylamino-(tetrahydro-pyran-4-yl)-acetate and 0.25 g (1.8 mmol) potassium carbonate in 10 ml THF were stirred overnight at RT. The reaction mixture was diluted with water and extracted four times with ethyl acetate. The combined organic phases were washed with water, dried, filtered and concentrated by rotary evaporation. The residue was purified by HPLC. The product-containing fractions were combined and the organic solvent was eliminated. The aqueous solution was made alkaline with a saturated sodium hydrogen carbonate solution, extracted twice with ethyl acetate, the organic phases were combined, dried, filtered and concentrated by rotary evaporation.

Yield: 0.24 g (38% of theoretical)

ESI-MS: m/z=447 (M+H)$^+$

R$_t$ (HPLC): 1.64/1.68 min (method A)

Intermediate 48

6-(3,5-difluorophenyl)-3-(tetrahydro-2H-pyran-4-yl)piperazin-2-one

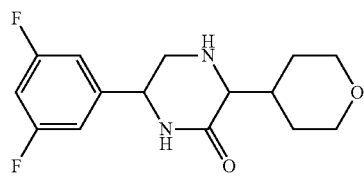 [SMILES: O=C1NC(c2cc(F)cc(F)c2)CNC1C1CCOCC1]

4.2 g (9.4 mmol) ethyl (rac)-E/Z-{benzyl-[2-(3,5-difluorophenyl)-2-hydroxyimino-ethyl]-amino}-(tetrahydro-pyran-4-yl)-acetate in 100 ml of ethanol were hydrogenated under a hydrogen atmosphere together with 0.80 g of 10% palladium charcoal for 20 h at 50° C. More catalyst was added and the mixture was hydrogenated at 70° C. The catalyst was removed by suction filtering and the solvent was evaporated down. The residue was dissolved in ethanol, combined with 2 g sodium hydrogen carbonate and refluxed overnight. After cooling the insoluble constituents of the reaction mixture were suction filtered. The filtrate was evaporated down. The residue was purified by flash chromatography. The fractions were evaporated down and the residue was triturated with diisopropylether. The precipitate was suction filtered and dried.

Yield: 1.24 g (44% of theoretical)

ESI-MS: m/z=297 (M+H)$^+$

R$_t$ (HPLC): 0.476/0.635 min (method A)

Intermediate 49 tert-butyl-5-(3,5-difluorophenyl)-3-oxo-2-(tetrahydro-2H-pyran-4-yl)piperazine-1-carboxylate

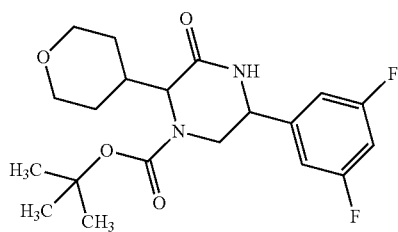 [SMILES: CC(C)(C)OC(=O)N1CC(c2cc(F)cc(F)c2)NC(=O)C1C1CCOCC1]

0.71 ml (4.1 mmol) DIPEA and 4.6 g (21.0 mmol) di-tert-butyldicarbonate were added to 1.2 g (4.1 mmol) 6-(3,5-difluorophenyl)-3-(tetrahydro-2H-pyran-4-yl)piperazin-2-one in 50 ml acetonitrile. The reaction was stirred for 2 h at 60° C. The reaction mixture was evaporated down. The residue was purified by flash chromatography.

Yield: 0.3 g (19% of theory; isomer mixture 1) and 1.3 g (81% of theory; isomer mixture 2)

ESI-MS: m/z=397 (M+H)$^+$

R$_t$ (HPLC): 1.397/1.296 min (method A)

Intermediate 50a tert butyl 5-(3,5-difluorophenyl)-4-(2-methoxy-2-oxoethyl)-3-oxo-2-(tetrahydro-2H-pyran-4-yl)-piperazine-1-carboxylate (isomer mixture 1.1)

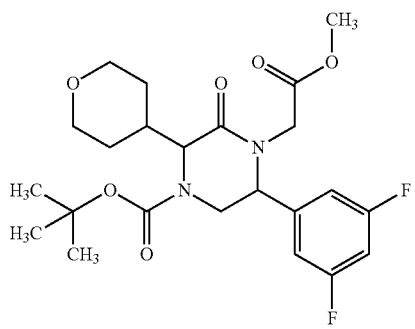 [SMILES: COC(=O)CN1C(=O)C(C2CCOCC2)N(C(=O)OC(C)(C)C)CC1c1cc(F)cc(F)c1]

At 0° C. 38 mg (0.86 mmol) sodium hydride were added to 0.30 g (0.76 mmol) tert-butyl 5-(3,5-difluorophenyl)-3-oxo-2-(tetrahydro-2H-pyran-4-yl)piperazine-1-carboxylate (isomer mixture 1) in 10 ml DMF. After 20 min, while cooling with an ice bath, 84 µl (0.86 mmol) methyl bromoacetate were added dropwise. Then the mixture was stirred for 30 min in the ice bath and for 5 h at RT. The reaction mixture was poured onto water and extracted with ethyl acetate. The organic phase was washed with water, dried and evaporated down.

Yield: 310 mg (87% of theory)
ESI-MS: m/z=469 (M+H)$^+$
$R_t$ (HPLC): 1.521 min (method A)

Intermediate 50b tert-butyl 5-(3,5-difluorophenyl)-4-(2-methoxy-2-oxoethyl)-3-oxo-2-(tetrahydro-2H-pyran-4-yl)-piperazine-1-carboxylate (isomer mixture 2.1)

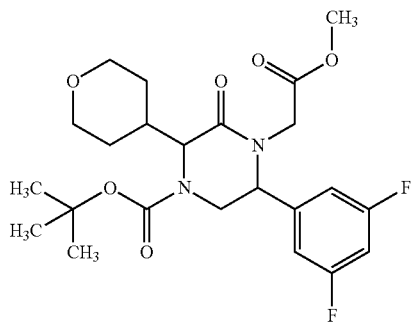 [SMILES: COC(=O)CN1C(=O)C(C2CCOCC2)N(C(=O)OC(C)(C)C)CC1c1cc(F)cc(F)c1]

At 0° C. 0.16 g (3.7 mmol) sodium hydride was added to 1.30 g (3.3 mmol) tert-butyl 5-(3,5-difluorophenyl)-3-oxo-2-(tetrahydro-2H-pyran-4-yl)piperazine-1-carboxylate (isomer mixture 2) in 20 ml DMF. After 20 min 0.36 ml (3.7 mmol) methyl bromoacetate were added dropwise while cooling with an ice bath. Then the mixture was stirred for 30 min in the ice bath and for 5 h at RT. The reaction mixture was poured onto water and extracted with ethyl acetate. The organic phase was washed with water, dried and evaporated down.

Yield: 0.87 g (57% of theory)
ESI-MS: m/z=469 (M+H)$^+$
$R_t$ (HPLC): 1.485 min (method A)

Intermediate 51a 2-(4-(tert-butoxycarbonyl)-6-(3,5-difluorophenyl)-2-oxo-3-(tetrahydro-2H-pyran-4-yl)-piperazin-1-yl)ethanoic acid (isomer mixture 1.1.1)

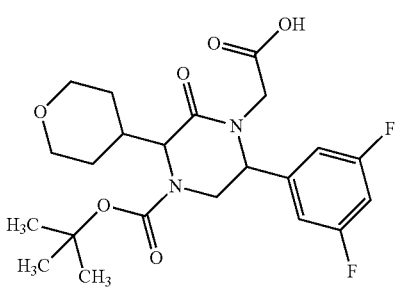 [SMILES: CC(C)(C)OC(=O)N1CC(c2cc(F)cc(F)c2)N(CC(=O)O)C(=O)C1C1CCOCC1]

12 mg (0.48 mmol) lithium hydroxide were added to 0.20 g (0.43 mmol) tert-butyl 5-(3,5-difluorophenyl)-4-(2-methoxy-2-oxoethyl)-3-oxo-2-(tetrahydro-2H-pyran-4-yl)piperazine-1-carboxylate (isomer mixture 1.1) in 5 ml THF and 1 ml of water. The mixture was stirred for 2 h at RT and then evaporated to dryness.

Yield: 200 mg (quantitative)
ESI-MS: m/z=455 (M+H)$^+$
$R_t$ (HPLC): 1.361 min (method A)

Intermediate 51b 2-(4-(tert-butoxycarbonyl)-6-(3,5-difluorophenyl)-2-oxo-3-(tetrahydro-2H-pyran-4-yl)-piperazin-1-yl)ethanoic acid (isomer mixture 2.1.1)

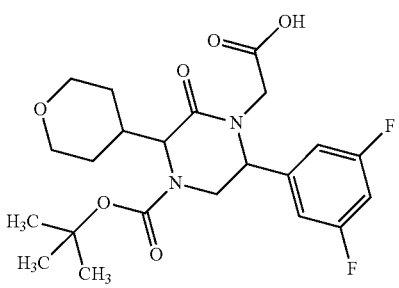 [SMILES: CC(C)(C)OC(=O)N1CC(c2cc(F)cc(F)c2)N(CC(=O)O)C(=O)C1C1CCOCC1]

12 mg (0.48 mmol) lithium hydroxide were added to 0.20 g (0.43 mmol) tert-butyl 5-(3,5-difluorophenyl)-4-(2-methoxy-2-oxoethyl)-3-oxo-2-(tetrahydro-2H-pyran-4-yl)piperazine-1-carboxylate (isomer mixture 2.1) in 5 ml THF and 1 ml of water. The mixture was stirred for 2 h at RT, adjusted to pH=7 with 0.1 M hydrochloric acid solution and then evaporated to dryness.

Yield: 200 mg (quantitative)
ESI-MS: m/z=455 (M+H)$^+$
$R_t$ (HPLC): 1.291 min (method A)

Intermediate 52

(R)-methyl 2-(3-(3,5-difluorophenyl)-5-oxo-8,11-dioxa-1,4-diazaspiro[5.6]dodecan-4-yl)-acetate hydrochloride

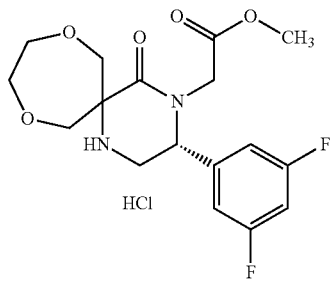 [SMILES: COC(=O)CN1C(=O)C2(COCCOC2)NC[C@H]1c1cc(F)cc(F)c1 ; Cl]

0.13 g (0.28 mmol) tert-butyl (R)-3-(3,5-difluoro-phenyl)-4-methoxycarbonylmethyl-5-oxo-8,11-dioxa-1,4-diazaspiro[5.6]dodecane-1-carboxylate were combined with 20 ml of a 1M methanolic hydrochloric acid solution and stirred for 2 h at 50° C. The reaction mixture was concentrated by rotary evaporation and further reacted without any further purification.

Yield: 100 mg (89% of theoretical)
$R_t$ (HPLC): 0.99 min (method A)

Intermediate 53

(R)-methyl 2-(3-(3,5-difluorophenyl)-1-methyl-5-oxo-8,11-dioxa-1,4-diazaspiro[5.6]dodecan-4-yl) acetate

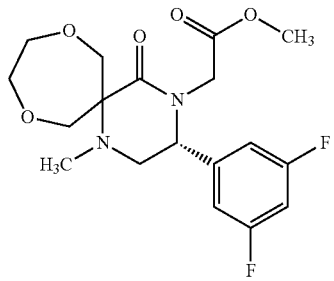 [SMILES: COC(=O)CN1C(=O)C2(COCCOC2)N(C)C[C@H]1c1cc(F)cc(F)c1]

0.10 g (0.25 mmol) (R)-methyl 2-(3-(3,5-difluorophenyl)-5-oxo-8,11-dioxa-1,4-diazaspiro[5.6]dodecan-4-yl)acetate hydrochloride in 20 ml acetonitrile were combined with 83 mg (0.60 mmol) potassium carbonate and with 0.04 ml (0.60 mmol) methyl iodide. The reaction mixture was stirred for 5 days at RT. Then the reaction was evaporated down and reacted without any further purification.

Yield: 75 mg (79% of theoretical)
$R_t$ (HPLC): 1.20 min (method A)

Intermediate 54

(R)-2-(3-(3,5-difluorophenyl)-1-methyl-5-oxo-8,11-dioxa-1,4-diazaspiro[5.6]dodecan-4-yl)-ethanoic acid

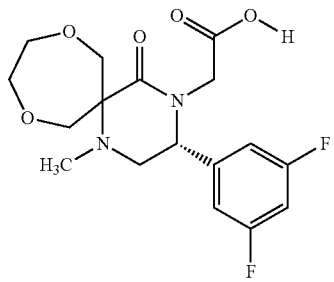 [SMILES: CN1C[C@@H](c2cc(F)cc(F)c2)N(CC(=O)O)C(=O)C12COCCOC2]

7.2 mg (0.30 mmol) lithium hydroxide were added to 75 mg (0.20 mmol) (R)-methyl 2-(3-(3,5-difluorophenyl)-1-methyl-5-oxo-8,11-dioxa-1,4-diazaspiro[5.6]dodecan-4-yl)acetate in 5 ml THF and 1 ml of water. The reaction mixture was stirred for 2 h at RT and then MeOH was distilled off. The residue was made neutral with a 0.1M hydrochloric acid solution and evaporated to dryness.

Yield: 75 mg (quantitative)
$R_t$ (HPLC): 1.0 min (method A)

Intermediate 55

(R)-3-cycloheptylmethyl-6-(3,5-difluoro-phenyl)-piperazin-2-one

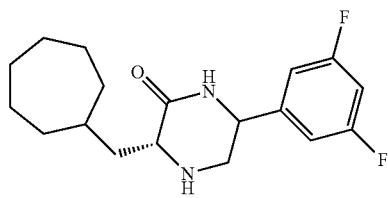 [SMILES: O=C1NC(c2cc(F)cc(F)c2)CN[C@@H]1CC1CCCCCC1]

Under a hydrogen atmosphere 5.5 g (12.0 mmol) methyl (R)-2-(benzyl-{2-(3,5-difluoro-phenyl)-2-[hydroxyimino]-ethyl}-amino)-3-cycloheptyl-propionate (this compound may be prepared analogously to the synthesis of methyl (S)-2-(benzyl-{2-(3,5-difluoro-phenyl)-2-[hydroxyimino]-ethyl}-amino)-3-cycloheptyl-propionate described herein using the corresponding (R)-configured starting component) and 0.70 g palladium on charcoal (10%) were hydrogenated in 30 ml of methanol for 3 days at 50° C. to 60° C. and 3 bar hydrogen pressure. After elimination of the catalyst the filtrate was concentrated by rotary evaporation. Purification was carried out by flash chromatography.

Yield: 1.3 g (34% of theoretical; isomer 3) and 1.4 g (36% of theoretical; isomer 4)
ESI-MS: m/z=323 (M+H)$^+$
$R_t$ (HPLC): 1.004 min/1.076 min (method A)

Intermediate 56a (2R)-tert-butyl-2-(cycloheptylmethyl)-5-(3,5-difluorophenyl)-3-oxopiperazine-1-carboxylate (isomer 3.1)

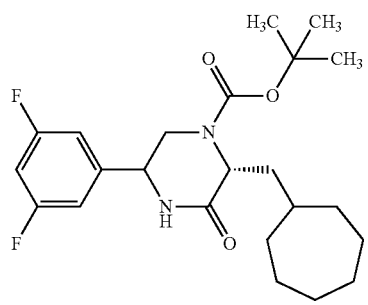 [SMILES: CC(C)(C)OC(=O)N1CC(c2cc(F)cc(F)c2)NC(=O)[C@H]1CC1CCCCCC1]

1.3 g (4.0 mmol) (3R)-3-(cycloheptylmethyl)-6-(3,5-difluorophenyl)piperazin-2-one (isomer 3), 0.89 g (4.1 mmol) di-tert-butyldicarbonate and 0.70 ml (4.1 mmol) DIPEA were stirred overnight at RT in 20 ml acetonitrile. The reaction mixture was evaporated down and the residue was distributed between water and ethyl acetate. The aqueous phase was extracted with ethyl acetate. The organic phases were combined, dried and evaporated down.
Yield: 1.7 g (quantitative)
ESI-MS: m/z=421 (M−H)⁻
$R_t$ (HPLC): 1.791 min (method A)

Intermediate 56b (2R)-tert-butyl-2-(cycloheptylmethyl)-5-(3,5-difluorophenyl)-3-oxopiperazine-1-carboxylate (isomer 4.1)

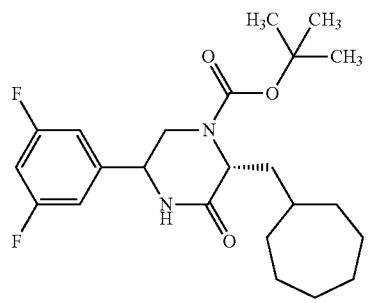 [SMILES: CC(C)(C)OC(=O)N1CC(c2cc(F)cc(F)c2)NC(=O)[C@H]1CC1CCCCCC1]

1.3 g (4.0 mmol) (3R)-3-(cycloheptylmethyl)-6-(3,5-difluorophenyl)piperazin-2-one (isomer 4), 0.89 g (4.1 mmol) di-tert-butyldicarbonate and 0.70 ml (4.1 mmol) DIPEA were stirred overnight at RT in 20 ml acetonitrile. The reaction mixture was evaporated down and the residue was divided between water and ethyl acetate. The aqueous phase was extracted with ethyl acetate. The organic phases were combined, dried and evaporated down.
Yield: 1.6 g (94% of theory))
ESI-MS: m/z=423 (M+H)⁺
$R_t$ (HPLC): 1.905 min (method A)

Intermediate 57a (2R)-tert-butyl-2-(cycloheptylmethyl)-5-(3,5-difluorophenyl)-4-(2-methoxy-2-oxoethyl)-3-oxopiperazine-1-carboxylate (isomer 3.1.1)

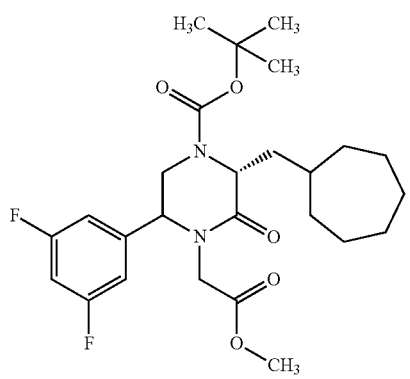 [SMILES: COC(=O)CN1C(=O)[C@@H](CC2CCCCCC2)N(C(=O)OC(C)(C)C)CC1c1cc(F)cc(F)c1]

Under a nitrogen atmosphere 59 mg (1.4 mmol) sodium hydride were added at 0° C. to 0.50 g (1.2 mmol) (2R)-tert-butyl-2-(cycloheptylmethyl)-5-(3,5-difluorophenyl)-3-oxopiperazine-1-carboxylate (isomer 3.1) in 20 ml DMF. After 20 min at 0° C. 0.13 ml (1.4 mmol) methyl bromoacetate were added and the mixture was stirred for 30 min at 0° C. Then the reaction mixture was stirred for 5 h at RT. The reaction mixture was mixed with water and extracted twice with ethyl acetate. The combined organic phases were dried and evaporated down.
Yield: 0.53 g (91% d.Th)
ESI-MS: m/z=495 (M+H)⁺
$R_t$ (HPLC): 1.923 min (method A)

Intermediate 57b (2R)-tert-butyl-2-(cycloheptylmethyl)-5-(3,5-difluorophenyl)-4-(2-methoxy-2-oxoethyl)-3-oxopiperazine-1-carboxylate (isomer 4.1.1)

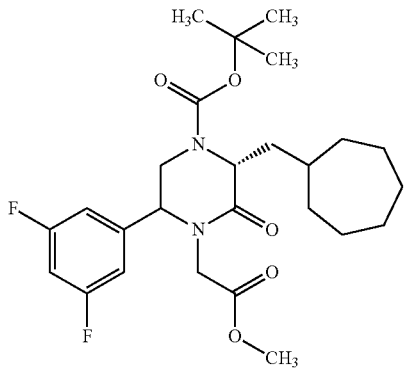 [SMILES: COC(=O)CN1C(=O)[C@@H](CC2CCCCCC2)N(C(=O)OC(C)(C)C)CC1c1cc(F)cc(F)c1]

Under a nitrogen atmosphere 59 mg (1.4 mmol) sodium hydride were added at 0° C. to 0.50 g (1.2 mmol) (2R)-tert-butyl-2-(cycloheptylmethyl)-5-(3,5-difluorophenyl)-3-oxopiperazine-1-carboxylate (isomer 4.1) in 20 ml DMF. After 20 min at 0° C. 0.13 ml (1.4 mmol) methyl bromoacetate were added and the mixture was stirred for 30 min at 0° C. Then the reaction mixture was stirred for 5 h at RT. The reaction mixture was mixed with water and extracted twice with ethyl acetate. The combined organic phases were dried and evaporated down.
Yield: 0.55 g (94% d.Th)
ESI-MS: m/z=495 (M+H)⁺
$R_t$ (HPLC): 1.967 min (method A)

Intermediate 58a 2-((3R)-4-(tert-butoxycarbonyl)-3-(cycloheptylmethyl)-6-(3,5-difluorophenyl)-2-oxopiperazin-1-yl)ethanoic acid (isomer 3.1.1.1)

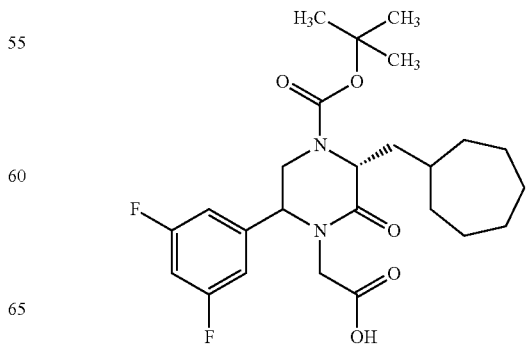

29 mg (1.2 mmol) lithium hydroxide in 1.0 ml of water were added to 0.53 g (1.1 mmol) (2R)-tert-butyl-2-(cycloheptylmethyl)-5-(3,5-difluorophenyl)-4-(2-methoxy-2-oxoethyl)-3-oxopiperazine-1-carboxylate (isomer 3.1.1) in 5 ml THF. After 2 h at RT the mixture was neutralised with 0.1 M hydrochloric acid solution. The reaction mixture was evaporated to dryness by rotary evaporation.

Yield: 0.53 g (quantitative)

$R_t$ (HPLC): 1.744 min (method A)

Intermediate 58b 2-((3R)-4-(tert-butoxycarbonyl)-3-(cycloheptylmethyl)-6-(3,5-difluorophenyl)-2-oxopiperazin-1-yl)ethanoic acid (isomer 4.1.1.1)

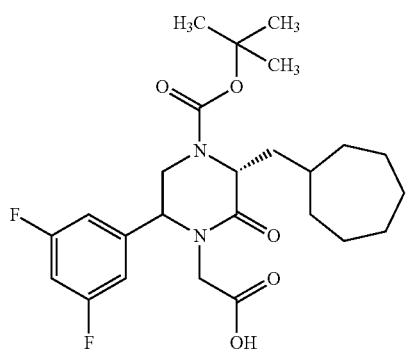 [SMILES: CC(C)(C)OC(=O)N1CC(c2cc(F)cc(F)c2)N(CC(=O)O)C(=O)[C@H]1CC1CCCCCC1]

24 mg (1.3 mmol) lithium hydroxide in 1.0 ml of water were added to 0.55 g (1.1 mmol) (2R)-tert-butyl-2-(cycloheptylmethyl)-5-(3,5-difluorophenyl)-4-(2-methoxy-2-oxoethyl)-3-oxopiperazine-1-carboxylate (isomer 4.1.1) in 5 ml THF. After 2 h at RT the mixture was neutralised with 0.1 M hydrochloric acid solution. The reaction mixture was evaporated to dryness by rotary evaporation.

Yield: 0.52 g (97% of theory))

$R_t$ (HPLC): 1.861 min (method A)

Preparation of the End Compounds

Example 1a 2-((R)-3-(3,5-difluorophenyl)-5-oxo-8,11-dioxa-1,4-diazaspiro[5.6]dodecan-4-yl)-N-((R)-2'-oxo-1,1',2',3-tetrahydrospiro[indene-2,3'-pyrrolo[2,3-b]pyridin]-5-yl)acetamide

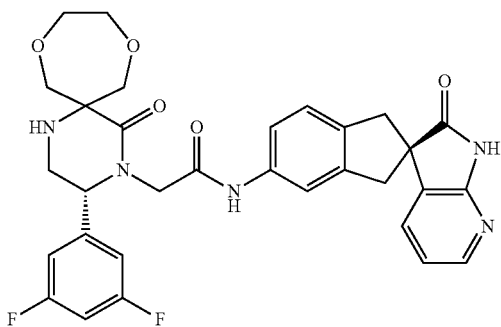 [SMILES: O=C(CN1C(=O)C2(COCCOC2)NC[C@H]1c1cc(F)cc(F)c1)Nc1ccc2c(c1)C[C@@]1(C2)C(=O)Nc2ncccc21]

0.114 g (0.25 mmol) tert-butyl (R)-4-carboxymethyl-3-(3,5-difluoro-phenyl)-5-oxo-8,11-dioxa-1,4-diaza-spiro[5.6]dodecane-1-carboxylate were stirred together with 67.9 mg (0.27 mmol) (R)-5-amino-1,3-dihydrospiro[inden-2,3'-pyrrolo[2,3-b]pyridin]-2'(1'H)-one, 63.3 mg (0.33 mmol) 1-ethyl-3-(3-dimethylaminopropyl)carbodiimide-hydrochloride, 44.6 mg (0.33 mmol) HOBt, 35 µl (0.25 mmol) TEA and 1.5 ml DMF, overnight at RT. The solvent was spun off and the residue was stirred with 15 ml of a methanolic hydrochloric acid (1.25N) for 1 h at 50° C. The reaction mixture was concentrated by rotary evaporation and the residue was purified by PR-HPLC. The product-containing fractions were concentrated by rotary evaporation and the residue was triturated with diisopropylether. After suction filtering the solid was washed with diisopropylether and dried.

Yield: 65 mg (42% of theoretical)

ESI-MS: m/z=590 (M+H)$^+$ $R_t$ (HPLC): 1.10 min (method A)

Example 1b 2-((R)-3-(3,5-difluorophenyl)-5-oxo-8,11-dioxa-1,4-diazaspiro[5.6]dodecan-4-yl)-N-((S)-2'-oxo-1,1',2',3-tetrahydrospiro[inden-2,3'-pyrrolo[2,3-b]pyridin]-5-yl)acetamide

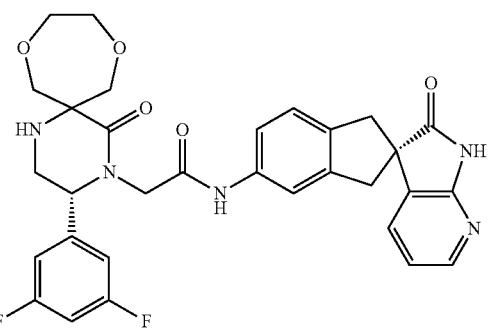

0.114 g (0.25 mmol) tert-butyl (R)-4-carboxymethyl-3-(3,5-difluoro-phenyl)-5-oxo-8,11-dioxa-1,4-diaza-spiro[5.6]dodecane-1-carboxylate were stirred overnight at RT with 67.9 mg (0.27 mmol) (S)-5-amino-1,3-dihydrospiro[inden-2,3'-pyrrolo[2,3-b]pyridin]-2'(1'H)-one, 63.3 mg (0.33 mmol) 1-ethyl-3-(3-dimethylaminopropyl)carbodiimide hydrochloride, 44.6 mg (0.33 mmol) HOBT, 35 µl (0.25 mmol) TEA and 1.5 ml DMF. The solvent was spun off and the residue was stirred with 15 ml of a methanolic hydrochloric acid (1.25N) 1 h at 50° C. The reaction mixture was concentrated by rotary evaporation and the residue was purified by PR-HPLC. The product-containing fractions were concentrated by rotary evaporation and the residue was triturated with diisopropylether. After suction filtering the solid was washed with diisopropylether and dried.

Yield: 50 mg (32% of theoretical)

ESI-MS: m/z=590 (M+H)$^+$ $R_t$ (HPLC): 1.10 min (method A)

Example 13

2-((3S)-3-(cycloheptylmethyl)-6-(3,5-difluorophenyl)-2-oxopiperazin-1-yl)-N-((R)-2'-oxo-1,1',2',3-tetrahydrospiro[inden-2,3'-pyrrol[2,3-b]pyridin]-5-yl)acetamide

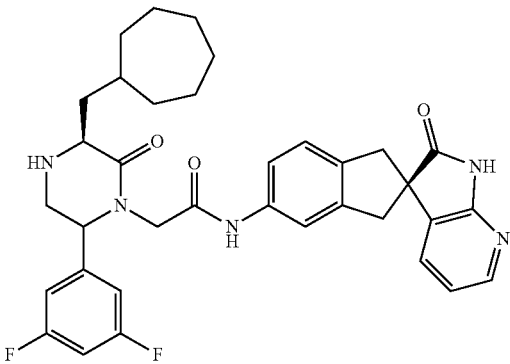 [SMILES: O=C(CN1C(=O)[C@H](CC2CCCCCC2)NCC1c1cc(F)cc(F)c1)Nc1ccc2c(c1)C[C@@]1(C2)C(=O)Nc2ncccc21]

100 mg (0.21 mmol) 2-((3S)-4-(tert-butoxycarbonyl)-3-(cycloheptylmethyl)-6-(3,5-difluorophenyl)-2-oxopiperazin-1-yl)ethanoic acid, 58 mg (0.23 mmol) (R)-5-amino-1,3-dihydrospiro[inden-2,3'-pyrrol[2,3-b]pyridin]-2'(1'H)-one, 56 mg (0.29 mmol) 1-ethyl-3-(3-dimethylaminopropyl)carbodiimide-hydrochloride, 39 mg (0.29 mmol) HOBT, 0.03 ml (0.23 mmol) TEA and 1.50 ml DMF were stirred overnight at RT. The mixture was concentrated by rotary evaporation. The residue was combined with 15 ml of a 1.25M methanolic hydrochloric acid and stirred for 2 h at 50° C. The diastereomers were separated by RP-HPLC. The fractions containing the product were lyophilised.

Diastereomer 1:
  Yield: 16 mg (12% of theoretical)
  ESI-MS: m/z=614 (M+H)$^+$
  R$_t$ (HPLC): 1.13 min (method B)
Diastereomer 2:
  Yield: 10 mg (7% of theoretical)
  ESI-MS: m/z=614 (M+H)$^+$
  R$_t$ (HPLC): 1.19 min (method B)

Example 14

2-((R)-3-(3,5-difluoro-phenyl)-5-oxo-12-oxa-1,4-diaza-dispiro[5.2.5.2]hexadecan-4-yl)-N-((R)-2'-oxo-1,1',2',3-tetrahydrospiro[inden-2,3'-pyrrolo[2,3-b]pyridin]-5-yl)acetamide

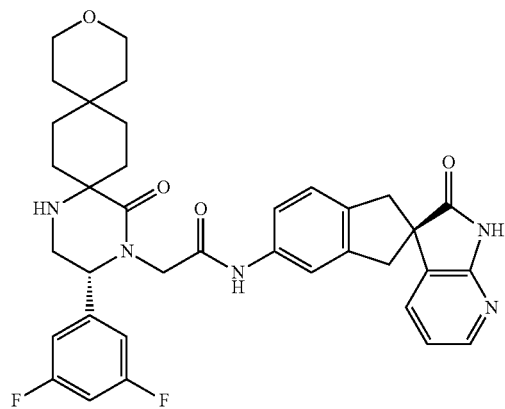 [SMILES: O=C(CN1C(=O)C2(CCC3(CCOCC3)CC2)NC[C@H]1c1cc(F)cc(F)c1)Nc1ccc2c(c1)C[C@@]1(C2)C(=O)Nc2ncccc21]

75 mg (0.15 mmol) tert-butyl 4-carboxymethyl-(3R)-(3,5-difluorophenyl)-5-oxo-12-oxa-1,4-diaza-dispiro[5.2.5.2]hexadecane-1-carboxylate, 40 mg (0.16 mmol) (R)-5-amino-1,3-dihydrospiro[inden-2,3'-pyrrol[2,3-b]pyridin]-2'(1'H)-one, 38 mg (0.20 mmol) 1-ethyl-3-(3-dimethylaminopropyl)carbodiimide-hydrochloride, 27 mg (0.20 mmol) HOBT, 0.02 ml (0.16 mmol) TEA and 1.50 ml DMF were stirred overnight at RT. The reaction mixture was concentrated by rotary evaporation. The residue was stirred with 15 ml of a 1.25M methanolic hydrochloric acid for 1 h at 50° C. The mixture was concentrated by rotary evaporation and the residue was purified by RP-HPLC. The product-containing fractions were combined and lyophilised.

Yield: 59 mg (62% of theoretical)
ESI-MS: m/z=642 (M+H)$^+$
R$_t$ (HPLC): 1.13 min (method A)

Example 15a 2-(6-(3,5-difluorophenyl)-2-oxo-3-(tetrahydro-2H-pyran-4-yl)piperazin-1-yl)-N-((R)-2'-oxo-1,1',2',3-tetrahydrospiro[inden-2,3'-pyrrolo[2,3-b]pyridin]-5-yl)acetamide

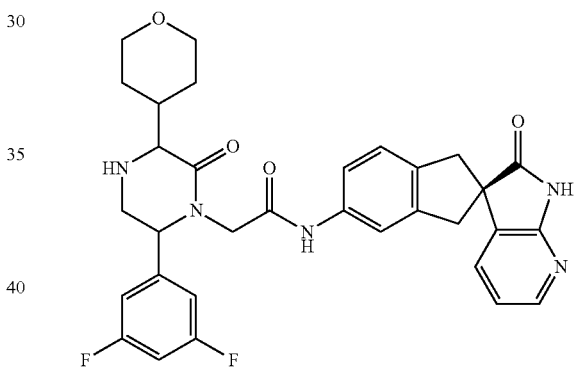

0.10 g (0.22 mmol) 2-(4-(tert-butoxycarbonyl)-6-(3,5-difluorophenyl)-2-oxo-3-(tetrahydro-2H-pyran-4-yl)piperazin-1-yl)ethanoic acid (isomer mixture 1.1.1), 60 mg (0.24 mmol) (R)-5-amino-1,3-dihydrospiro[indene-2,3'-pyrrolo[2,3-b]pyridin]-2'(1'H)-one, 58 mg (0.30 mmol) 1-ethyl-3-(3-dimethylaminopropyl)carbodiimide-hydrochloride, 41 mg (0.30 mmol) HOBT, 0.03 ml (0.24 mmol) TEA and 1.5 ml DMF were stirred overnight at RT. The reaction mixture was concentrated by rotary evaporation. The residue was stirred with 15 ml of a 1.25M methanolic hydrochloric acid solution for 1 h at 50° C. The mixture was concentrated by rotary evaporation and the residue was purified by HPLC. The product-containing fractions were combined and lyophilised. The product was obtained as an isomer mixture.

Yield: 52 mg (40% of theoretical)
ESI-MS: m/z=588 (M+H)$^+$
R$_t$ (HPLC): 1.067 min (method A)

Example 15b 2-(6-(3,5-difluorophenyl)-2-oxo-3-(tetrahydro-2H-pyran-4-yl)piperazin-1-yl)-N-((R)-2'-oxo-1,1',2',3'-tetrahydrospiro[indene-2,3'-pyrrolo[2,3-b]pyridin]-5-yl)acetamide

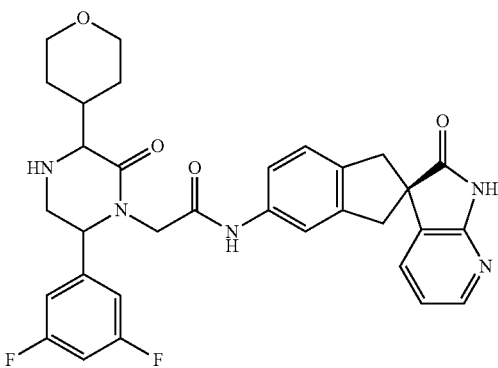 [SMILES: O=C(CN1C(=O)C(C2CCOCC2)NCC1c1cc(F)cc(F)c1)Nc1ccc2c(c1)C[C@@]1(C2)C(=O)Nc2ncccc21]

0.10 g (0.22 mmol) 2-(4-(tert-butoxycarbonyl)-6-(3,5-difluorophenyl)-2-oxo-3-(tetrahydro-2H-pyran-4-yl)piperazin-1-yl)ethanoic acid (isomer mixture 2,2,2), 60 mg (0.24 mmol) (R)-5-amino-1,3-dihydrospiro[indene-2,3'-pyrrolo[2,3-b]pyridin]-2'(1'H)-one, 58 mg (0.30 mmol) 1-ethyl-3-(3-dimethylaminopropyl)carbodiimide-hydrochloride, 41 mg (0.30 mmol) HOBT, 0.03 ml (0.24 mmol) TEA and 1.5 ml DMF were stirred overnight at RT. The reaction mixture was concentrated by rotary evaporation. The residue was stirred with 15 ml of a 1.25M methanolic hydrochloric acid solution for 1 h at 50° C. The mixture was concentrated by rotary evaporation and the residue was purified by HPLC. The product-containing fractions were combined and lyophilised. The product was obtained as a mixture of isomers.

Yield: 42 mg (33% of theoretical)
ESI-MS: m/z=588 (M+H)$^+$
R$_t$ (HPLC): 1.025 min (method A)

Example 16a 2-((3R)-3-(cycloheptylmethyl)-6-(3,5-difluorophenyl)-2-oxopiperazin-1-yl)-N-((R)-2'-oxo-1,1',2',3'-tetrahydrospiro[inden-2,3'-pyrrolo[2,3-b]pyridin]-5-yl)acetamide

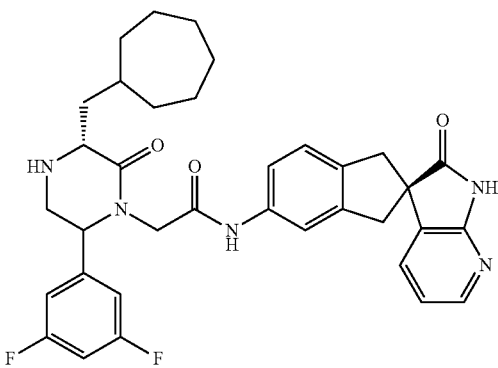 [SMILES: O=C(CN1C(=O)[C@@H](CC2CCCCCC2)NCC1c1cc(F)cc(F)c1)Nc1ccc2c(c1)C[C@@]1(C2)C(=O)Nc2ncccc21]

0.20 g (0.42 mmol) 2-((3R)-4-(tert-butoxycarbonyl)-3-(cycloheptylmethyl)-6-(3,5-difluorophenyl)-2-oxopiperazin-1-yl)ethanoic acid (isomer 3.1.1.1), 0.11 g (0.45 mmol) (R)-5-amino-1,3-dihydrospiro[inden-2,3'-pyrrolo[2,3-b]pyridin]-2'(1'H)-one, 0.11 g (0.55 mmol) 1-ethyl-3-(3-dimethylaminopropyl)-carbodiimide hydrochloride, 74 mg (0.55 mmol) HOBT, 0.06 ml (0.45 mmol) TEA and 2.0 ml DMF were stirred overnight at RT. The reaction mixture was concentrated by rotary evaporation. The residue was stirred with 15 ml of a 1.25M methanolic hydrochloric acid for 2 h at 50° C. The mixture was concentrated by rotary evaporation and the residue was purified by HPLC. The product-containing fractions were combined and lyophilised.

Yield: 80 mg (31% of theoretical)
ESI-MS: m/z=614 (M+H)$^+$
R$_t$ (HPLC): 1.278 min (method A)

Example 16b 2-((3R)-3-(cycloheptylmethyl)-6-(3,5-difluorophenyl)-2-oxopiperazin-1-yl)-N-((R)-2'-oxo-1,1',2',3'-tetrahydrospiro[indene-2,3'-pyrrolo[2,3-b]pyridin]-5-yl)acetamide

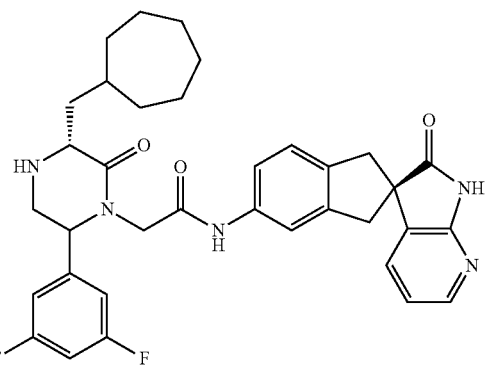

0.20 g (0.42 mmol) 2-((3R)-4-(tert-butoxycarbonyl)-3-(cycloheptylmethyl)-6-(3,5-difluorophenyl)-2-oxopiperazin-1-yl)ethanoic acid (isomer 4.1.1.1), 0.11 g (0.45 mmol) (R)-5-amino-1,3-dihydrospiro[inden-2,3'-pyrrolo[2,3-b]pyridin]-2'(1'H)-one, 0.11 g (0.55 mmol) 1-ethyl-3-(3-dimethylaminopropyl)-carbodiimide hydrochloride, 74 mg (0.55 mmol) HOBT, 0.06 ml (0.45 mmol) TEA and 2.0 ml DMF were stirred overnight at RT. The reaction mixture was concentrated by rotary evaporation. The residue was stirred with 15 ml of a 1.25M methanolic hydrochloric acid for 1 h at 50° C. The mixture was concentrated by rotary evaporation and the residue was purified by HPLC. The product-containing fractions were combined and lyophilised.

Yield: 41 mg (16% of theoretical)
ESI-MS: m/z=614 (M+H)$^+$
R$_t$ (HPLC): 1.313 min (method A)

Example 17

2-((R)-3-(3,5-difluorophenyl)-1-methyl-5-oxo-8,11-dioxa-1,4-diazaspiro[5.6]dodecan-4-yl)-N-((R)-2'-oxo-1,1',2',3'-tetrahydrospiro[inden-2,3'-pyrrolo[2,3-b]pyridin]-5-yl)acetamide

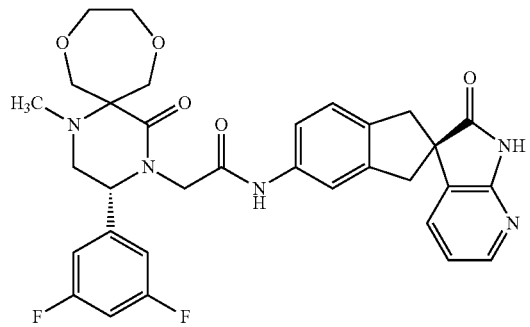

75 mg (0.20 mmol) (R)-2-(3-(3,5-difluorophenyl)-1-methyl-5-oxo-8,11-dioxa-1,4-diazaspiro[5.6]dodecan-4-yl)-ethanoic acid, 55 mg (0.22 mmol) (R)-5-amino-1,3-dihydrospiro[inden-2,3'-pyrrolo[2,3-b]pyridin]-2'(1'H)-one, 50 mg (0.26 mmol) 1-ethyl-3-(3-dimethylaminopropyl)carbodiimide-hydrochloride, 35 mg (0.26 mmol) HOBT, 0.07 ml (0.50 mmol) TEA and 1.5 ml DMF were stirred overnight at RT. The reaction mixture was concentrated by rotary evaporation. The residue was stirred with 15 ml of a 1.25M methanolic hydrochloric acid for 1 h at 50° C. The mixture was concentrated by rotary evaporation and the residue was purified by HPLC. The fractions containing the product were combined and lyophilised.

Yield: 16 mg (13% of theoretical)
ESI-MS: m/z=604 (M+H)+
R$_t$ (HPLC): 1.20 min (method A)

Example 18

2-(3-(3-methoxyphenyl)-5-oxo-8,11-dioxa-1,4-diazaspiro[5.6]dodecan-4-yl)-N—((R)-2'-oxo-1',2',3-tetrahydrospiro[inden-2,3'-pyrrolo[2,3-b]pyridin]-5-yl)acetamide

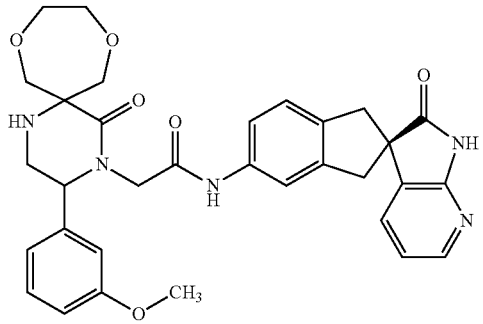 [SMILES: COc1cccc(C2CNC3(COCCOC3)C(=O)N2CC(=O)Nc2ccc3c(c2)C[C@@]2(C3)C(=O)Nc3ncccc32)c1]

0.60 g (0.79 mmol) tert-butyl 3-(3-methoxyphenyl)-5-oxo-4-(2-oxo-2-((R)-2'-oxo-1,1',2',3-tetrahydrospiro[indene-2,3'-pyrrolo[2,3-b]pyridin]-5-ylamino)ethyl)-8,11-dioxa-1,4-diaza-spiro[5.6]dodecane-1-carboxylate in 5 ml of methanol were combined with 15 ml of a 1.25 M methanolic hydrochloric acid and stirred for 3 h at 50° C. The reaction mixture was concentrated by rotary evaporation and neutralised with saturated NaHCO₃ solution. The precipitate formed was suction filtered, washed with water and dried.

Yield: 250 mg (54% of theoretical)
ESI-MS: m/z=584 (M+H)+
R$_t$ (HPLC): 1.02 min (method A)

Example 19

N-(5-chloro-2'-oxo-1,1',2',3-tetrahydrospiro[inden-2,3'-pyrrolo[2,3-b]pyridin]-6-yl)-2-((R)-3-(3,5-difluorophenyl)-5-oxo-8,11-dioxa-1,4-diazaspiro[5.6]dodecan-4-yl)acetamide

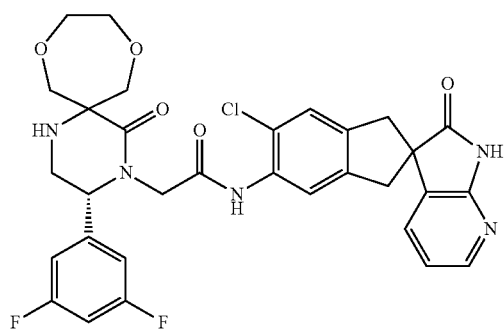 [SMILES: O=C(CN1C(=O)C2(COCCOC2)NC[C@H]1c1cc(F)cc(F)c1)Nc1cc2c(cc1Cl)CC1(C2)C(=O)Nc2ncccc21]

40 mg (0.06 mmol) (3R)-tert-butyl 4-(2-(5-chloro-2'-oxo-1,1',2',3-tetrahydrospiro[inden-2,3'-pyrrolo[2,3-b]pyridin]-6-ylamino)-2-oxoethyl)-3-(3,5-difluorophenyl)-5-oxo-8,11-dioxa-1,4-diazaspiro[5.6]dodecane-1-carboxylate were combined with 30 ml of a 1N methanolic hydrochloric acid solution and stirred for 1 h at 50° C. The reaction mixture was concentrated by rotary evaporation. The residue was taken up in water and adjusted to pH=8 with saturated NaHCO₃ solution. The precipitate formed was suction filtered, washed with water and dried.

Yield: 19 mg (55% of theoretical)
ESI-MS: m/z=624 (M+H)+
R$_t$ (HPLC): 1.17 min (method A)

Example 20

(R)-tert-butyl 5-oxo-4-(2-oxo-2-((R)-2'-oxo-1,1',2',3-tetrahydrospiro[inden-2,3'-pyrrolo[2,3-b]pyridin]-5-ylamino)ethyl)-3-phenyl-8,11-dioxa-1,4-diazaspiro[5.6]dodecane-1-carboxylate

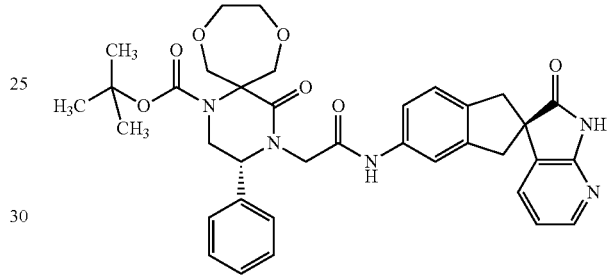

0.21 g (0.5 mmol) (R)-2-(1-(tert-butoxycarbonyl)-5-oxo-3-phenyl-8,11-dioxa-1,4-diaza-spiro[5.6]dodecan-4-yl)ethanoic acid in 3 ml DMF were combined with 0.38 g (1 mmol) HATU and 0.18 ml (1.3 mmol) TEA and stirred for 10 min at RT. Then 0.13 mg (0.5 mmol) (S)-5-amino-1,3-dihydrospiro[inden-2,3'-pyrrolo[2,3-b]pyridin]-2'(1'H)-one were added and the mixture was stirred overnight at RT. The reaction mixture was poured onto ice water. The precipitate formed was suction filtered, washed with water and dried.

Yield: 320 mg (98% of theoretical)
ESI-MS: m/z=654 (M+H)+
R$_t$ (HPLC): 1.41 min (method A)

Example 21

N—((R)-2'-oxo-1,1',2',3-tetrahydrospiro[inden-2,3'-pyrrolo[2,3-b]pyridin]-5-yl)-2-((R)-5-oxo-3-phenyl-8,11-dioxa-1,4-diazaspiro[5.6]dodecan-4-yl)acetamide

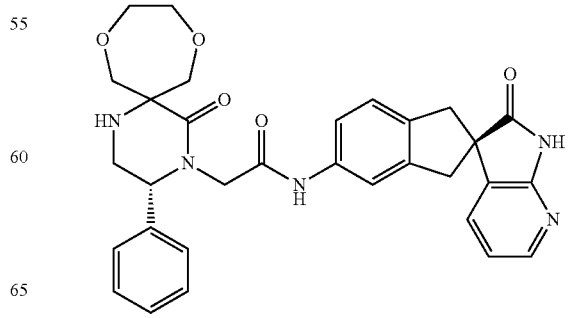

0.27 g (0.41 mmol) (R)-tert-butyl 5-oxo-4-(2-oxo-2-((R)-2'-oxo-1,1',2',3-tetrahydrospiro[inden-2,3'-pyrrolo-[2,3-b]pyridin]-5-ylamino)ethyl)-3-phenyl-8,11-dioxa-1,4-diazaspiro[5.6]-dodecane-1-carboxylate in 5 ml of methanol were combined with 10 ml of a 1.25 M methanolic hydrochloric acid and stirred for 3 h at 50° C. The reaction mixture was concentrated by rotary evaporation and neutralised with saturated NaHCO₃ solution. The precipitate formed was suction filtered, washed with water and dried.

Yield: 160 mg (71% of theoretical)
ESI-MS: m/z=554 (M+H)⁺
$R_t$ (HPLC): 1.00 min (method A)

Example 22

2-((R)-3-(4-fluorophenyl)-5-oxo-8,11-dioxa-1,4-diazaspiro[5.6]dodecan-4-yl)-N-((R)-2'-oxo-1,1',2',3-tetrahydrospiro[inden-2,3'-pyrrolo[2,3-b]pyridin]-5-yl)acetamide

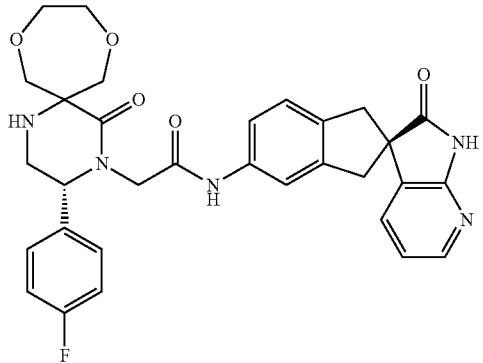 [SMILES: O=C(CN1C(=O)C2(COCCOC2)NC[C@H]1c1ccc(F)cc1)Nc1ccc2c(c1)C[C@@]1(C2)C(=O)Nc2ncccc21]

0.10 g (0.17 mmol) of a racemate of 2-(3-(4-fluorophenyl)-5-oxo-8,11-dioxa-1,4-diaza-spiro[5,6]dodecan-4-yl)-N—((R)-2'-oxo-1,1',2',3-tetrahydrospiro[inden-2,3'-pyrrolo-[2,3-b]pyridin]-5-yl)acetamide were resolved into the corresponding enantiomers using an SFC apparatus (1×IB, eluant: 30% MeOH+0.2% DEA; flow: 10 ml/min, c=25 mg/min).

Yield: 30.3 mg (30% of theoretical)
ESI-MS: m/z=570 (M−H)⁻
$R_t$ (chirale-HPLC): 3.63 min (method Daicel IB, 250 mm×4.6 mm, 5 μm, 40° C., CO₂, MeOH+DEA, isocratic 30%. 4 ml/min)

Example 23

2-(3-(3-fluorophenyl)-5-oxo-8,11-dioxa-1,4-diaza-spiro[5.6]dodecan-4-yl)-N—((R)-2'-oxo-1,1',2',3-tetrahydrospiro[inden-2,3'-pyrrolo[2,3-b]pyridin]-5-yl)acetamide

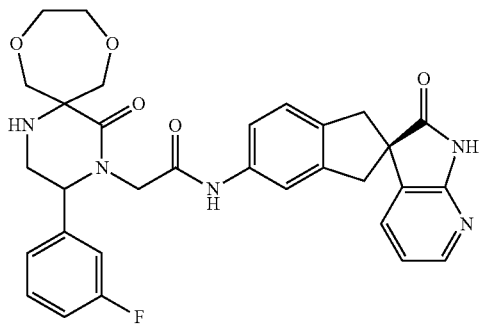 [SMILES: O=C(CN1C(=O)C2(COCCOC2)NCC1c1cccc(F)c1)Nc1ccc2c(c1)C[C@@]1(C2)C(=O)Nc2ncccc21]

0.23 g (0.52 mmol) 2-(1-(tert-butoxycarbonyl)-3-(3-fluorophenyl)-5-oxo-8,11-dioxa-1,4-diazaspiro[5.6]dodecan-4-yl)ethanoic acid, 0.15 mg (0.58 mmol) (R)-5-amino-1,3-dihydrospiro[inden-2,3'-pyrrolo[2,3-b]pyridin]-2'(1'H)-one, 0.13 g (0.70 mmol) 1-ethyl-3-(3-dimethylaminopropyl)carbodiimide hydrochloride, 95 mg (0.7 mmol) HOBT, 0.08 ml (0.58 mmol) TEA and 2 ml DMF were stirred overnight at RT. The mixture was concentrated by rotary evaporation. The residue was combined with 15 ml of a 1.25M methanolic hydrochloric acid and stirred for 2 h at 50° C. The reaction mixture was evaporated down and purified by HPLC.

Yield: 51 mg (17% of theoretical)
ESI-MS: m/z=572 (M+H)⁺
$R_t$ (HPLC): 1.047 min (method A)

Example 24

2-((R)-3-(3,5-difluorophenyl)-5-oxo-8,11-dioxa-1,4-diazaspiro[5.6]dodecan-4-yl)-N-(2'-oxo-1',2',5,7-tetrahydrospiro[cyclopenta[b]pyridin-6,3'-pyrrolo[2,3-b]pyridin]-3-yl)acetamide

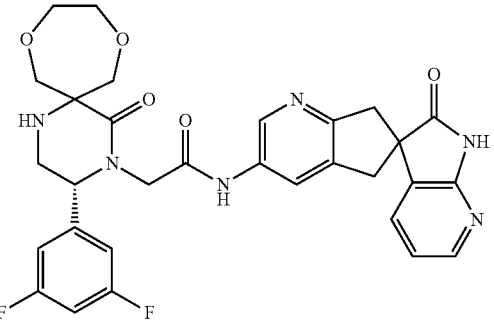

0.18 g (0.26 mmol) (3R)-tert-butyl 3-(3,5-difluorophenyl)-5-oxo-4-(2-oxo-2-(2'-oxo-1',2',5,7-tetrahydrospiro[cyclopenta[b]pyridin-6,3'-pyrrolo[2,3-b]pyridin]-3-ylamino)ethyl)-8,11-dioxa-1,4-diazaspiro[5.6]dodecane-1-carboxylate were combined with 30 ml of a 1N methanolic hydrochloric acid solution and stirred for 1 h at 50° C. The reaction mixture was concentrated by rotary evaporation and purified by HPLC. The product fractions were evaporated down, neutralised with sodium hydrogen carbonate and the aqueous phase was extracted with DCM. The organic phase was concentrated by rotary evaporation. The residue was triturated with diethyl ether, suction filtered, washed with diethyl ether and dried.

Yield: 14 mg (9.1% of theoretical)
ESI-MS: m/z=589 (M−H)⁻
$R_t$ (HPLC): 0.90 min (method A)

The following Examples describe the preparation of pharmaceutical formulations which contain as active substance any desired compound of general formula I:

Example I

Capsules for powder inhalation containing 1 mg of active ingredient
Composition:
1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of Preparation:
The active ingredient is ground to the particle size required for inhaled substances. The ground active ingredient is homogeneously mixed with the lactose. The mixture is transferred into hard gelatine capsules.

Example II

Inhalable solution for Respimat® containing 1 mg of active ingredient
Composition:
1 puff contains:

| | |
|---|---|
| active ingredient | 1.0 mg |
| benzalkonium chloride | 0.002 mg |
| disodium edetate | 0.0075 mg |
| purified water ad | 15.0 μl |

Method of Preparation:
The active ingredient and benzalkonium chloride are dissolved in water and transferred into Respimat® cartridges.

Example III

Inhalable solution for nebulisers containing 1 mg of active ingredient
Composition:
1 vial contains:

| | |
|---|---|
| active ingredient | 0.1 g |
| sodium chloride | 0.18 g |
| benzalkonium chloride | 0.002 g |
| purified water ad | 20.0 ml |

Method of Preparation:
The active ingredient, sodium chloride and benzalkonium chloride are dissolved in water.

Example IV

Propellant gas-operated metered dose aerosol containing 1 mg of active ingredient
Composition:
1 puff contains:

| | |
|---|---|
| active ingredient | 1.0 mg |
| lecithin | 0.1% |
| propellant gas ad | 50.0 μl |

Method of Preparation:
The micronised active ingredient is homogeneously suspended in the mixture of lecithin and propellant gas. The suspension is transferred into a pressurised container with a metering valve.

Example V

Nasal spray containing 1 mg of active ingredient
Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:
The active ingredient and the excipients are dissolved in water and transferred into a suitable container.

Example VI

Injectable solution containing 5 mg of active substance per 5 ml
Composition:

| | |
|---|---|
| active substance | 5 mg |
| glucose | 250 mg |
| human serum albumin | 10 mg |
| glycofurol | 250 mg |
| water for injections ad | 5 ml |

Preparation:
Glycofurol and glucose are dissolved in water for injections (WfI); human serum albumin is added; active ingredient is dissolved with heating; made up to specified volume with WfI; transferred into ampoules under nitrogen gas.

Example VII

Injectable solution containing 100 mg of active substance per 20 ml
Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 10 ml |

Preparation:
Polysorbate 80, sodium chloride, monopotassium dihydrogen phosphate and disodium hydrogen phosphate are dissolved in water for injections (WfI); human serum albumin is added; active ingredient is dissolved with heating; made up to specified volume with WfI; transferred into ampoules.

Example VIII

Lyophilisate containing 10 mg of active substance

Composition:

| Active substance | 10 mg |
|---|---|
| Mannitol | 300 mg |
| human serum albumin | 20 mg |
| water for injections ad | 2 ml |

Preparation:

Mannitol is dissolved in water for injections (WfI); human serum albumin is added; active ingredient is dissolved with heating; made up to specified volume with WfI; transferred into vials; freeze-dried.

Solvent for Lyophilisate:

| Polysorbate 80 = Tween 80 | 20 mg |
|---|---|
| mannitol | 200 mg |
| water for injections ad | 10 ml |

Preparation:

Polysorbate 80 and mannitol are dissolved in water for injections (WfI); transferred into ampoules.

Example IX

Tablets containing 20 mg of active substance

Composition:

| active substance | 20 mg |
|---|---|
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

Example X

Capsules containing 20 mg active substance

Composition:

| active substance | 20 mg |
|---|---|
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size 3 hard gelatine capsules in a capsule filling machine.

Example XI

Suppositories containing 50 mg of active substance

Composition:

| active substance | 50 mg |
|---|---|
| hard fat (Adeps solidus) q.s. Ad | 1700 mg |

Preparation:

Hard fat is melted at about 38° C.; ground active substance is homogeneously dispersed in the molten hard fat; after cooling to about 35° C. it is poured into chilled moulds.

Example XII

Injectable solution containing 10 mg of active substance per 1 ml

Composition:

| active substance | 10 mg |
|---|---|
| mannitol | 50 mg |
| human serum albumin | 10 mg |
| water for injections ad | 1 ml |

Preparation:

Mannitol is dissolved in water for injections (WfI); human serum albumin is added; active ingredient is dissolved with heating; made up to specified volume with WfI; transferred into ampoules under nitrogen gas.

The invention claimed is:

1. A compound of the formula I

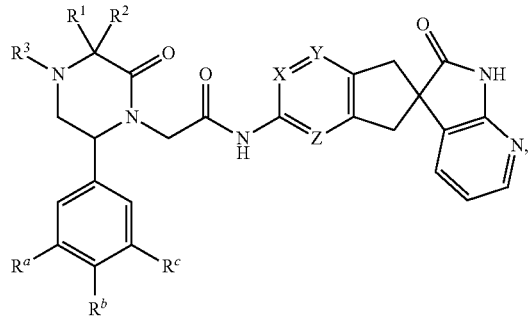

(I)

wherein

X denotes C—H, or C—Cl,

Y, Z independently of one another each denote CH, (a) $R^1$ denotes H, $R^2$ denotes $R^{2.1}$—$C_{0-1}$-alkylene, $R^{2.1}$ denotes a group selected from

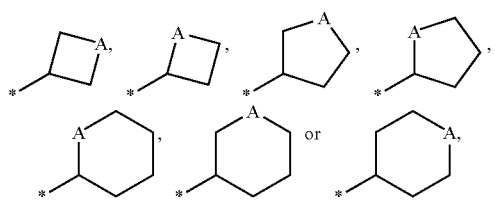

and

A denotes —O—, —S—, —S(O)— or —S(O₂)—; or (b) R¹ denotes H,
R² denotes R$^{2.1}$—CH₂— and
R$^{2.1}$ denotes a group

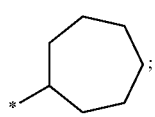

or (c) R¹ and R² together with the carbon atom to which they are attached denote a C$_{4-6}$-cycloalkyl group which is spirocyclically linked in each case to an oxetane or tetrahydropyran ring; or (d) R¹ and R² together with the carbon atom to which they are attached denote a group

and

R³ denotes H, —C(O)—O—C$_{1-4}$-alkyl or a C$_{1-6}$-alkyl group which may be substituted by 1, 2, 3, 4 or 5 fluorine atoms,
R$^a$ denotes H, F, —OCH₃ or —OCF₃,
R$^b$ denotes H, F, —OCH₃ or —OCF₃, and
R$^c$ denotes H, F, —OCH₃ or —OCF₃,
or a physiologically acceptable salt thereof.

2. A compound of the formula I according to claim 1, wherein
X, Y, Z in each case denote C—H,
(a) R¹ denotes H and
R² denotes a group selected from

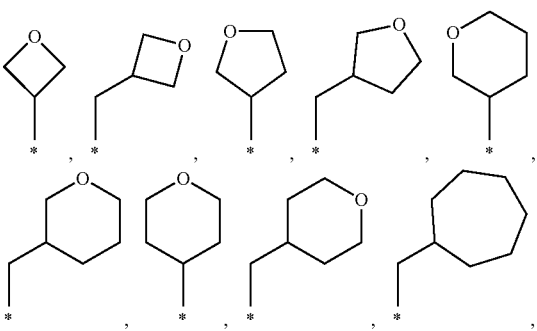

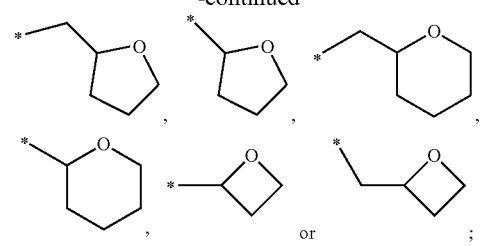

or (b) R¹ and R² together with the carbon atom to which they are attached denote a group selected from

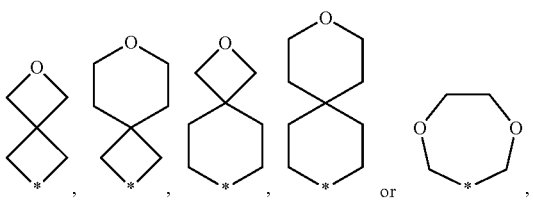

and

R³ denotes H, —C(O)—O—C$_{1-4}$-alkyl or a C$_{1-6}$-alkyl group which may be substituted by 1, 2, 3, 4 or 5 fluorine atoms,
R$^a$ denotes H, F, —OCH₃ or —OCF₃,
R$^b$ denotes H, F, —OCH₃ or —OCF₃, and
R$^c$ denotes H, F, —OCH₃ or —OCF₃,
or a physiologically acceptable salt thereof.

3. A compound of the formula I according to claim 1, wherein
X, Y, Z in each case denotes C—H,
R¹ denotes H,
R² denotes a group selected from

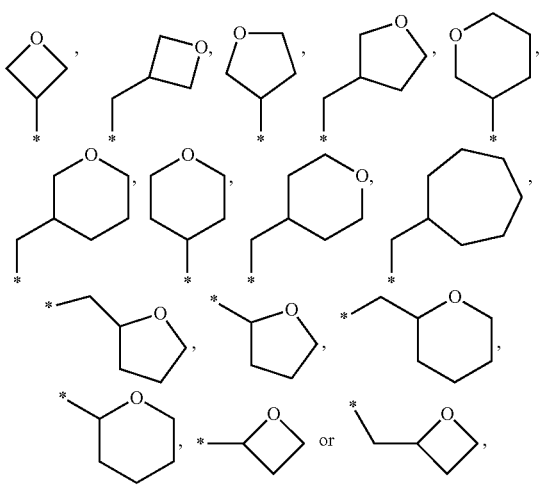

R³ denotes H, —C(O)—O—C$_{1-4}$-alkyl or a C$_{1-6}$-alkyl group which may be substituted by 1, 2, 3, 4 or 5 fluorine atoms,
R$^a$ denotes H, F, —OCH₃ or —OCF₃,
R$^b$ denotes H, F, —OCH₃ or —OCF₃, and
R$^c$ denotes H, F, —OCH₃ or —OCF₃,
or a physiologically acceptable salt thereof.

4. A compound of the formula I according to claim 1, wherein

X, Y, Z in each case denote C—H,

R¹ denotes H,

R² denotes a group

[cycloheptylmethyl structure],

R³ denotes H, —C(O)—O—C₁₋₄-alkyl or a C₁₋₆-alkyl group which may be substituted by 1, 2, 3, 4 or 5 fluorine atoms, Rᵃ denotes H, F, —OCH₃ or —OCF₃, Rᵇ denotes H, F, —OCH₃ or —OCF₃, and Rᶜ denotes H, F, —OCH₃ or —OCF₃, or a physiologically acceptable salt thereof.

5. A compound of the formula I according to claim 1, wherein

X, Y, Z in each case denote C—H,

R¹ and R² together with the carbon atom to which they are attached denote a group selected from

[five spirocyclic structures containing O],

R³ denotes H, —C(O)—O—C₁₋₄-alkyl or a C₁₋₆-alkyl group which may be substituted by 1, 2, 3, 4 or 5 fluorine atoms, Rᵃ denotes H, F, —OCH₃ or —OCF₃, Rᵇ denotes H, F, —OCH₃ or —OCF₃, and Rᶜ denotes H, F, —OCH₃ or —OCF₃, or a physiologically acceptable salt thereof.

6. A compound of the formula I according to claim 1, wherein in each case denote C—H, R¹ and R² together with the carbon atom to which they are attached denote a group

[spirocyclic structure with O],

R³ denotes H, —C(O)—O—C₁₋₄-alkyl or a C₁₋₆-alkyl group which may be substituted by 1, 2, 3, 4 or 5 fluorine atoms, Rᵃ denotes H, F, —OCH₃ or —OCF₃, Rᵇ denotes H, F, —OCH₃ or —OCF₃, and Rᶜ denotes H, F, —OCH₃ or —OCF₃, or a physiologically acceptable salt thereof.

7. A compound of the formula I according to claim 1, wherein

X, Y, Z in each case denote C—H,

R¹ and R² together with the carbon atom to which they are attached denote a group

[7-membered ring with two O atoms],

R³ denotes H, —C(O)—O—C₁₋₄-alkyl or a C₁₋₆-alkyl group which may be substituted by 1, 2, 3, 4 or 5 fluorine atoms, Rᵃ denotes H, F, —OCH₃ or —OCF₃, Rᵇ denotes H, F, —OCH₃ or —OCF₃, and Rᶜ denotes H, F, —OCH₃ or —OCF₃, or a physiologically acceptable salt thereof.

8. A compound of the formula Ia (Ia)

[complex structural formula]

wherein

X denotes C—H, or C—Cl,

Y, Z independently of one another each denote CH, (a) R¹ denotes H,

R² denotes R²·¹—C₀₋₁-alkylene,

R²·¹ denotes a group selected from

[four and three cyclic structures labeled with A], and

A denotes —O—, —S—, —S(O)— or —S(O₂)—; or (b) R¹ denotes H,

R² denotes R²·¹—CH₂— and

R²·¹ denotes a group

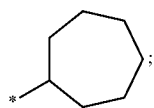

or
  (c) R¹ and R² together with the carbon atom to which they are attached denote a C₄₋₆-cycloalkyl group which is spirocyclically linked in each case to an oxetane or tetrahydropyran ring; or
  (d) R¹ and R² together with the carbon atom to which they are attached denote a group

and

R³ denotes H or CH₃, or a physiologically acceptable salt thereof.

9. A compound of formula I according to claim 1, wherein
X denotes CH,
Y denotes CH and
Z denotes CH,
or a physiologically acceptable salt thereof.

10. A compound of formula Ia according to claim 8, wherein,
R³ denotes H or CH₃,
X denotes CH,
Y denotes CH and
Z denotes CH,
or a physiologically acceptable salt thereof.

11. A compound of the formula I according to claim 1, selected from the group consisting of:

| No. | Structure |
|---|---|
| (1) | 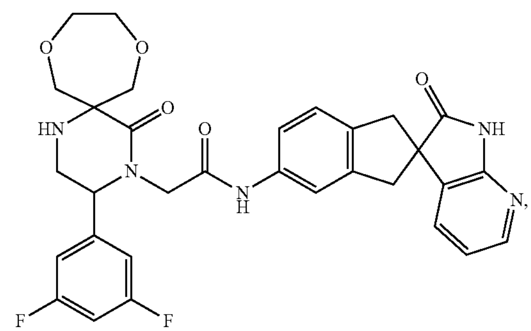 [SMILES: O=C(CN1C(=O)C2(COCCOC2)NCC1c1cc(F)cc(F)c1)Nc1ccc2c(c1)CC1(C2)C(=O)Nc2ncccc21] |
| (1a) | 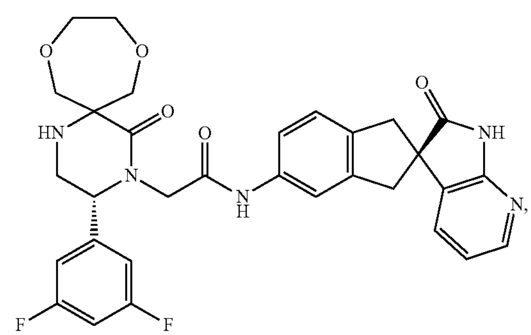 [SMILES: O=C(CN1C(=O)C2(COCCOC2)NC[C@H]1c1cc(F)cc(F)c1)Nc1ccc2c(c1)C[C@@]1(C2)C(=O)Nc2ncccc21] |
| (1b) | 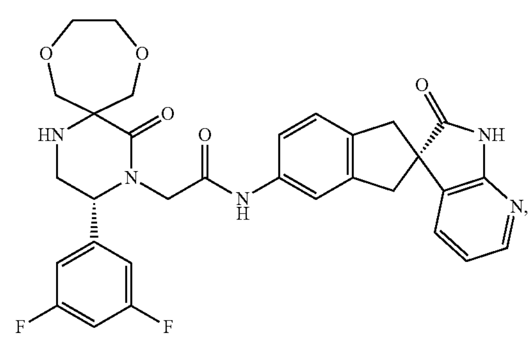 [SMILES: O=C(CN1C(=O)C2(COCCOC2)NC[C@H]1c1cc(F)cc(F)c1)Nc1ccc2c(c1)C[C@]1(C2)C(=O)Nc2ncccc21] |

-continued
| No. | Structure |
|---|---|
| (3) | 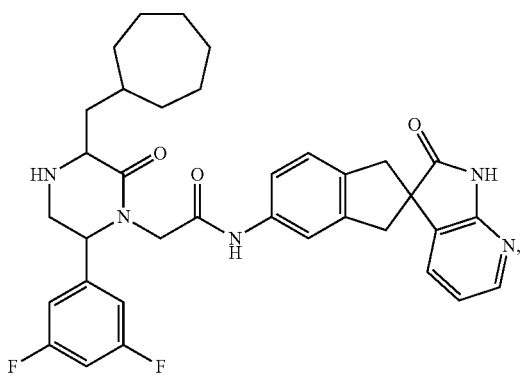 [SMILES: O=C(CN1C(=O)C(CC2CCCCCC2)NCC1c1cc(F)cc(F)c1)Nc1ccc2c(c1)CC1(C2)C(=O)Nc2ncccc21] |
| (5) | 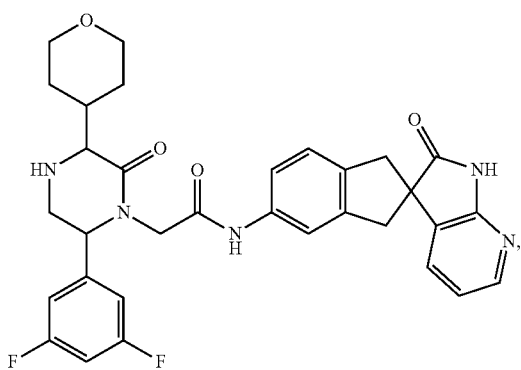 [SMILES: O=C(CN1C(=O)C(C2CCOCC2)NCC1c1cc(F)cc(F)c1)Nc1ccc2c(c1)CC1(C2)C(=O)Nc2ncccc21] |
| (7) | 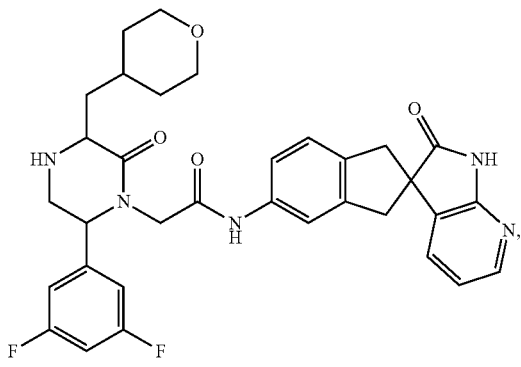 [SMILES: O=C(CN1C(=O)C(CC2CCOCC2)NCC1c1cc(F)cc(F)c1)Nc1ccc2c(c1)CC1(C2)C(=O)Nc2ncccc21] |
| (9) | 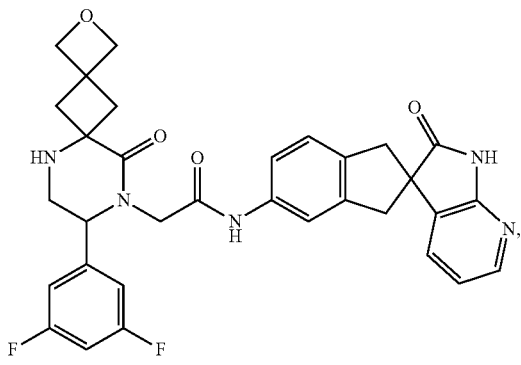 [SMILES: O=C(CN1C(=O)C2(CC3(COC3)C2)NCC1c1cc(F)cc(F)c1)Nc1ccc2c(c1)CC1(C2)C(=O)Nc2ncccc21] |

| No. | Structure |
|---|---|
| (11) | 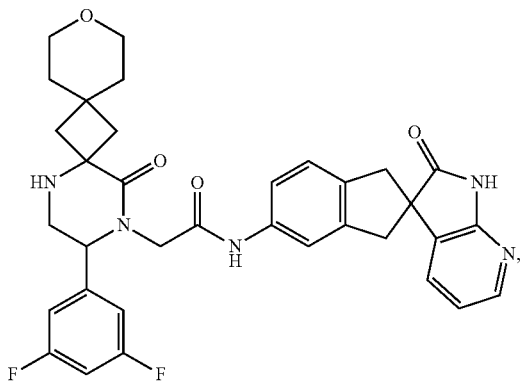 [SMILES: O=C(CN1C(=O)C2(CC3(CCOCC3)C2)NCC1c1cc(F)cc(F)c1)Nc1ccc2c(c1)CC1(C2)C(=O)Nc2ncccc21] |
| (13) | 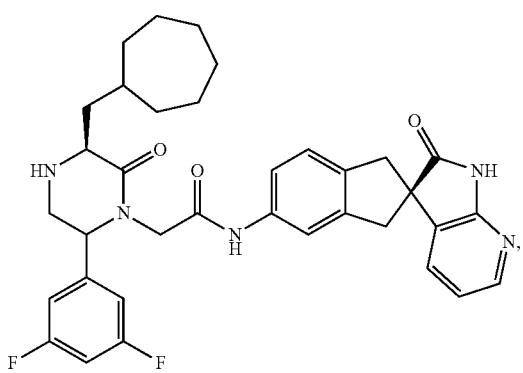 [SMILES: O=C(CN1C(=O)[C@H](CC2CCCCCC2)NCC1c1cc(F)cc(F)c1)Nc1ccc2c(c1)C[C@@]1(C2)C(=O)Nc2ncccc21] |
| (14) | 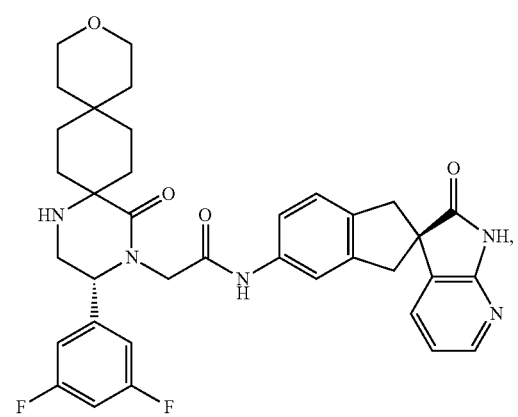 [SMILES: O=C(CN1C(=O)C2(CCC3(CCOCC3)CC2)NC[C@H]1c1cc(F)cc(F)c1)Nc1ccc2c(c1)C[C@@]1(C2)C(=O)Nc2ncccc21] |
| (15) | 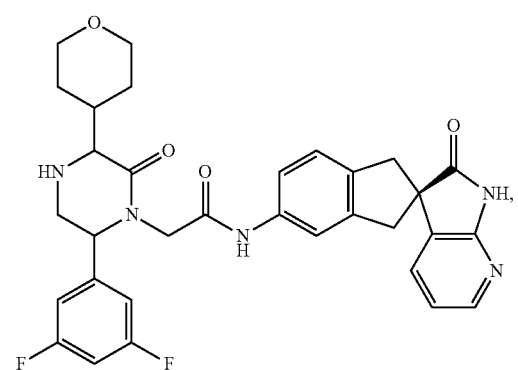 [SMILES: O=C(CN1C(=O)C(C2CCOCC2)NCC1c1cc(F)cc(F)c1)Nc1ccc2c(c1)C[C@@]1(C2)C(=O)Nc2ncccc21] |

| No. | Structure |
|---|---|
| (16) | 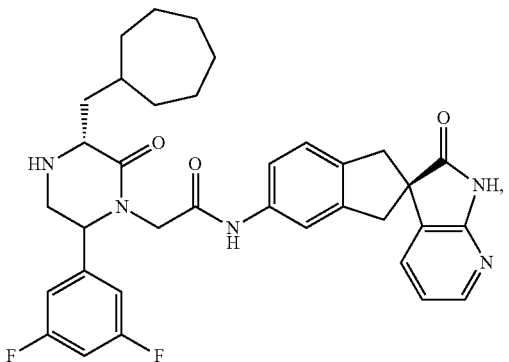 [SMILES: O=C(CN1C(=O)[C@@H](CC2CCCCCC2)NCC1c1cc(F)cc(F)c1)Nc1ccc2c(c1)C[C@@]1(C2)C(=O)Nc2ncccc21] |
| (17) | 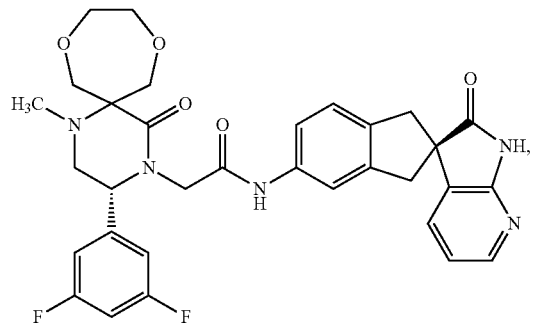 [SMILES: CN1C[C@@H](c2cc(F)cc(F)c2)N(CC(=O)Nc2ccc3c(c2)C[C@@]2(C3)C(=O)Nc3ncccc32)C(=O)C12COCCOC2] |
| (18) | 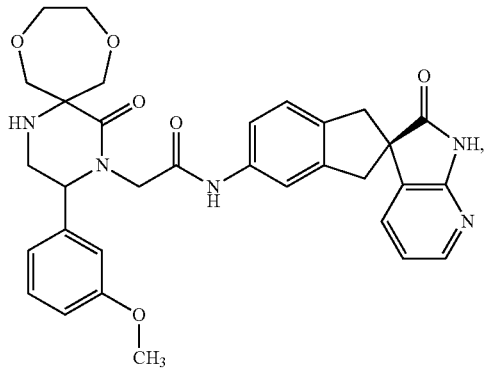 [SMILES: COc1cccc(C2CNC3(COCCOC3)C(=O)N2CC(=O)Nc2ccc3c(c2)C[C@@]2(C3)C(=O)Nc3ncccc32)c1] |
| (19) | 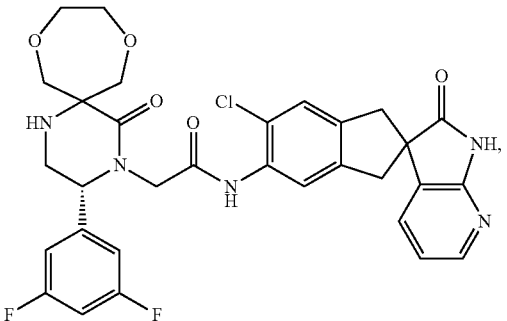 [SMILES: O=C(CN1C(=O)C2(COCCOC2)NC[C@H]1c1cc(F)cc(F)c1)Nc1cc2c(cc1Cl)CC1(C2)C(=O)Nc2ncccc21] |

| No. | Structure |
|---|---|
| (20) | [structure] |
| (21) | [structure] |
| (22) | [structure] and |
| (23) | [structure] | or a physiologically acceptable salt thereof.

12. A pharmaceutical composition comprising a compound according to claim 1, or a salt thereof, and a carrier or diluent.

13. A method for treating migraine or cluster headache which comprises administering to a host suffering from the same a therapeutically effective amount of a compound according to claim 1, or a physiologically acceptable salt thereof.

* * * * *